United States Patent [19]

Garfield et al.

[11] Patent Number: 5,776,073
[45] Date of Patent: Jul. 7, 1998

[54] METHOD AND APPARATUS FOR ANALYZING UTERINE ELECTRICAL ACTIVITY FROM SURFACE MEASUREMENTS FOR OBSTETRICAL DIAGNOSIS

[75] Inventors: Robert E. Garfield, Friendswood, Tex.; Mary B. Boyle, Washington, D.C.

[73] Assignee: Board of Regents, University of Texas System, Austin, Tex.

[21] Appl. No.: 845,689

[22] Filed: Apr. 25, 1997

Related U.S. Application Data

[63] Continuation-in-part of Ser. No. 483,755, Jun. 7, 1995, Pat. No. 5,623,939, which is a continuation-in-part of Ser. No. 246,214, May 19, 1994, Pat. No. 5,546,953.

[51] Int. Cl.$^6$ .................................................. A61B 5/04
[52] U.S. Cl. ............................................ 600/546; 600/591
[58] Field of Search ................................. 600/546, 547, 600/587, 591, 595

[56] References Cited

U.S. PATENT DOCUMENTS

| | | | |
|---|---|---|---|
| 4,256,118 | 3/1981 | Nagel | 128/733 |
| 4,396,019 | 8/1983 | Perry, Jr. | 128/733 |
| 4,967,761 | 11/1990 | Nathanielsz | 128/733 |
| 5,154,177 | 10/1992 | Eisman et al. | 128/642 |
| 5,301,680 | 4/1994 | Rosenberg | 128/733 |
| 5,373,852 | 12/1994 | Harrison et al. | 128/733 |
| 5,397,344 | 3/1995 | Garfield et al. | 128/733 |

FOREIGN PATENT DOCUMENTS

| | | |
|---|---|---|
| 5601254 | 1/1988 | France . |
| 94/143373 | 7/1994 | WIPO . |

OTHER PUBLICATIONS

Margue, et al., "Uterine EHG Processing for Obstetrical Monitoring," *IEEE Transactions on Biomedical Engineering*, BME-33(12):1182-1186, Dec. 1986.

Pajntar, et al., "Electromyography of the Human Uterus," *IEEE Engineering in Medicine and Biology Society 10$^{th}$ Annual International Conference*, New Orleans, Louisiana, vol. 10, Nov. 1988.

Tepavac, et al., "A Portable 8 Channel Surface EMG Recording System," *Proceedings of the Annual International Conference of the IEEE Engineering in Medicine and Biology Society*, 14:1433-1434, Oct.-Nov. 1992.

(List continued on next page.)

Primary Examiner—Max Hinderburg
Attorney, Agent, or Firm—Rosenblatt & Redano P.C.

[57] ABSTRACT

A method and apparatus is presented for recording uterine electrical activity from the surface of the abdomen or vagina for the purpose of diagnosing contractile patterns of the uterus or abdominal muscles in pregnant and nonpregnant patients. The present invention provides data analysis techniques for analyzing electromyographic data measured from the surface of a patient to characterize uterine activity. The method and apparatus described include algorithms for the systematic analysis of electrical signals recorded from the abdominal surface. Such processing comprises integration of signals, frequency spectral analysis, 3-dimensional power density mesh plots, vector analysis, fast wavelet transform, and joint time-frequency characteristics. These techniques and apparatus are appropriate for use in a clinic or through communication lines for use as a remote or home uterine monitoring system. As such, uterine electrical activity may be measured at a remote location and processed at a central facility through on-line communications channels, such as a telephone line. The techniques and apparatus disclosed are also useful in predicting successful treatment for cases where either the uterus fails to develop forceful contractions at term or begins to contract pre-term.

23 Claims, 43 Drawing Sheets

OTHER PUBLICATIONS

Devedeux, et al., "Uterine Electromyography: A Critical Review," *Am. J. Obstet. Gynecol.* 169:1636–1653, 1993.

Wolfs, et al., "Electromyographic observations on the Human Uterus during Labour," *Acta Obstet. Gynecol. Scand.* (Suppl.) 90:1–62, 1979.

Garfield et al., "Control of Myometrial Contractility: Role and Regulation of Gap Junctions," *Oxford Rev. Reprod. Biol.* 10:436–490, 1988.

Dill, et al., "The Electrical Potentials of the Human Uterus in Labor, " *Am. J. Obstet. Gynecol.* 52–735–745, 1946.

Steer, "The Electrical Activity of the Human Uterus in Normal and Adnormal Labor," *Am. J. Obstet. Gynecol.* 68:867–890, 1954.

Halliday, et al. "Uterine Activity and Electrical Response," *J. Obstet. Gynaec. Brit. Emp.* 62:155–161, 1955.

Hon, et al., "Cutaneous and Uterine Electrical Potentials in Labor—an Experiment," *Obstet. Gynec.* 12 47–53, 1958.

Csapo, et al., Chapter 43, "Force of Labor," *Principles and Practices of Obstetrics and Perinatology*, Ed. L. Iffy, et al., Pub. John Wiley and Sons, 761–799, 1981.

Marshall, "Regulation of Activity in Uterine Smooth Muscle," *Physiol. Rev.* 42:213:227, 19625.

Garfield, Chapter 3, "Role of Cell–to–Cell Coupling in Control of Myometrial Contractility and Labor," *Control of Uterine Contractility*, Ed. R.E. Garfield, et al., CRC Press, 39–81, 1994.

Cody, "The Fast Wavelet Transform," *Dr. Dobb's Journal*, Apr. 1992.

Cody, "A Wavelet Analyzer," *Dr. Dobb's Journal*, Apr. 1993.

Cody, "The Wavelet Packet Transform," *Dr. Dobb's Journal*, Apr. 1994.

Phillipe, "Mechanisms Underlying Phasic Contractions of Pregnant Ray Myometrium Stimulated with Aluminum Fluoride," *Am. J. Obstet. Gynecol.* 173:981–990, Apr. 1994.

Garfield, "Mechanism Underlying Phasic Contraction of Pregnant Rat Myometrium Simulated By Aluminum Floride," *Am. J. Obstet. Gynecol.* 173:348–349, Jul. 1995.

Linzer, et al., "Incremental Diagonstic Yield of Loop Electrocardiographic Recorders in Unexplained Syncope," *Am. J. Cardio.* 66:214–219, Jul. 1990.

Trenkwalder, et al., "Usefulness of Simultaneous Ambulatory Electrocardiographic and Blood Pressure Monitoring in Detecting Myocardial Ischemia in Patients > 70 Years of Age with Systemic Hypertension, " *Am. J. Cardio.* 72:927–931, Oct. 1993.

Nagey, et al., "Randomized Comparison of Home Uterine Activity Monitoring and Routine Care in Patients Discharged After Treatment for Preterm Labor," Obstet, & Gynecol. 82:329–323, Sep. 1993.

"Home Uterine Activity Monitoring for Preterm Labor," *J. Am. Med. Assoc.* 270:369–376, Jul. 1993.

Survival Technology Inc., "The Cardio Beeper III," 1988.

Meditronic Cardiocare, "Arrhythmias Don't Keep Regular Hours, " 6 pgs., Jan. 1991.

Micro–Med, Inc., "Digi–Med Heart Performance Analyzer," 4 pgs., Jun. 1993.

Marquette Electronics, Inc., Mac Vu A Complete Electrocardiographic System, 12 pgs. 1992.

Marquette Electronics, Inc., "Mac 8 Resting ECG Analysis System, " 2pgs., 1993.

Marquette Electronics, Inc., "Cardiology Products," 18 pgs., 1992.

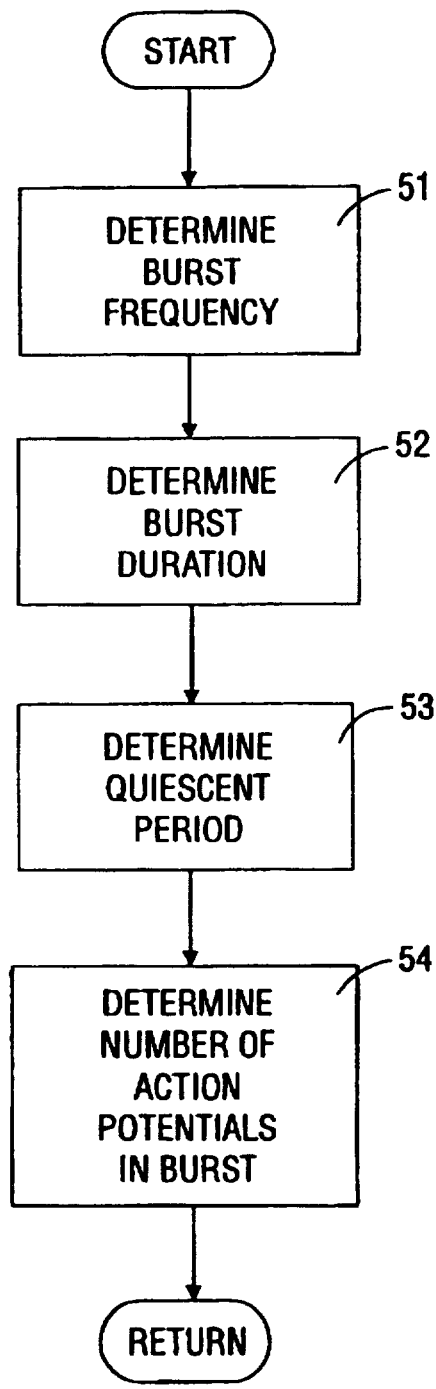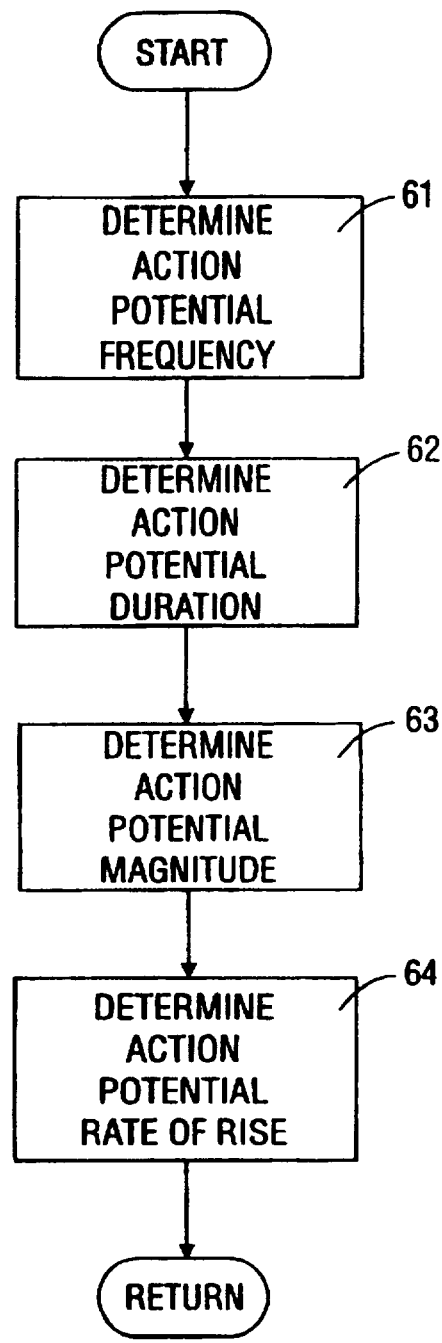
FIG. 4B
FIG. 4C

EMG power spectral density (PSD) curve.

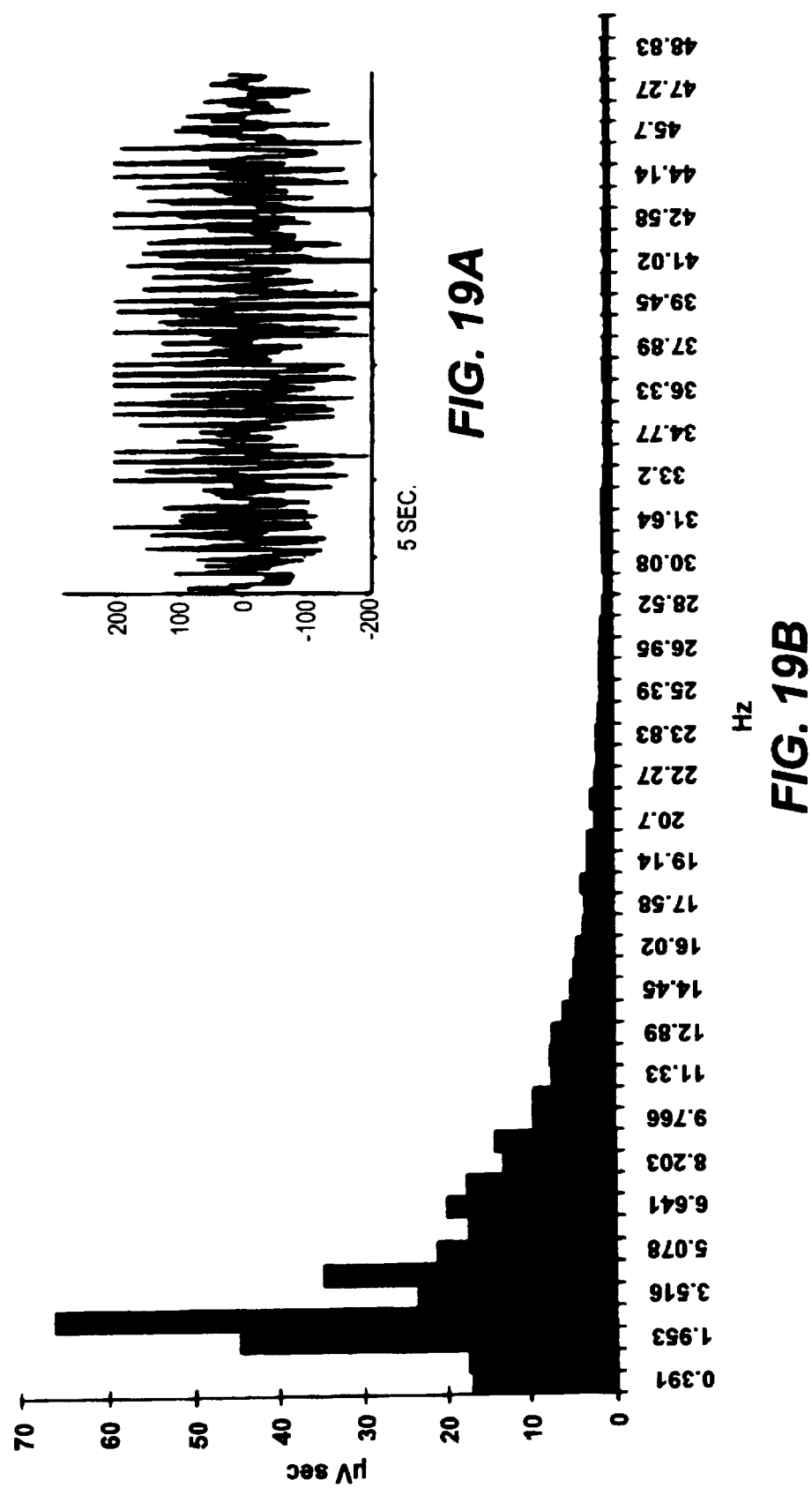

Potential vector P(t)

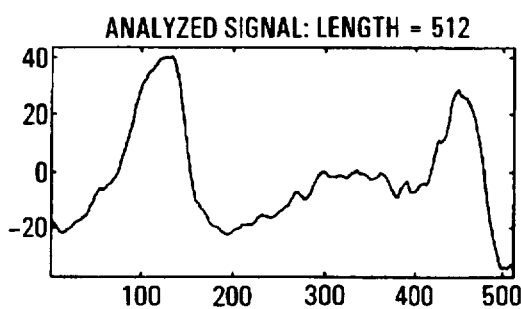
FIG. 32B(1)
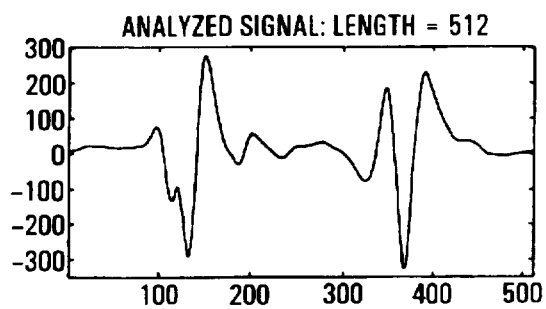
FIG. 32B(2)
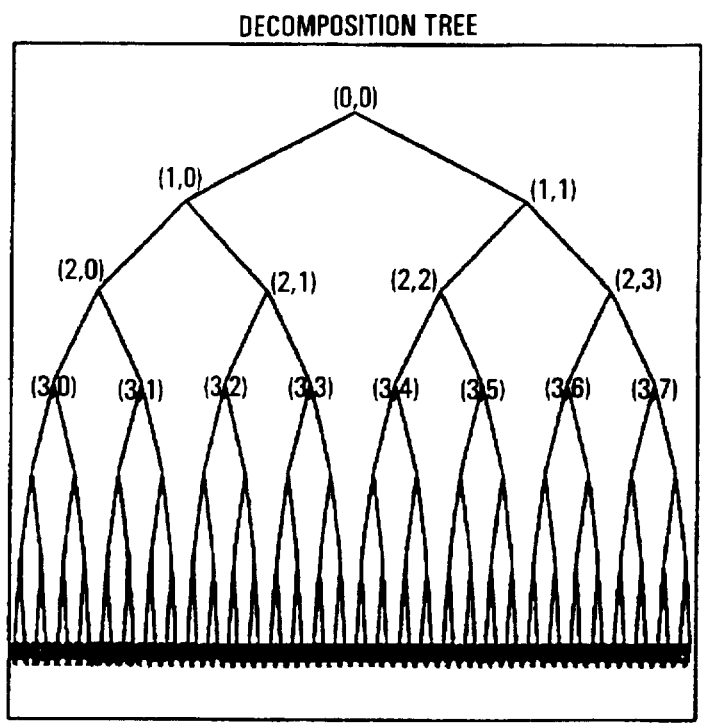
FIG. 32B(3)
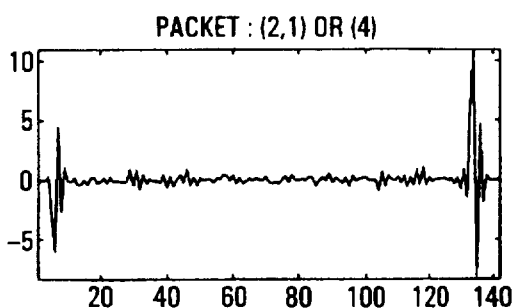
FIG. 32B(4)
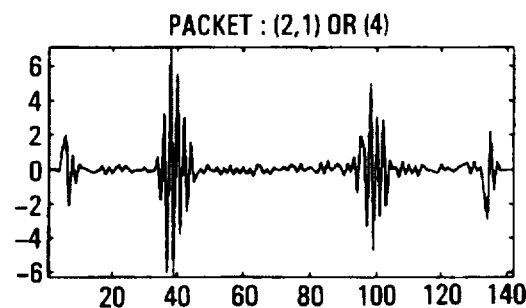
FIG. 32B(5)

METHOD AND APPARATUS FOR ANALYZING UTERINE ELECTRICAL ACTIVITY FROM SURFACE MEASUREMENTS FOR OBSTETRICAL DIAGNOSIS

RELATED APPLICATIONS

This is a continuation-in-partapplication of application Ser. No. 08/483,755, filed Jun. 7, 1995, now U.S. Pat. No. 5,623,939 which is a continuation-in-partapplication of application Ser. No. 08/246,214, filed May 19, 1994, which issued as U.S. Pat. No. 5,546,953 on Aug. 20, 1996.

BACKGROUND OF THE INVENTION

This invention relates to a method and apparatus for recording and analyzing uterine or vaginal electrical activity. More specifically, the invention relates to a method and apparatus useful for determining the contractility of the uterus or abdominal muscles by recording spontaneous, mechanically or electrically stimulated, or drug-evoked electrical activity of the myometrium of the uterus from the abdominal, cervical or vaginal surface. The invention further relates to the analysis of surface electromyographic data corresponding to uterine or abdominal muscle electrical activity for obstetrical diagnosis.

Presently there is no objective manner with which to evaluate the contractility of the uterus. This is true either in nonpregnant patients where hypercontractility is associated with dysmenorrhea or in pregnant patients where the uterus is sometimes active prior to term. Normally the uterus is quiescent in nonpregnant women and during most of pregnancy. However, at the end of pregnancy the myometrium undergoes a series of changes that lead to synchronous, rhythmic uterine contractions (labor). The diagnosis of labor is the most significant problem faced by obstetricians. In addition, preterm labor, which occurs in about 10% of pregnant patients, is difficult to diagnose. Frequently term or preterm labor require adjuvant therapy to either stimulate or inhibit contractility of the uterus.

Since there is some minor spontaneous uterine activity at all times during pregnancy, it is often not possible to distinguish between this physiological activity and term or preterm labor. The state of the cervix is commonly used as a predictor of labor. However, the softening of the cervix may occur relatively late in labor. In addition, labor and changes in the cervix can occur independently. Alternatively, the frequency of contractions is used to diagnose labor, sometimes recorded with a tocodynamometer. However, these methods give only crude subjective estimates of uterine contractility.

The uterus does not contract vigorously throughout most of pregnancy and this provides a tranquil environment for the growing fetus. At term the uterus normally begins to contract forcefully in a phasic manner (labor) to expel the fetus. Contractions of the uterus are directly proportional to the underlying electrical activity of the muscle. The frequency, duration and magnitude of a uterine contraction are directly proportional respectively to frequency of bursts of action potentials, the duration of a burst of action potentials, and the propagation (also referred to as conduction) of action potentials over the uterus and the recruitment of muscle cells. A similar situation exists in heart muscle although heart and uterine muscle are different with respect to structure and configuration of the action potentials. The action potentials are accompanied by the influx of calcium into the muscle cells to activate the contractile apparatus. Between bursts of action potentials, the uterus relaxes and recovers. The relaxation phase in uterus, although perhaps not as critical as in the heart where refilling must occur, is still very important in providing a respite for both the muscle and the fetus.

Thus, by recording uterine electrical activity one can assess the contractility of the myometrium. Technology has been used to record cardiac electrical activity to determine the normal or abnormal function of the heart. Electrical events in muscle reflect the opening and closing of ion channels. In the case of the electrocardiograph (ECG), the ability to diagnose molecular defects, at the level of the ion channels themselves, has been clearly demonstrated. The ECG also allows you to study the conduction pathway in the heart, which produces a highly stereotyped spatial pattern of activity. The uterus may lack such a pathway; none has ever been identified. Little is presently known about the spatial organization of excitation in the uterus, although the importance of low-resistance pathways between adjacent cells is known to be crucial. The present invention provides an apparatus for mapping the electrical activity of the uterus. It is known that the uterus is more active during the night than during the day, and this pattern may grow even more pronounced as labor becomes imminent. The present invention also offers the opportunity to assess the predictive value of diurnal variations in uterine activity in relation to the onset of labor.

During labor, the patient may actively contribute to the labor process by consciously contractingher abdominal muscles. Such muscle contractions produce striated muscles in the patient's abdominal wall, which can be detected from an examination of the underlying electrical activity of the muscle. The present invention is also directed toward distinguishing electrical activity indicative of abdominal muscle contraction, from that indicative of myometrial contractions.

Many studies have previously recorded uterine myometrial electrical activity using electromyography (EMG) where electrodes are placed directly on the uterus. These studies show that the myometrium generates little electrical activity prior to labor but activity increases tremendously during labor reflecting the mechanical events. Studies of interest are demonstrated in publications by Csapo, Chapter 43, "Force of Labor," *Principles and Practice of Obstetrics and Perinatology,* Ed. by L. Iffy and H. A. Kaminetzky Publishing, John Wiley and Sons 761–799, 1981; Garfield et al., "Control of Myometrial Contractility: Role and Regulation of Gap Junctions," Oxford Rev. Reprod. Biol. 10:436–490; 1988; Wolfs and Van Leeuwen, "Electromyography observations on the human uterus during labor," Acta Obstet. Gynecol. Scand. |Suppl.| 90:1–62, 1979; and more recently by Devedeux et al., "Uterine Electromyogiaphy: A Critical Review," Am J. Obstet. Gynecol. 169:1636–1653, 1993. One may measure and use uterine EMG activity by direct contact with the uterus to predict normal and abnormal uterine contractions. However, it is not practical to place electrodes directly on the uterus. To do this under the present level of understanding one must surgically implant electrodes on the uterine surface or introduce a catheter electrode through the vaginal canal and puncture the fetal membranes.

It would be desirable to record uterine EMG activity from the abdominal or vaginal surface. However, previous studies of electrical activity of the uterus recorded with electrodes placed on the abdominal surface have failed to record bursts of action potentials from the uterus and generally show no association of uterine electrical activity with contractility.

Studies of interest are included in the above-noted publications by Wolfs and Van Leeuwen, and by Devedeux et al. Wolfs and Van Leeuwen summarized all studies prior to 1979 and concluded that "it has never been clearly shown that the potential fluctuations obtained by means of electrodes attached to the abdominal wall, do indeed represent the electrical activity of the uterus." (Page 7.) Similarly, Devedeux et al state that abdominal monitoring of uterine electrical activity "requires further investigation." (Page 1649.)

Part of the difficulty in interpretation of electrical activity recorded from the uterus lies in the fact many investigators, including Wolfs and Van Leeuwen and Devedeux et al. have failed to recognize that action potentials drive the uterus to contract. Action potentials are not responsible for contraction of some smooth muscle tissues such as airway muscle and some vascular muscles and therefore many researchers confound the uterus with other smooth muscle tissues. Thus, many of these studies have attempted to correlate electrical activity with mechanical contractions in order to show that electrical activity is responsible for contractions. However, no study has measured uterine and surface EMG simultaneously and correlated these to contractions. Furthermore, it is now clear (from publications by Marshall, "Regulation of Activity in Uterine Smooth Muscle," Physiol. Rev. 42:213–227, 1962; Csapo, Chapter 43, "Force of Labor," *Principles and Practice of Obstetrics and Perinatology*, Ed. by L. Iffy and H. A. Kaminetsky, John Wiley & Sons, 761–799, 1981; Garfield et al., "Control of Myometrial Contractility: Role and Regulation of Gap Junctions," Oxford Rev. Reprod. Biol. 10:436–490, 1988; Garfield, Chapter 3, "Role of cell-to-cell Coupling in Control of Myometrial Contractility and Labor," *Control of Uterine Contractility*, Ed. by R. E. Garfield and T. Tabb, CRC Press, 39–81, 1994), that action potentials activate the uterus to contract and that by measuring uterine electrical activity one can indirectly estimate contractility, although none of these studies provide a detailed explanation of how to analyze uterine electrical activity in order to indirectly estimate contractility and to distinguish contractility from other physical phenomena, such as abdominal muscle contraction.

SUMMARY OF THE INVENTION

The present invention presents a method and apparatus for recording and analyzing uterine electrical activity from the surface of the abdomen or vagina for the purpose of diagnosing contractile patterns of the uterus in pregnant and nonpregnant patients. The present invention provides data analysis techniques for analyzing electromyographic data measured from the surface of a patient to characterize uterine and abdominal muscle activity.

A feature of the present invention is the measurement in vivo of the electrical and therefore the mechanical activity of uterine and abdominal muscle tissue, to produce a more quantitative, comprehensive and analytical framework of the tissue by transferring information from the tissue to a computer memory for automatic analysis and for display on a monitor for assessment by an attending physician or other party interested in monitoring the tissue.

The present invention is applicable to a wide range of obstetrical, gynecological and other conditions. One such application is defining the state of the uterus during term and preterm labor. Another application is monitoring the non-pregnant uterus for indication of conditions such as infertility and uterine pathology. The method and apparatus are also valuable for use in connection with other tissues other than the uterus such as tests of bladder function during urination or similarly, evaluation of the bowels during defecation.

The method and apparatus of the present invention includes algorithms for the systematic analysis of electrical signals recorded from the abdominal surface. Such processing comprises integration of signals, frequency analysis, 3-dimensional mesh plots, vector analysis, fast wavelet transform (continuous and discrete) and wavelet packet analysis, and joint time-frequency characteristics. These techniques and apparatus are appropriate for use in the a clinic or through communication lines for use as a remote or "home" uterine monitoring unit. As such, uterine electrical activity may be measured at a remote location and stored in compressed form. Data from these measurements may be recorded for later processing at a central or remote facility, or it could be processed on-line over communications lines, such as telephone lines or radio frequencies. Further, the present invention can be used to predict successful treatment for cases where either the uterus fails to develop forceful contractions at term or begins to contract pre-term.

In accordance with an embodiment of the invention, recording electrodes capable of measuring action potentials are placed at various points on the abdominal surface of a pregnant patient. An amplifier is electrically coupled to receive an analog input from the electrodes, and to amplify it. An analog to digital converter (ADC) may also be electrically coupled to receive an amplified analog input from the amplifier indicative of bioelectrical potentials measured by the electrodes.

Electromyographic signals are transmitted through the electrodes at a sampling frequency of between 0.5 Hz to 1 kHz for a duration of time sufficient to record at least one (1) burst of action potentials. These signals are amplified by an amplifier. Typically, the sampling frequency is about 100 Hz and a minimum of five (5) bursts are measured. The signals may be further processed using filters before or after storage to isolate signal components. A memory (or storage device) comprising sufficient storage capacity to store data resulting from a sampling of electromyographic signals at a sampling frequency of at least 100 Hz, for a duration of time sufficient to record at least five (5) bursts of action potentials is coupled to receive an input from the amplifier, indicative of electrical signals received by the amplifier. Said electromyographic signals are stored in the memory. The signals may then be filtered in order to identify signals in one or more frequency ranges of interest. The values of these ranges are dependent upon the species of patient under evaluation. For instance, in human beings, the primary frequency range of interest for the identification of uterine contractility from surface abdominal signals is .01 Hz–10 Hz. The computer contains software to facilitate this analysis of the signals.

The above described electrodes may alternatively be placed on the vaginal wall or pericervical surfaces. Probe electrodes or needle electrodes are particularly suited for this application. Probe electrodes are available from Millar Instruments of Houston, Tex. This may be particularly useful for monitoring electrical activity in early pregnancy and in nonpregnant women where the uterus is small and not likely to produce strong EMG signals that propagate to the abdominal surface, but are transferred down the reproductive tract to the vagina.

In particular, the present invention contemplates a method of analyzing surface electromyographic data to characterize uterine or abdominal muscle activity, comprising applying action potential measuring electrodes to an abdominal surface of a patient; measuring electromyographic signals produced by the electrodes; analyzing frequency components of the electromyographic signals; and characterizing uterine or abdominal muscle activity of the patient based on the analysis of frequency components. Ideally, the analysis of uterine activity indicating parameters is performed for data from at least five (5) bursts of action potentials within the stored electromyographic signals. The burst analysis may include determining the frequency, duration, amplitude, number of action potentials per burst, activity per unit time of interest, and power density spectrum of at least five (5) bursts of action potentials and the frequency, duration, and amplitude of a plurality of action potentials in one or more of these bursts. As a further embodiment, the method also includes predicting treatment for the patient based on the characterization of uterine activity, in particular this treatment may be pharmacologically inducing or inhibiting labor in the patient.

The burst of action potentials may be analyzed using wavelet or Cepstrum Analysis, as described in Akay, Chapter 6, "Cepstrum Analysis," *Biomedical Signal Processing*, Academic Press (1994). The electromyographic signals may also be analyzed using non-linear dynamics, or chaotic analysis, as described in Molnar, et al., "Correlation Dimension of Changes Accompanying the Occurrence of the Mismatch Negativity and the P3 Event—Related Potential Component," Electroencephalography and Clinical Neurophysiology, 95 (1995), pp. 118–26; *Elbert, et al.,* "Chaos and Physiology: Deterministic Chaos in Excitable Cell Assemblies." Physiology Reviews, Vol. 74, No. 1, Jan. 19, 1994; and *Skinner, et al.* "The Point Correlation Dimension Performance with Non-Stationary Surrogate Data and Noise." Integrative Physiological and Behavior Science, Vol. 28, No. 3, pp. 217–34 (Sept. 1994). The electromyographic signals may also be analyzed using a myometrial index, comprising power density spectrum and frequency data. The distribution of intervals between successive action potentials may be characterized as an indicator of aberrant activity.

The invention also contemplates the stimulation of the vagina of the patient while the electromyographic signals are being stored. This stimulation permits the assessment from the stored electromyographic signals for the phenomenon of conduction, and permits the diagnosis of labor as a function of the signals. The stimulation of the vagina may either be electrical, mechanical or pharmacological, for example through the infusion of oxytocin to the patient.

Other further embodiments contemplate isolating high frequency components (F2) within the electromyographic signals; isolating a fast wave component (FW) within the high frequency components (F2); determining a low-frequency ($FW_L$) domain, including low-frequency components within the fast wave component (FW), and a high-frequency ($FW_H$) domain, including high-frequency components within the fast wave component (FW); and determining a relationship between the low-frequency ($FW_L$) domain and the high-frequency ($FW_H$) domain indicative of an obstetrical diagnosis. This relationship can be indicative of pre-term or term uterine activity.

Other embodiments of the present invention contemplate analyzing the frequency ranges of interest using wavelet analysis methods to decorrelate the signals, displaying the signal components by subband, and comparing the energy levels contained in particular subbands versus time of pregnancy. The wavelet transform or wavelet packet analysis may be used to generate various measures (such as amplitudes and ratios) of the wavelet maxima, skeleton, or energy content within particular subbands. The resulting decomposition(s) of the signal may be used in denoising by thresholding, wavelet shrinkage, and comparable approaches. The signal may be compressed with high efficiency before storage by discarding the smallest wavelet coefficients.

An alternative embodiment of the present invention, contemplates a method of analyzing surface electromyographic data to characterize uterine activity, comprising applying multiple pairs of action potential measuring electrodes to a surface of a patient; measuring electromyographic signals produced by the electrodes; analyzing the electromyographic signals; determining potential vector characteristics of the electromyographic signals to identify direction and rate of propagation of uterine electrical activity; and characterizing uterine activity of the patient based on the potential vector characteristics. This potential vector can be indicative of a obstetrical diagnosis, including pre-term or abnormal term uterine activity.

The apparatus of the present invention includes at least one electrode (unipolar, bipolar, etc) that is applicable to the abdominal, cervical or vaginal surface of the patient under analysis, an amplifier electrically coupled to the electrode to receive and amplify a signal indicative of action potentials measured by the electrode; an analog-to-digital converter, that is electrically coupled to receive an analog input from the amplifier indicative of action potentials measured by the electrode, and that converts electromyographic signals produced by the electrodes into digitized data which are indicative of electromyographic signals, a memory for storing the digitized signals, and comprising sufficient storage capacity to store data resulting from a sampling of electromyographic signals at a sampling frequency of at least 100 Hz. for a duration of time sufficient to record at least five (5) bursts of action potentials, a filtering device capable of segregating and identifying electromyographic signals, including action potentials, in preselected frequency ranges, and a programmed computer for analyzing the stored digitized signals and for providing a characterization of uterine activity. The computer comprises an expert system programmed to analyze the frequency, duration, amplitude, and power density spectrum o connected to the f action potential bursts and individual action potentials. The expert system is further capable of characterizing uterine activity and of identifying abdominal muscle contractions, based upon this analysis.

The expert system may comprise algorithms needed to perform a Cepstrum analysis, wavelet analysis, chaotic analysis, or myometrial analysis of the action potentials. The expert system may also be capable of identifying abdominal muscle contraction. The expert system may also be capable of evaluating the trend of uterine activity over the course of labor, encompassing many hours, to determine whether labor is progressing, and alerting the physician to the possible diagnosis of failure-to-progress and the need to treat by pharmacological, surgical, or electrical means. The expert system may be capable of assessing other clinical data in combination with the EMG data.

An alternative embodiment contemplated by the present invention is an apparatus for recording and analyzing uterine electrical activity from the abdominal surface, comprising at least one action potential measuring electrode applicable to an abdominal surface of a patient under analysis; an analog-to-digital converter, connected to the at least one electrode, for converting electromyographic signals produced by the electrode into digitized data indicative of the electromyographic signals; a memory for storing the digitized signals; and a programmed computer for analyzing frequency components of the stored digitized electromyographic signals, and for providing an indication of uterine electrical activity of the patient under analysis as a function of the stored digitized signals. A still further embodiment contemplates an apparatus wherein the programmed computer is used further for determining power density spectral characteristics of the frequency components of the electromyographic signals.

The present invention further contemplates an apparatus in the form of a remote uterine monitoring system for analyzing surface electromyographic data to characterize uterine activity, comprising a remote uterine monitor and a central programmed computer in communication with the remote uterine monitor for analyzing stored digitized electromyographic signals, and for providing an indication of uterine electrical activity of the patient under analysis as a function of the stored digitized signals. The remote uterine monitor includes at least one action potential measuring electrode applicable to an abdominal surface of a patient under analysis; and a remote analog-to-digital converter, connected to the at least one electrode, for converting electromyographic signals produced by the electrode into digitized data indicative of the electromyographic signals.

In a further embodiment, the remote uterine monitor and the central programmed computer communicate on-line through a telephone line. In a still further embodiment, the remote uterine monitoring system also includes a remote storage device for recording the digitized electromyographic signal data, and wherein the central programmed computer communicates with the remote uterine monitor off-line through the remote storage device.

These and other features and advantages of the present invention will become apparent to those of ordinary skill in this technology with reference to the following detailed description and appended drawings.

BRIEF DESCRIPTION OF THE DRAWINGS

Various features and attendant advantages of the present invention will be more fully appreciated as the invention becomes better understood when considered in conjunction with the accompanying drawings, in which like referenced characters designate the same or similar parts throughout the several views, and wherein:

FIGS. 4A–4G are flow charts of the method of the present invention.

FIGS. 19A–19B are a burst of action potentials recorded from a rat abdominal surface, and a spectral analysis of this burst, respectively.

FIG. 32B is an illustration of wavelet packet analysis.

DETAILED DESCRIPTION OF THE PREFERRED EMBODIMENTS

Figure 1A:
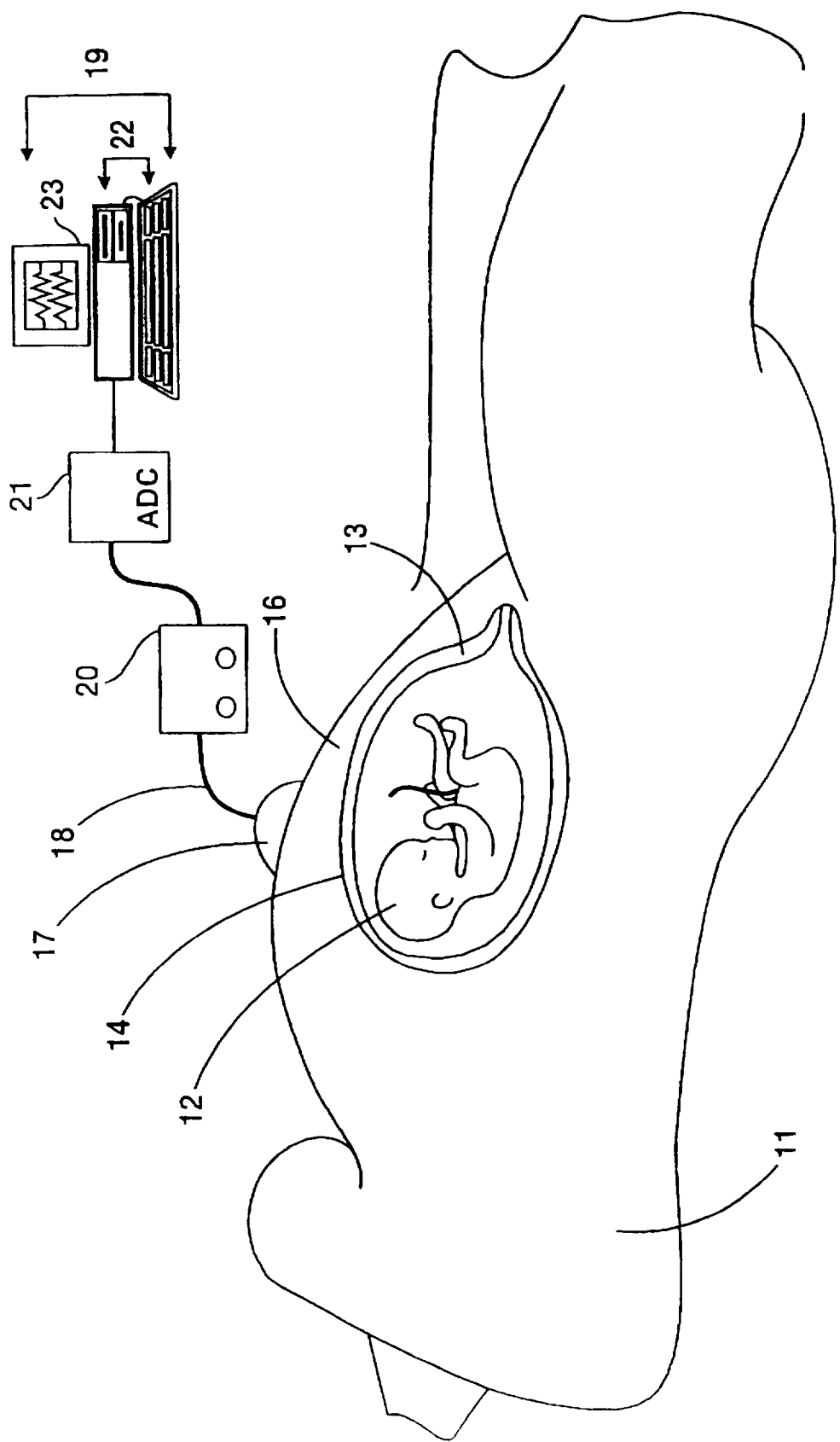
FIG. 1A is a side view, partially in phantom, showing the recording apparatus in accordance to the present invention attached to the abdominal wall of a pregnant patient.

Referring now to FIG. 1A, there is shown schematically a pregnant patient 11 with a fetus 12 retained within the uterus 13. The uterine wall 14 is primarily configured of muscle tissue and is disposed proximate to the abdominal wall 16 of the patient 11. In accordance with the principles of the present invention, electrodes 17 are placed on the exterior of the patient 11 on the abdominal wall 16. In another embodiment, electrode 16 may be placed on the vaginal surface of the patient. The electrodes 17 have leads 18 that are connected to a recording apparatus 19 including an amplifier 20, analog-to-digital converter (ADC) 21, computer 22 and monitor 23. In a preferred embodiment, amplifier 20 is used to amplify the signal received from electrode 17. The ADC, computer and monitor may be replaced or augmented by other output indicators, such as chart recorders or indicator lamps or audio monitors.

Figure 1B:
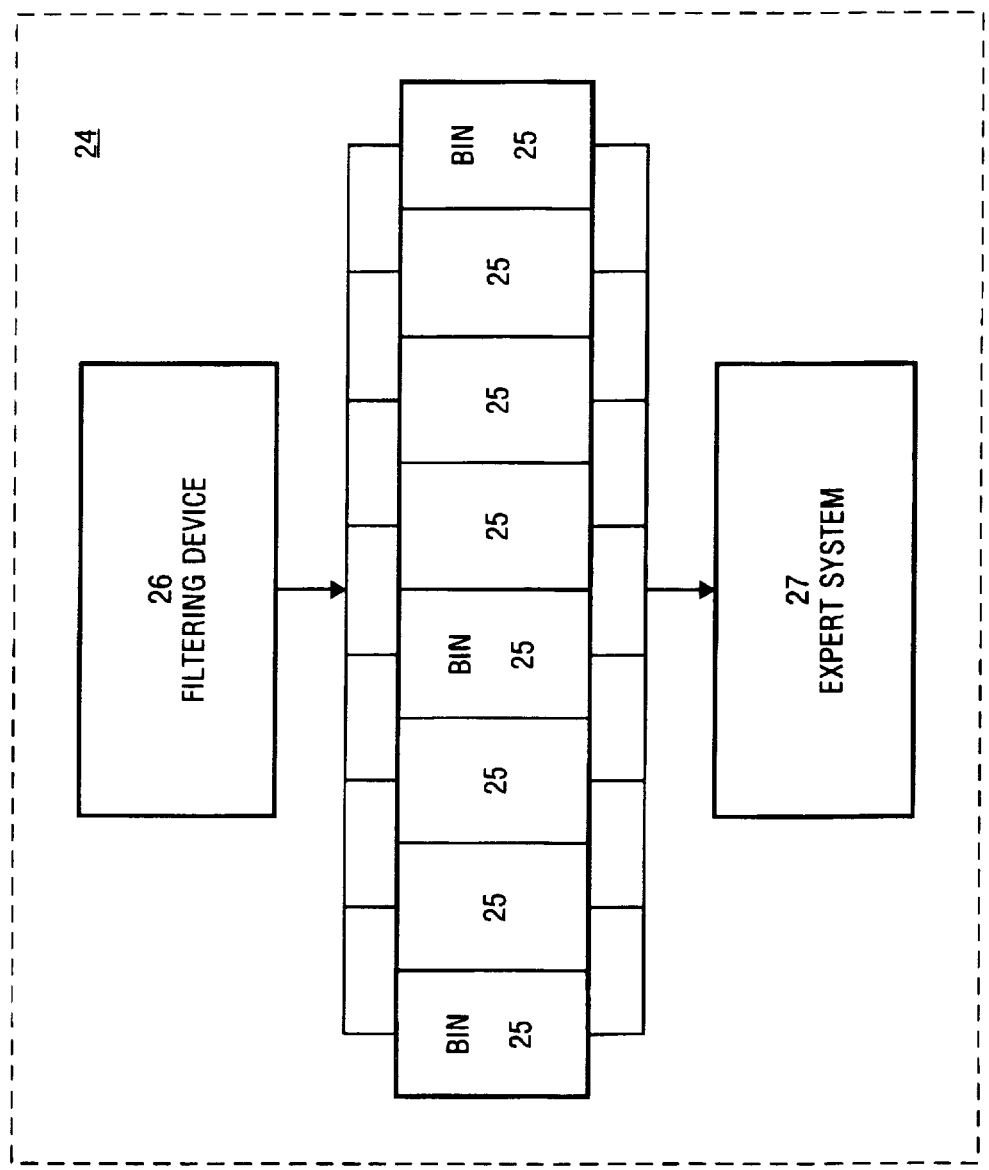
FIG. 1B is a block diagram of the signal filtering, memory, and expert system of the present invention.

In accordance with the principles of the present invention, the uterus 13 of the pregnant patient 11 is monitored for electrical activity from signals detected on the surface of the abdomen. In a preferred embodiment, the signals (EMG) are amplified by amplifier 20, digitized by ADC 21, and displayed on a monitor 23. The signals are also stored in the memory 24 of computer 22 for analysis of the frequency duration and other characteristics of the action potentials. As shown in FIG. 1B, memory 24 comprises filtering device 26 capable of segregating and identifying electromyographic signals including action potentials in predetermined frequency ranges, a multiplicity of bins 25 for storing eleccctromyographics signals in discrete predetermined frequency ranges, and expert system 27 programmed to analyze the frequency, duration, amplitude and power density spectrum of action potential bursts and individual action potentials and further capable of characterizing uterine activity and identifying muscle contractions, based upon such analysis. In an alternative embodiment, functions performed by filtering device 26 are carried out by software.

In a preferred embodiment, expert system 27 is also capable of determining the mean frequency, starting frequency, and ending frequency of a plurality of action potentials. In another preferred embodiment, the expert system 27 is also capable of identifying abdominal muscle contractions. In another preferred embodiment, the expert system 27 is also capable of evaluating long-term trends in uterine activity as indicating the progression of labor. In another embodiment, the expert system may compare records from the same patient taken at different times during her pregnancy and predict the onset of labor at term. In another preferred embodiment, the expert system 27 is capable of using clinical information in combination with electromyographic data to suggest possible diagnoses.

In accordance with one embodiment of the present invention, ADC 21 may be, for example, a Data-Pac II A/D board, available from Run Technologies, or a MacLab A/D board, available from MacLab Division of AD Instruments. Amplifier 20 may be, for example, a Grass polygraph recorder, Mode #7D with DC amplifiers, available from Grass Instruments, or a Gould amplifier and recorder Model TA240, available from Gould Instruments, or a MacLab amplifier for Macintosh computers, available from the MacLab Division of AD instruments. Computer 22 with monitor 23 may be, for example, any IBM PC compatible computer, preferably with a 486-type (or better) microprocessor, twelve (12) megabytes of RAM, and a 500 megabyte hard drive and a VGA (or better) display, or a Macintosh IIci computer with display, or a Macintosh Powerbook lap-top computer, or an IBM lap-top computer, or any other equivalent computer and monitor. Computer 22 may also include several types of long-term storage devices, including recordable CD-ROM, tape, or high-capacity disks or removable cartridges.

Electrodes 17 may be, for example, stainless steel clips or cups, for example, various models available from Hewlett-Packard, silver or platinum clips or cups, or they may be a Bard catheter with electrodes for vaginal recording, available from Bard Reproductive Sciences.

Although specific examples have been given for the various hardware components shown in FIG. 1A–1B, it will be understood that different hardware components may be used, without departing from the spirit and scope of the present invention. For example, some embodiments of the present invention comprising the more complex data analysis schemes may require a Pentium® or comparable microprocessor and at least 64 Mbytes of RAM.

Figure 2:
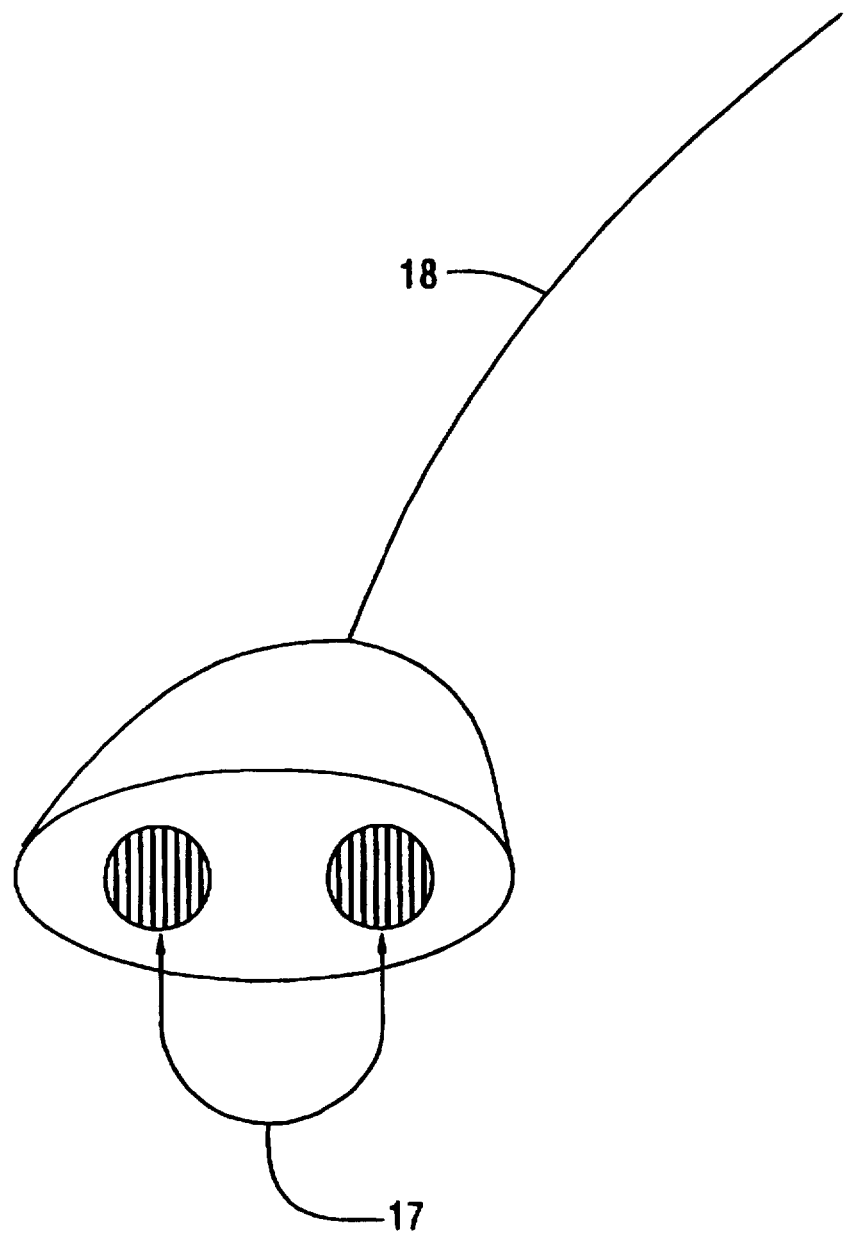
FIG. 2 is an enlarged view of the surface electrodes used in FIG. 1 in accordance with the present invention.

Referring also to FIG. 2, an enlarged side view of the electrodes 17 is shown, that are used in contact with a patient's abdominal wall. The electrodes 17 are bipolar (or tripolar) comprised of silver or platinum, and are spaced about 1 cm apart. Leads 18 from the electrodes 17 are connected to amplifier 20.

The amplifier 20 includes controls for amplifying or attenuating the signals and also filters for elimination of some of the high or low frequency noise. The amplifier is, for example, a battery powered ac/dc differential amplifier with the following approximate specifications:

| Gain, AC and DC | ×100, ×1,000 & ×10,000 |
| --- | --- |
| Input resistance | $10^{12}$ ohms typical |
| Leakage current | 50 pA typical |
| Common Mode Rejection | 100,000:1 min @ 60 Hz |
| Noise, input shorted | 10 µV p—p, 1 Hz–10 kHz |
| Low Freq filter settings | 0.01, 0.1, 1.0, 10, 300 Hz |
| High Freq filter settings | 0.1, 1.0, 3.0, 10 kHz |
| Output resistance | 220 ohms |

In another embodiment, amplifier 20 may carry out several stages of signal processing and analysis, including action potential detection and power spectral analysis, by analog hardware implementations of algorithms.

The computer 22 and monitor 23 may be of conventional PC design with software and hardware to digitize the signals. The computer 22 is programmed with software to enable computer 22 to acquire, store, display and analyze the signals. This software may comprise an integrated general-purpose or customized software suite such as DataPac or MacLab or LabView (National Instruments). Additional software with extended signal-processing or statistical analysis capabilities may also be utilized, such as MatLab (The Math Works, Inc.) or S-Plus with S+ Wavelets (MathSoft). The operation of computer 22, in accordance with the present invention, is discussed below in detail with reference to the flow charts of FIGS. 4A–4E.

Figure 3:
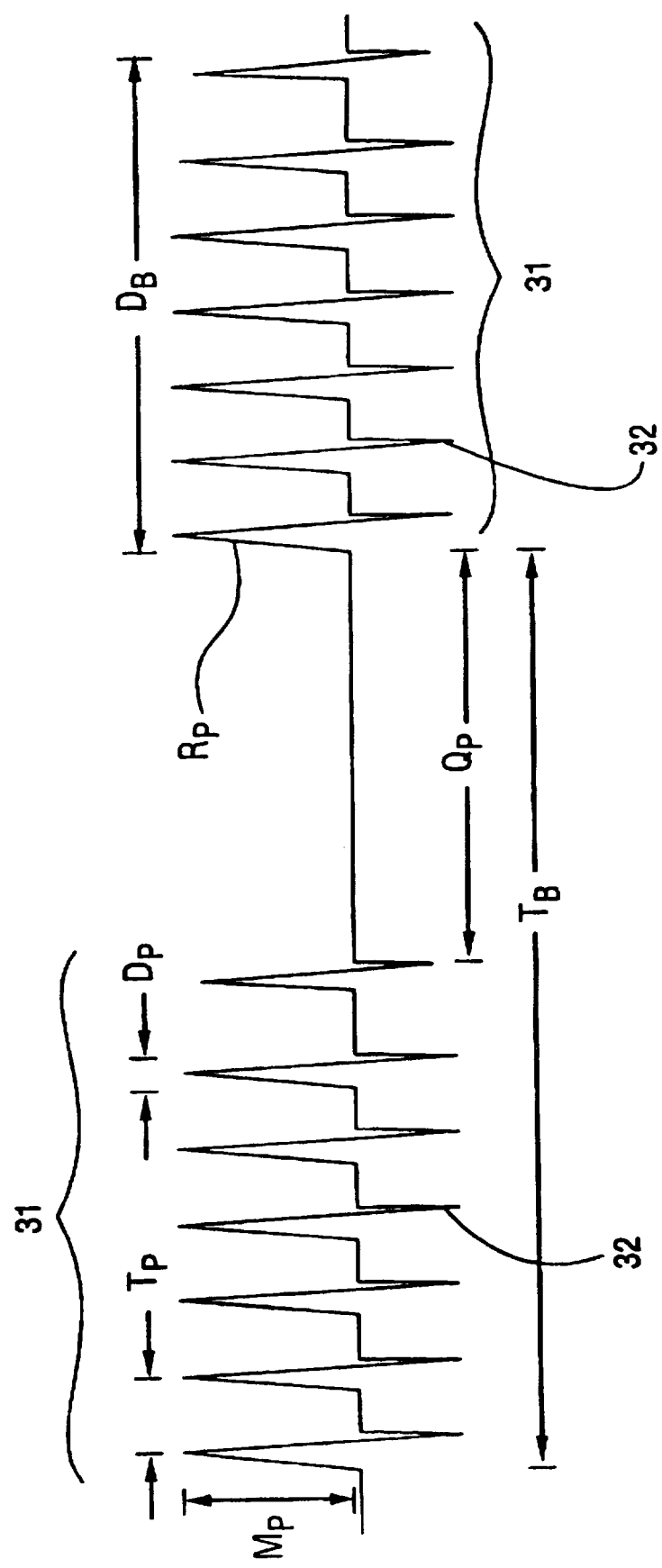
FIG. 3 is an illustration of two bursts of action potentials of an EMG signal.

Referring also to FIG. 3, shown are typical bursts 31 that are comprised of multiple action potentials 32 recorded from the surface of a patient's abdomen 16 from electrical activity of the uterus 13 and that correspond to the overlying contractility of the uterus 13 (see also, FIG. 1). The initial identification of action potential and burst events may be partially or fully automated, where action potentials are identified by techniques such as peak detection or wavelet analysis implemented in either software or hardware, and the putative identification indicated on a monitor display where it may be optionally reviewed by an operator for acceptability prior to further analysis. Thresholds and other selection criteria may be adjusted manually. A need for further preprocessing or optimization of the recording configuration may also be identified at this stage either by the operator or by automatic quality-control routines. Various parameters are measured from the bursts and from the action potentials, and are used for diagnostic purposes in accordance with the present invention. These parameters include: Frequency of bursts($1/T_B$), number of bursts per unit time ($N_B$), duration of bursts ($D_B$), quiescent periods between bursts ($Q_P$), number of action potentials in each burst ($N_P$), and characteristics of the action potentials including, frequency of action potentials ($1/T_P$), duration of action potentials ($D_P$), magnitude of action potentials ($M_P$), rate of rise of action potentials ($R_P$, i.e. slope of the depolarization of action potentials, dv/dt). The parameters measured during the burst may compared with their counterparts during the interval between bursts as a further indicator of contractility and relaxation.

The analysis of the present invention is both real-time and predictive. In the real-time analysis, the action potential indicating parameters are analyzed in order to assess the present or real-time status of the patient's condition. In the predictive analysis, a series of action potential indicating parameters are analyzed as a function of time in order to predict uterine contractility, based upon one or more identified trends of examined uterine activity indicating parameters.

Referring now to FIGS. 4A–4G, presented are flow charts depicting the operation of the apparatus of FIG. 1, in accordance with the present invention. In practice, the flow charts of FIGS. 4A–4G are embodied in a computer program or expert system used to control the operation of computer 22 of FIG. 1. Beginning in step 41, computer 22 acquires EMG signals produced by electrodes 17, which have been amplified by amplifier 20 and digitized by ADC 21. In step 42, digitized versions of the EMG signals are stored in the memory of computer 22.

Control then passes to step 43 where the stored EMG data is analyzed to assess parameters reflecting groups or bursts of action potentials present in the stored EMG signal. These analysis steps are shown in more detail with reference to FIG. 4B. Control then passes to block 44 wherein the stored EMG signal is analyzed to determine parameters characterizing the individual action potentials within the stored EMG signal. The details of the action potential analysis is shown in FIG. 4C.

Control then passes to step 46 where probability analysis is conducted on the EMG signal characteristics determined in steps 43 and 44. The details of this probability analysis are shown with reference to FIG. 4D.

Control then passes to decision block 47 where, based upon the probability analysis performed in step 46, it is determined whether the stored EMG signal reflects normal or abnormal uterine progression. The details of this diagnostic decision are shown below with reference to FIG. 4E. If normal progression is concluded by decision block 47, control passes to block 48 wherein the normal progression is characterized as either non-labor, pre-labor or labor based upon characteristics of the bursts and action potentials. If abnormality is concluded by decision block 47, control passes to block 49 where the abnormality is characterized as preterm labor, dystocia or other abnormalities based upon characteristics of abnormal bursts and action potentials.

Figure 4A:
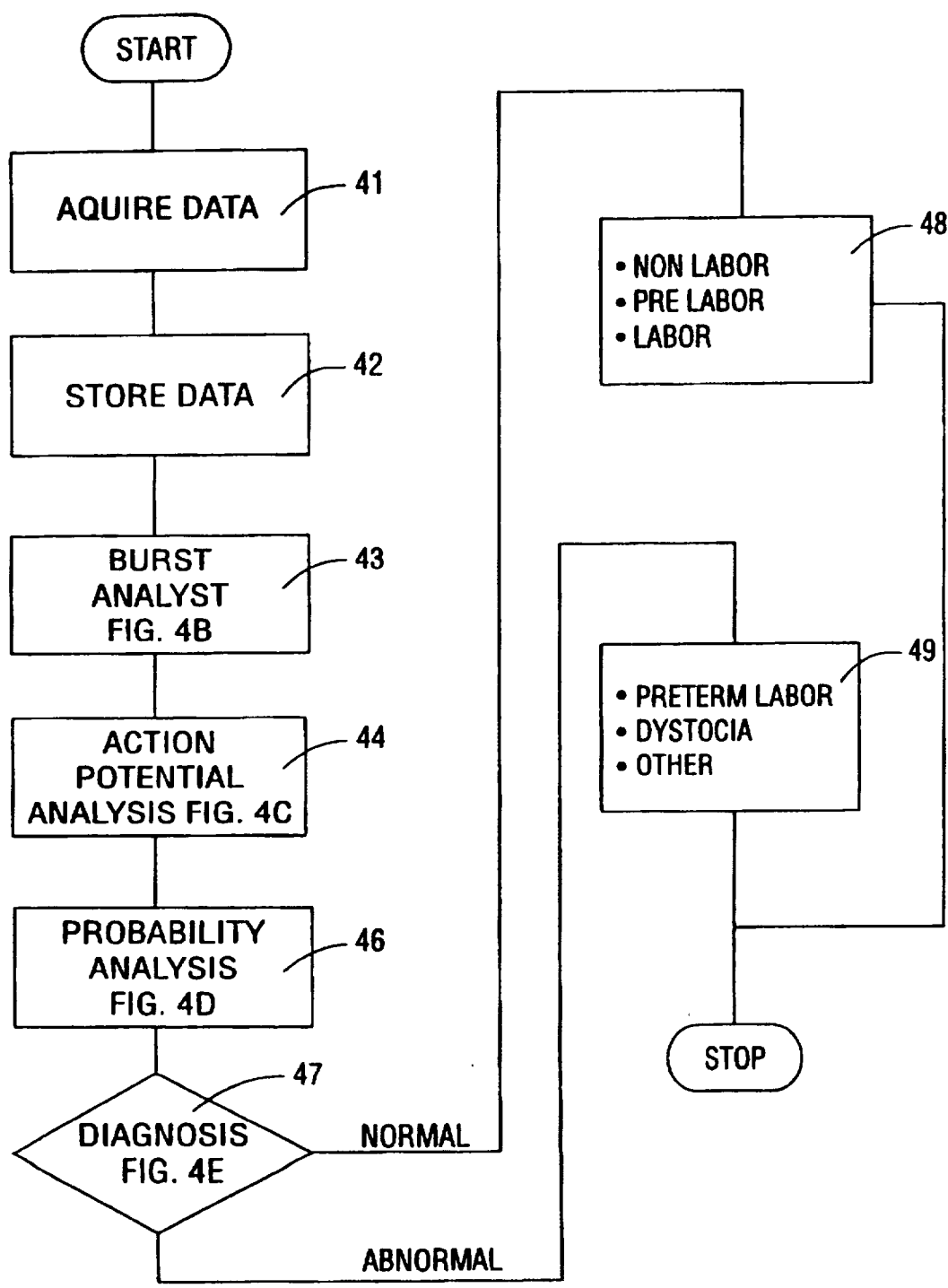

Referring now to FIGS. 3 and 4B, the details of the analysis of burst activity conducted within block 43 of FIG. 4A are presented. Beginning in step 51, the frequency of each burst ($1/T_B$) is determined by estimating the number of bursts per unit time, control then passes to block 52 where the duration of each burst ($D_B$) is determined by measuring the time from the first action potential of the burst until the final action potential of the burst. Then, in block 53, the quiescent periods ($Q_P$) between the bursts are determined from measurements of the last action potential in a burst to the first action potentials in another burst. Then, in block 54, the number of action potentials in each burst ($N_P$) are determined Control is then returned to the flow chart of FIG. 4A. The analysis of burst activity is conducted on electromyographic signals stored from at least five (5) bursts of action potentials.

FIG. 4C presents the details of the analysis of action potential performed by block 44 of FIG. 4A. Beginning in block 61, the frequency of the action potential ($1/T_P$) is determined by estimating the number of action potentials per unit time within each burst. Then, in block 62, the duration of the action potentials ($D_P$) is determined by measuring the time from depolarization to repolarization. Control then passes to block 63 where the magnitude of the action potentials ($M_P$) is determined from measurements of the peak voltage of the depolarization. Control then passes to block 64 where the rate of rise of the action potentials ($R_P$) is determined by determination of the slope dv/dt of depolarization. Conduction is estimated in a known manner from the rate of rise of action potentials ($R_P$). In general, the greater the rate of rise, $R_P$, the higher the conduction. Conduction may also be estimated from analysis of data when more than one surface electrode is used and time between bursts from separate electrodes is estimated or after vaginal stimulation (see below). In another preferred embodiment, the rate of all of the action potentials ($F_P$) is also determined. The rate of fall is also useful in estimating conduction. Control then returns to the flow chart of FIG. 4A.

Figure 4D:
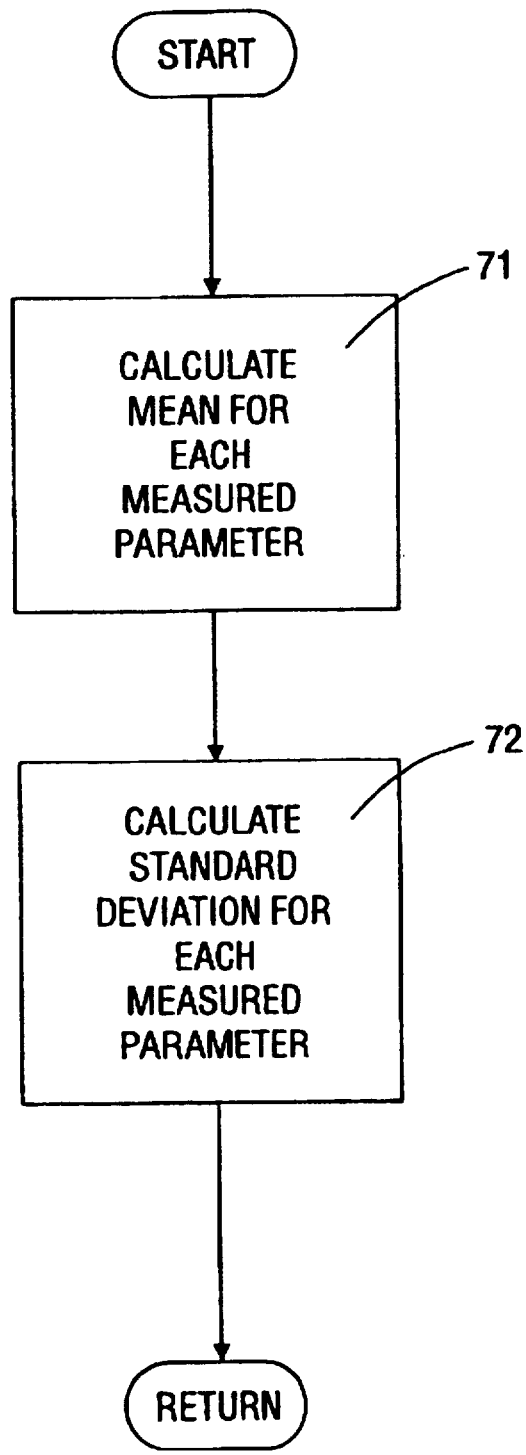

FIG. 4D shows details of the probability analysis performed by block 46 of FIG. 4A. Beginning in block 71, the mean of each of the measured parameters is determined (see also, FIGS. 4B and 4C), and the standard deviation of each of the parameters is calculated. In another embodiment, other properties of the distributions of these parameters are also considered.

Figure 4E:
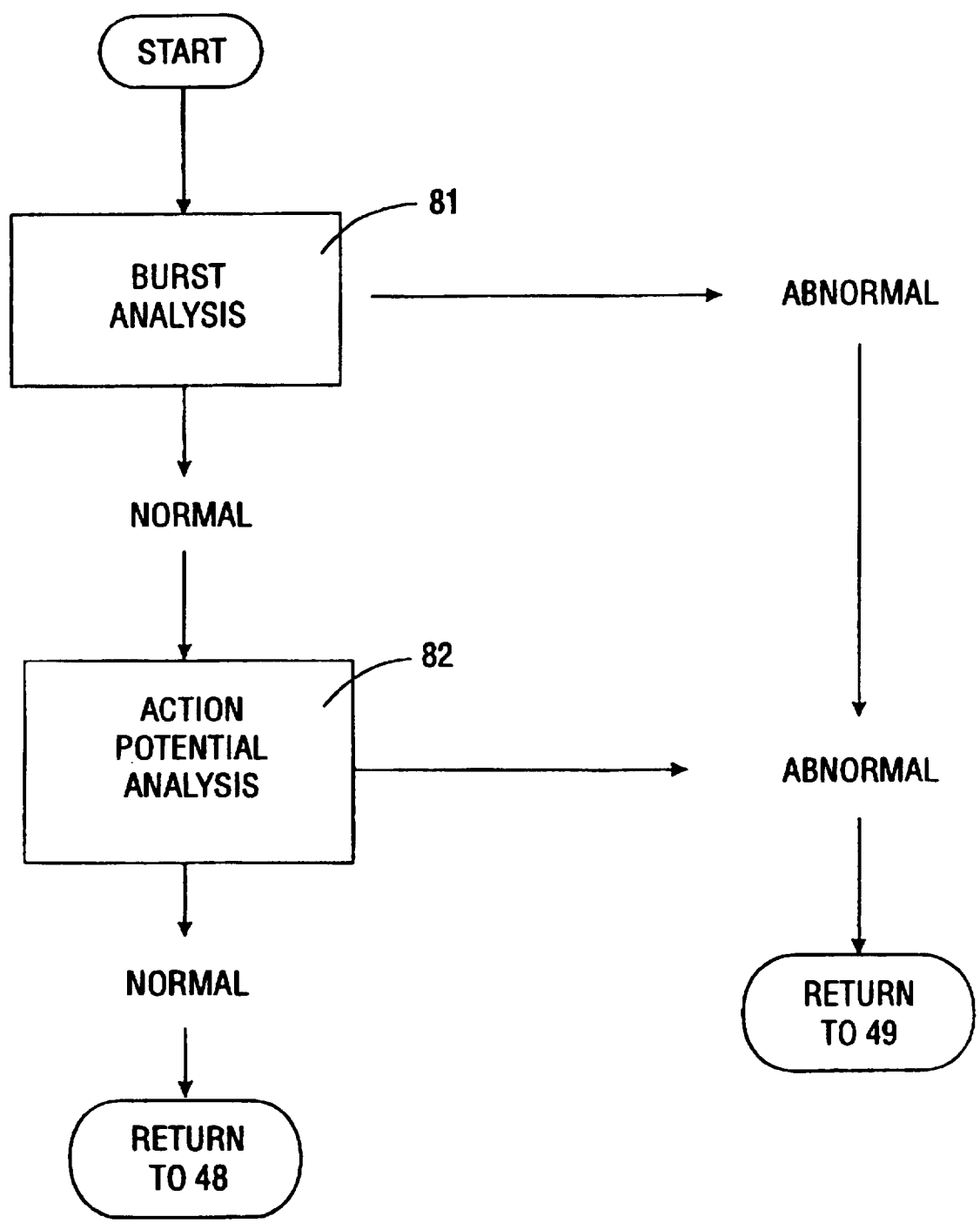

FIG. 4E presents the details of the diagnosis step (block 47). Data from burst and action potential probability analysis (block 46) pass to blocks 81 and 82 respectively and recorded burst and action potentials are compared to known normal ranges of values. Estimates for normal values for the measured parameters for action potentials and bursts of action potentials for human labor patients are presented in the following tables. Expected values of action potential parameters and burst parameters vary as a function of the classification of the patient.

Figure 4F:
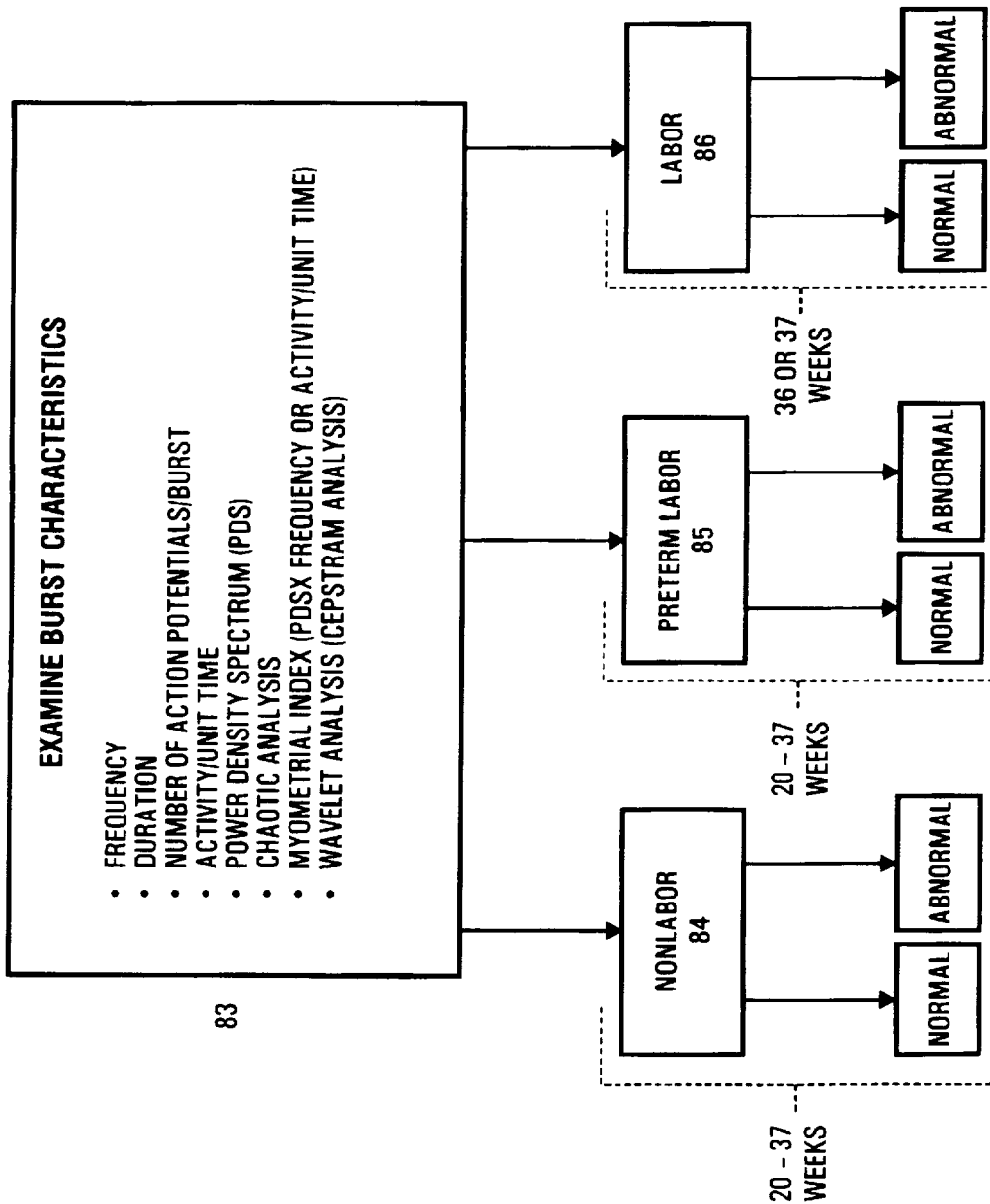

FIG. 4F presents the details of the burst analysis depicted in block 81 of FIG. 4E. The examination of burst characteristics, as depicted in block 83 of FIG. 4F, comprise an examination of one or more of the following characteristics: frequency, duration, number of action potentials per burst, activity per unit time, power density spectrum (PDS), chaotic analysis, myometrial index, and wavelet or Cepstrum analysis. After the burst characteristics are examined, the patient's conditionmay be diagnosed. This diagnosis may result in a determination that the patient is in non-labor, pre-term labor, or labor, as shown in blocks 84–86 of FIG. 4F.

Figure 4G:
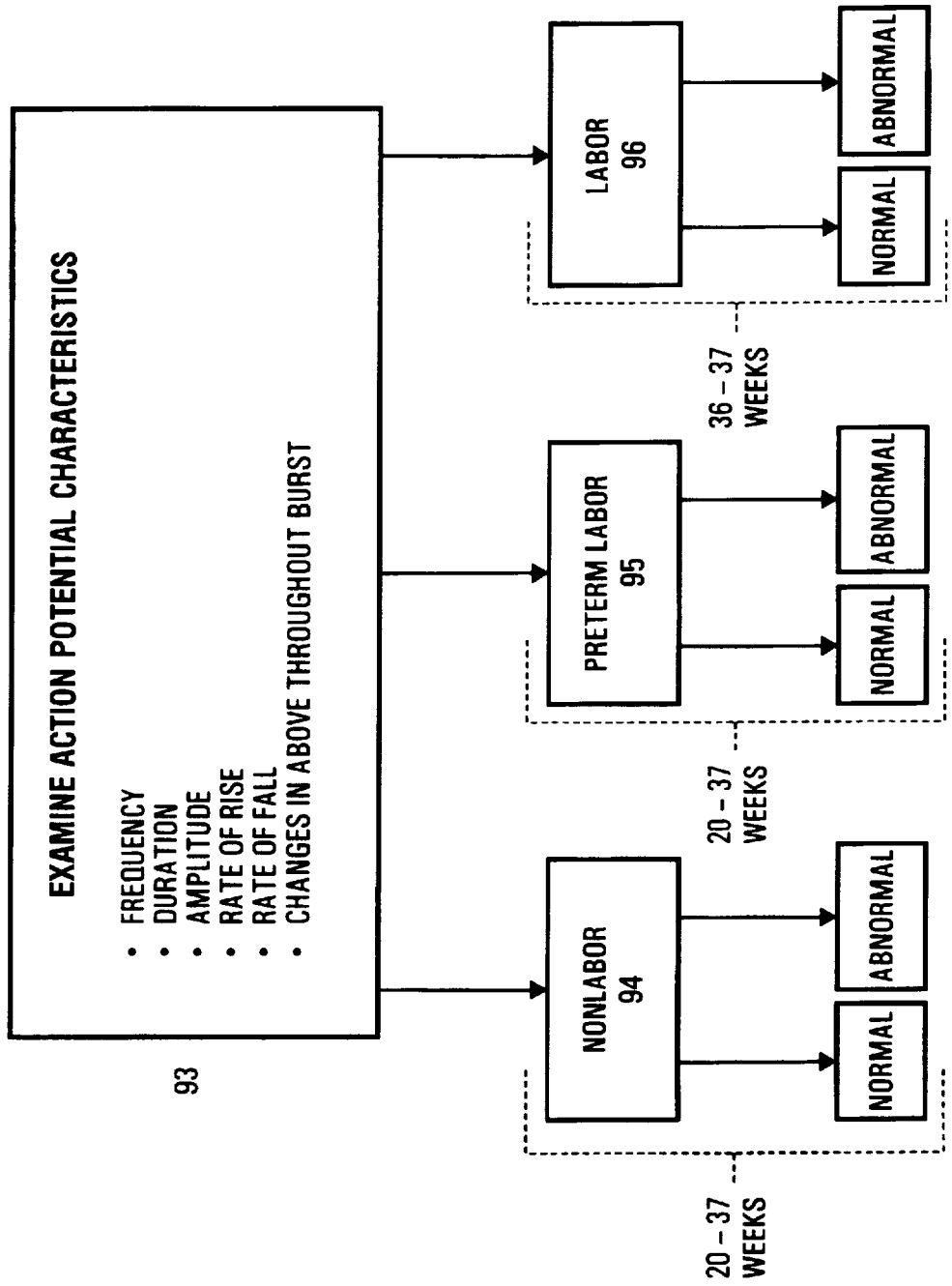

The action potential analysis of block 82 in FIG. 4E is depicted in FIG. 4G. The examination of action potential characteristics, referred to in block 93, comprises an examination of one or more of the following characteristics: frequency, duration, amplitude, rate of rise, rate of fall, and an analysis of changes in any of the above characteristics. After the action potential characteristics are examined, the patient's condition may be diagnosed. This diagnosis may result in a determination that the patient is in non-labor, pre-term labor, or labor as shown in blocks 94–96 of FIG. 4G.

| ACTION POTENTIALS | |
|---|---|
| Frequency: | 0.5–1.2/second |
| Duration: | 50–200 milliseconds |
| Amplitude: | 0.2–1.2 millivolts |
| BURSTS | |
| Frequency: | 0.3–0.4/minute |

| | |
|---|---|
| Duration: | 10–30 seconds |
| Action Potentials/Burst: | 10–30 |
| Power Density: | 10–50 microvolts/second |

For non-labor patients, values for the measured parameters for action potentials and bursts of action potentials are considerably lower than the values presented in the above tables, with the exception of burst duration which may actually be larger. For values either higher or lower than normal for burst or action potential data, the computer recognizes these as abnormal and passes control to block 49. If burst or action potential parameters are within normal limits, the information passes to block 48. The calculated standard deviations for the measured parameters are used to determine whether the calculated parameter means for statistically different or the same as normal values.

While utilization of the apparatus and method has been described above as particularly useful for monitoring the uterine wall during pregnancy, the instrument can also be used to measure electrical activity from the vagina that propagates or conducts from the uterus. This is particularly useful in early pregnancy or in nonpregnant patients where the uterus is small and not in contact with the abdominal wall. In addition, it is within the scope of this invention to utilize the apparatus and method thereof for medical and biological procedures other than uterine wall monitoring, such as, for example bladder or bowel function.

From the foregoing description, one skilled in the art may easily ascertain the essential characteristics of this invention, and without departing from the spirit and scope thereof, may make various changes and modifications of the invention to adapt it to various usages and conditions.

FIGS. 5–14 illustrate use of the present for monitoring uterine electrical activity. To produce the graphs of FIGS. 5–14, bipolar electrodes were placed on the abdominal surface of pregnant rats to monitor EMG activity in accordance with the present invention. In addition, in order to demonstrate the efficacy of the present invention relative to prior, more invasive, procedures, stainless steel electrodes were implanted directly on the uterus and/or vagina wall surface, and, a pressure transducer (specifically, a Model SPR-524 transducer available from Millar Instruments of Houston, Tex.) was placed in the uterus. The apparatus for recording was identical to that described above. The above described invention is designed for use mainly in humans or domestic animals whereas the following FIGS. 5–14 represent data obtained from rats. The instrumentation is essentially the same for both species.

FIGS. 5–14 illustrate the correlation between the EMG signals recorded by the abdominal surface electrodes of the present invention, and signals recorded from uterus electrodes surgically implanted in the uterus.

Figure 5:
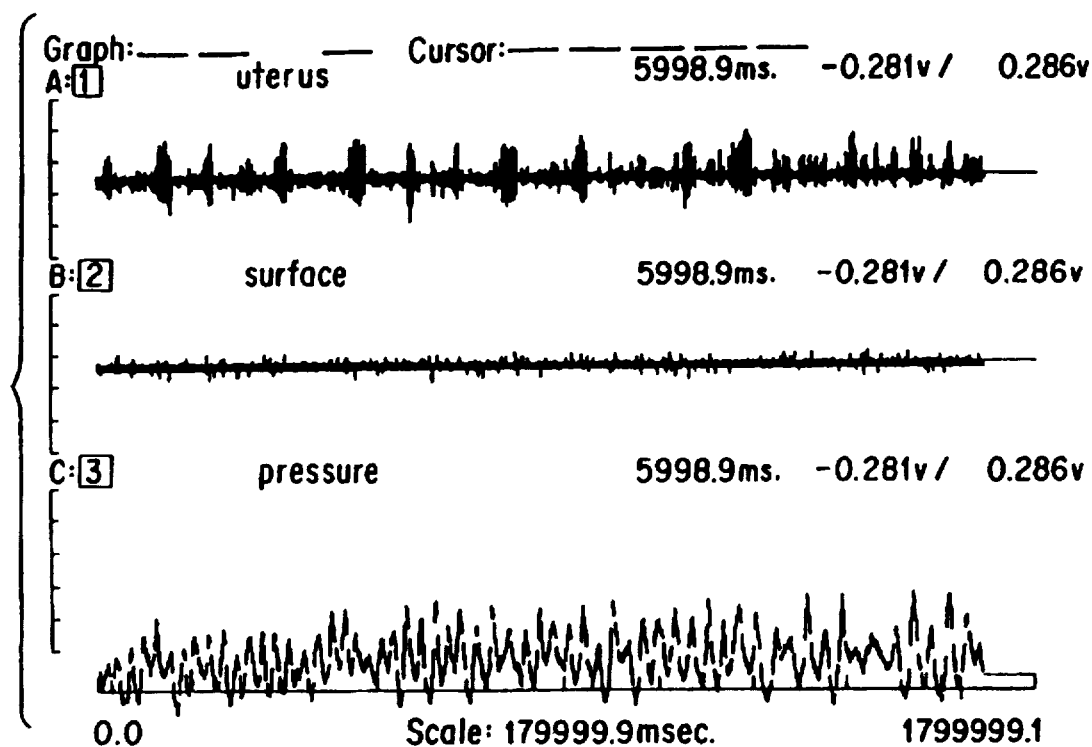
FIGS. 5–14 are graphs of EMG signals, illustrating the present invention.
Figure 6:
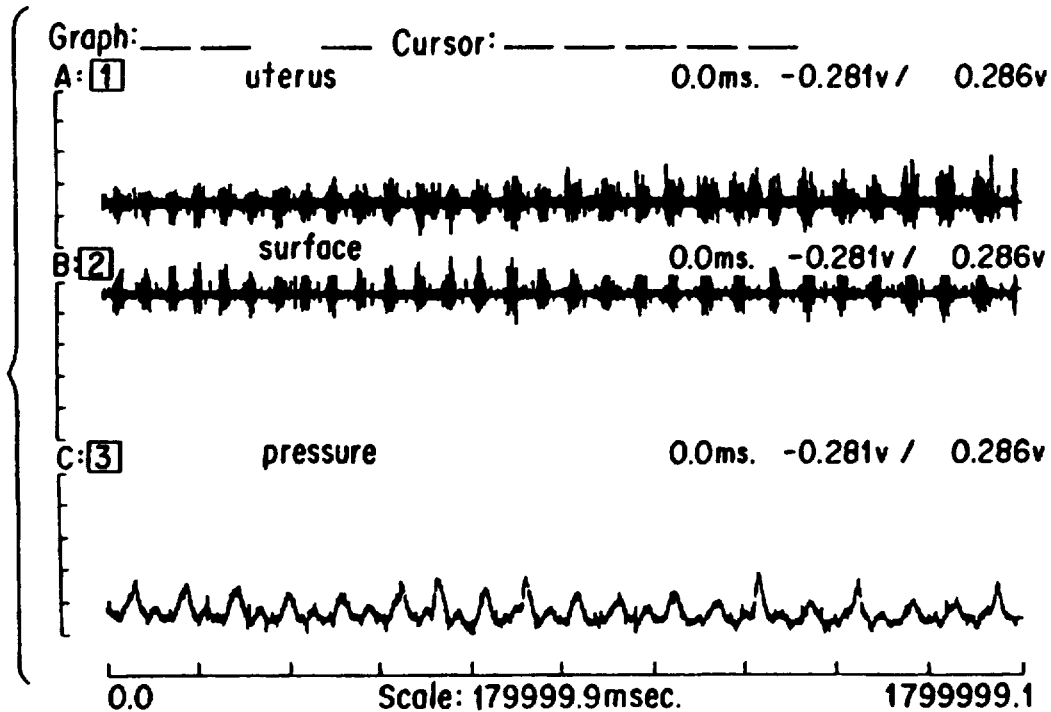
Figure 7:
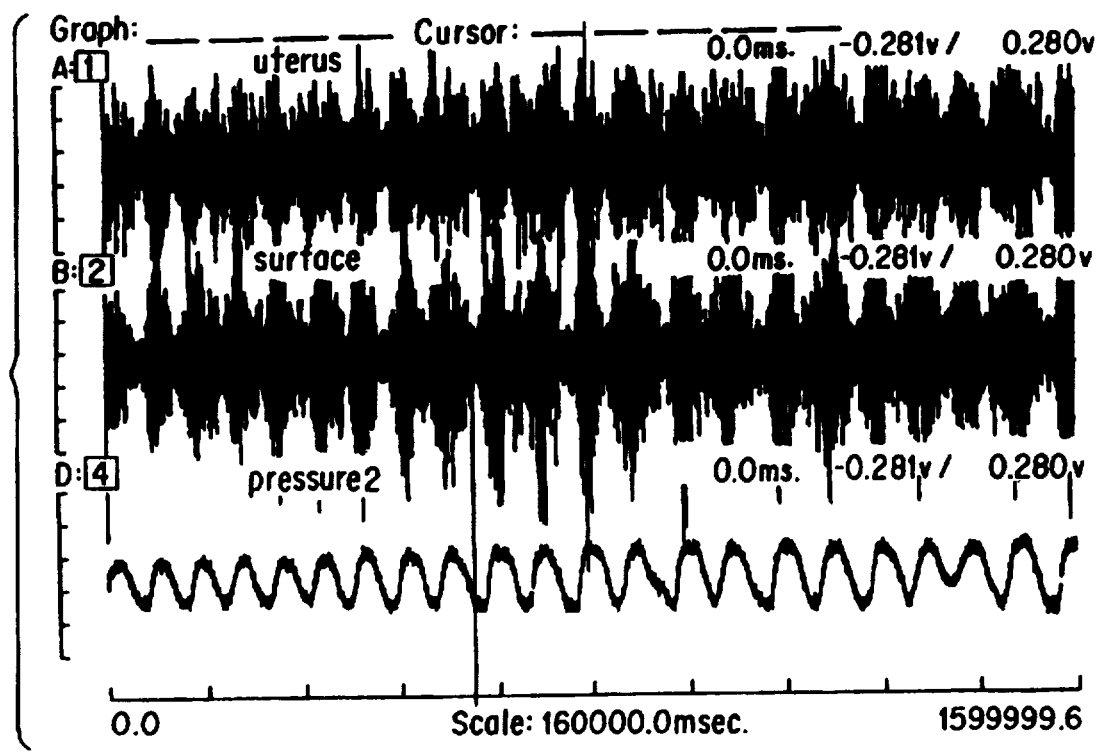

FIGS. 5, 6 and 7 show EMG activity (electrical activity of the uterus) (Channels 1 and 2) and pressure (Channel 3) recorded simultaneously directly from the uterine wall (Channel 1) and from the abdominal surface (Channel 2) of pregnant rats. Pressure (Channel 3) was measured from an intrauterine pressure device. Note that on days 18 and 21 of gestation (FIGS. 5 and 6) bursts of electrical activity are small and do not always correspond on the surface and uterus (FIG. 5, Channels 1 and 2), but do coincide with small uterine contractions (FIGS. 5 to 7, Channel 3). On the other hand, at term during delivery (FIG. 7) the EMG bursts signals from both the uterus and abdominal surface are of high amplitude and correlate with large pressure changes. Additional information may be derived by simultaneous recording of EMG and of contraction or of EMG and of Doppler or ultrasonic images. Contraction may be recorded by a device, such as an intrauterine catheter.

These studies indicate that uterine EMG activity is low prior to term and that it increases dramatically during labor and delivery. Furthermore, these data show that uterine electrical activity may be recorded from the abdominal surface (Channel 2) to give an adequate representation of either the uterine electrical or mechanical activity.

Figure 8:
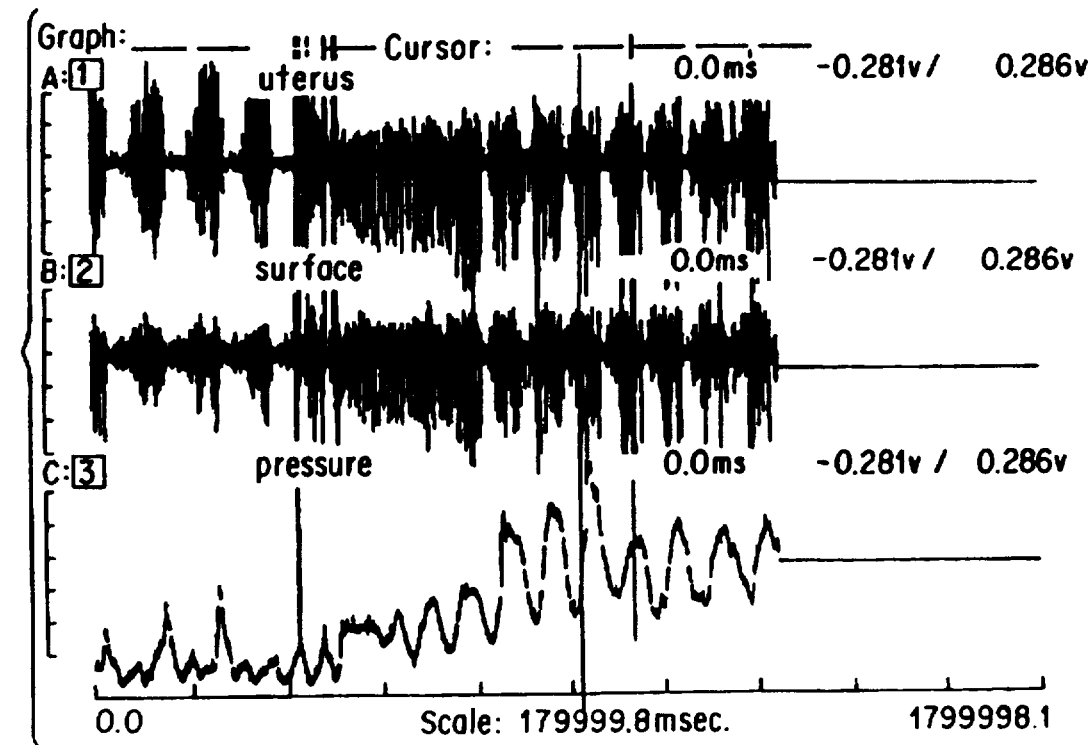

FIG. 8 shows EMG and pressure recordings from an animal during labor at term before and after treatment with oxytocin. Note that the bursts (Channels 1 and 2) coincide to low pressure changes (Channel 3) prior to oxytocin. Following IV infusion of oxytocin the EMG activity as recorded on the uterus (Channel 1), and abdominal surface (Channel 2) increase substantially and correspond to the large pressure changes in the uterus. These results indicate that electrical activity recorded from the surface of the abdomen (Channel 2) accurately mirrors changes in uterine EMG activity (Channel 1) and uterine pressure (Channel 3).

Figure 9:
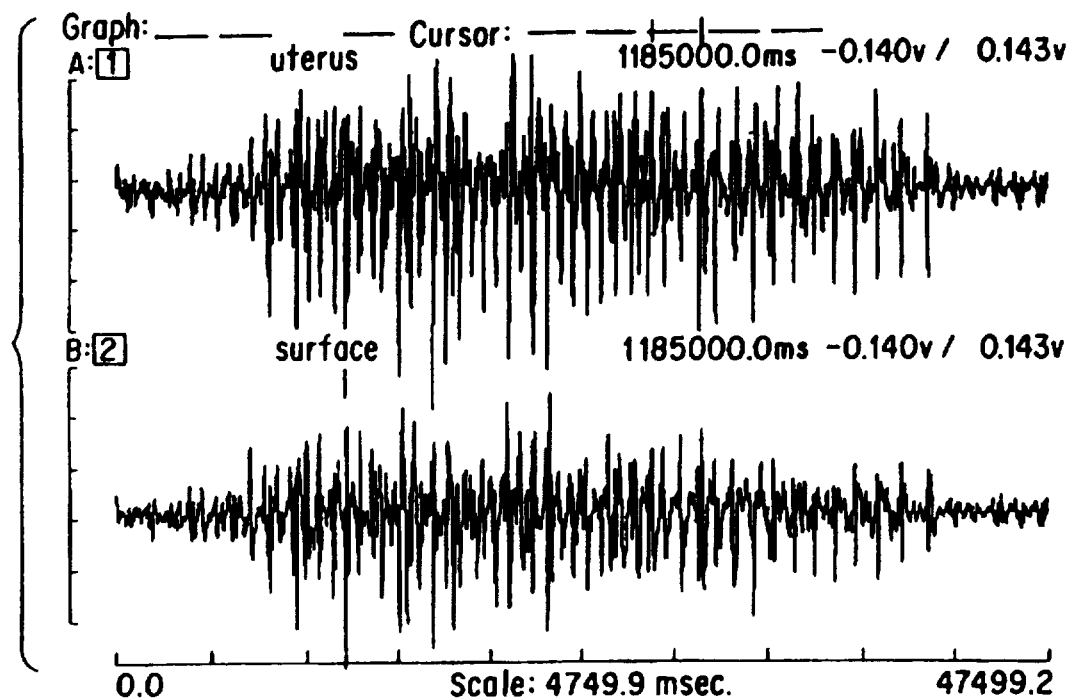

FIG. 9 shows an expanded portion of an EMG burst recorded from the uterus (Channel 1) and abdominal surface (Channel 2). Note that the individual action potentials within the bursts correspond between those recorded from the uterus and surface.

Figure 10:
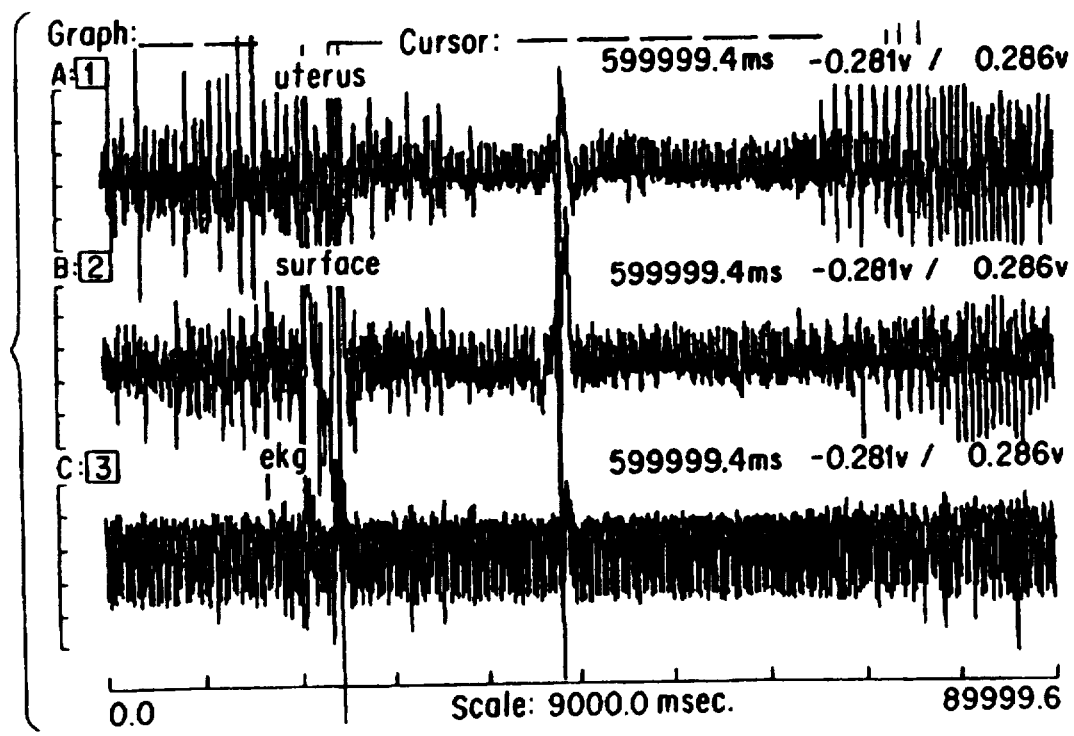

FIG. 10 illustrates EMG activity recorded from the uterus (Channel 1), abdominal surface (Channel 2) and activity of the heart (recorded with external electrodes placed on the chest) (Channel 3). Note that cardiac action potentials occur regularly with a frequency which matched the heart rate (300 to 400 beats per minute). In contrast bursts of action potentials from the uterus recorded with both uterine and abdominal surface electrodes occur periodically. Note that a minor signal from the cardiac potentials appears in the EMG signals from the uterus and uterine signals overlap with some signals from the heart. This information shows that one can record action potential bursts from the uterus with surface electrodes on the abdomen with little interference from the heart.

Figure 11:
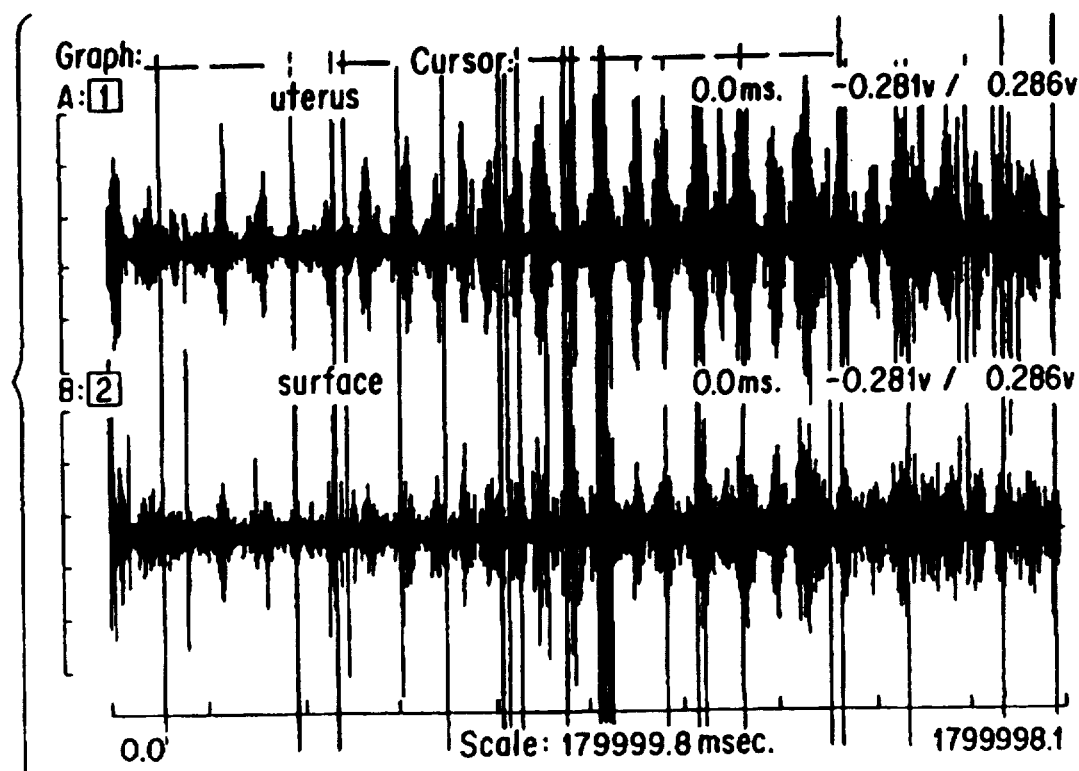

FIG. 11 demonstrates EMG recordings from the uterus and abdominal surface in conscious rats (FIGS. 5 to 10 and FIG. 12 show data from anesthetized animals). Shown are corresponding bursts of EMG activity demonstrating that it is possible to record uterine electrical signals from the abdominal surface from conscious animals.

Figure 12:
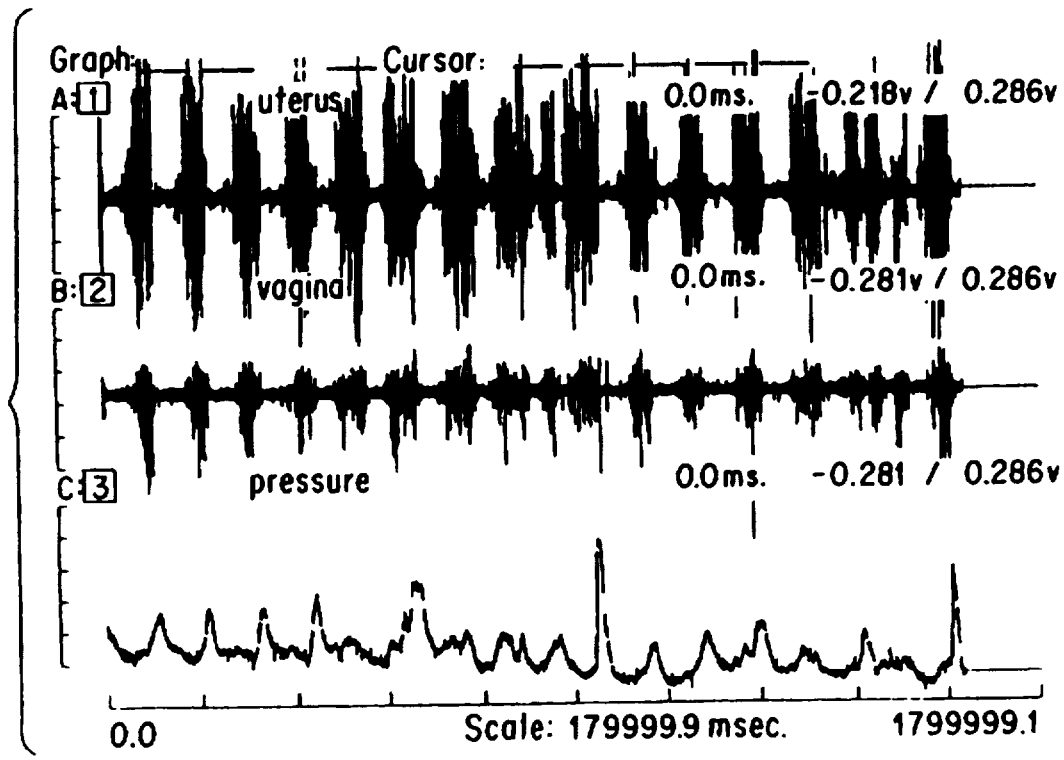

FIG. 12 shows EMG recordings from the uterus (Channel 1) and vagina surface (Channel 2) and intrauterine pressure (Channel 3). Note the correspondence between uterine and vaginal EMG activity with accompanying changes in intrauterine pressure. These studies indicate that it is possible to record uterine EMG activity from the vaginal wall.

Figure 13:
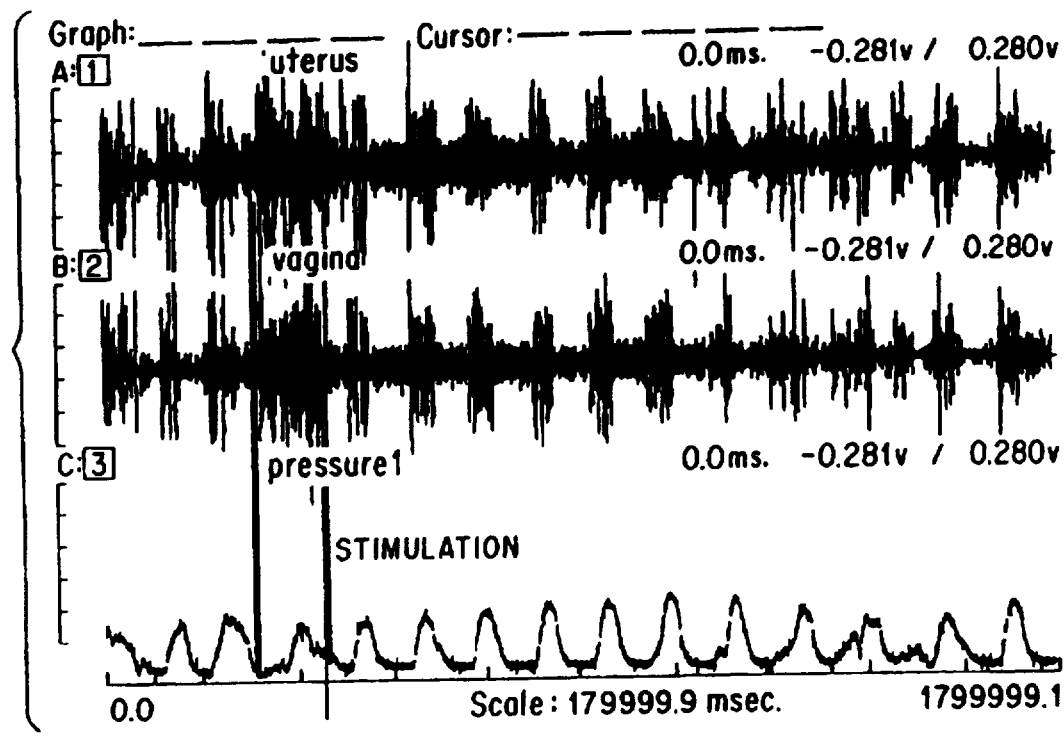
Figure 14:
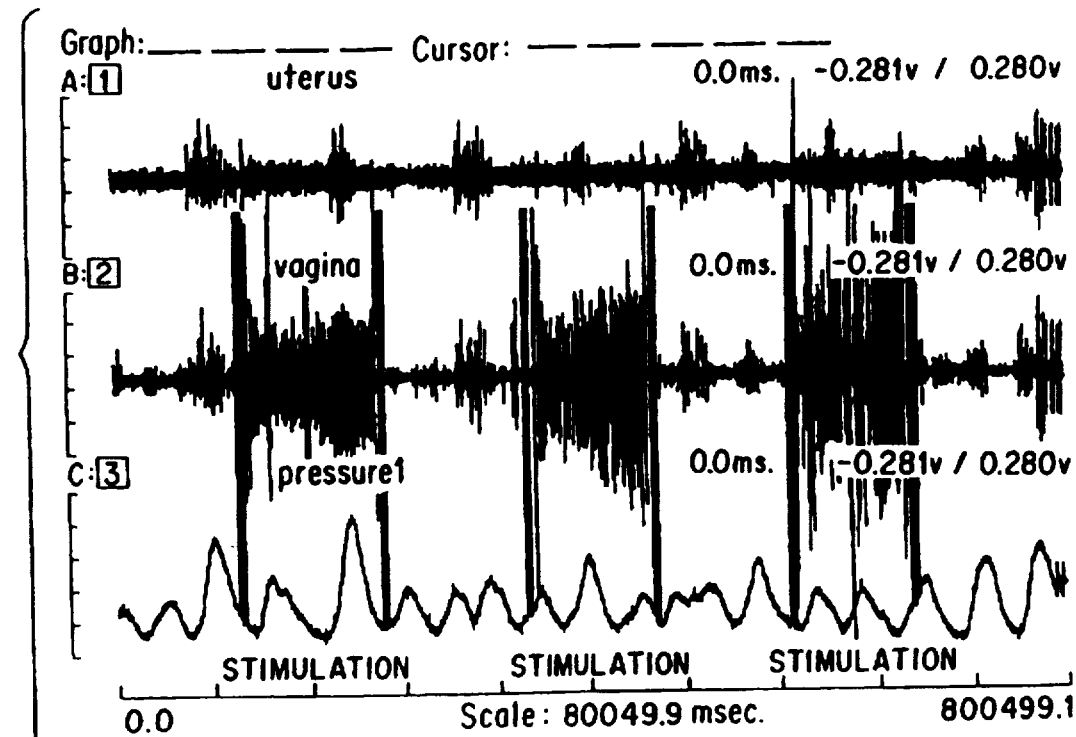

FIGS. 13 and 14 depict a portion of EMG signals recorded from the uterus (Channel 1) and from the vaginal surface (Channel 2), indicating that when the vagina is stimulated mechanically during labor, signals are propagated (conducted) to the uterus (FIG. 13), whereas when the vagina is mechanically stimulated prior to term, signals are not conducted to the uterus (FIG. 14). This assessment of conduction may be used to indicate or diagnose a state of preparation for labor.

The present method and apparatus may also be used to measure normal and abnormal function of other smooth muscle tissue, such as that of the bladder and lower gastrointestinal tract. Both organs depend upon smooth muscle contractility to perform their respective functions. Thus, electrical activity of the bladder and bowel may be registered from the abdominal surface during respective urination or defecation, in order to estimate appropriate and abnormal electrical activity of these organs.

The analysis of EMG activity by abdominal surface recording to determine uterine contractility is further discussed in Buhimschi and Garfield, *Uterine Contractility as Assessed by Abdominal Surface Recording of EMG Activity*, published in AM. J. OB/GYN, 1996; 174:744–53 (February 1996).

Figure 26:
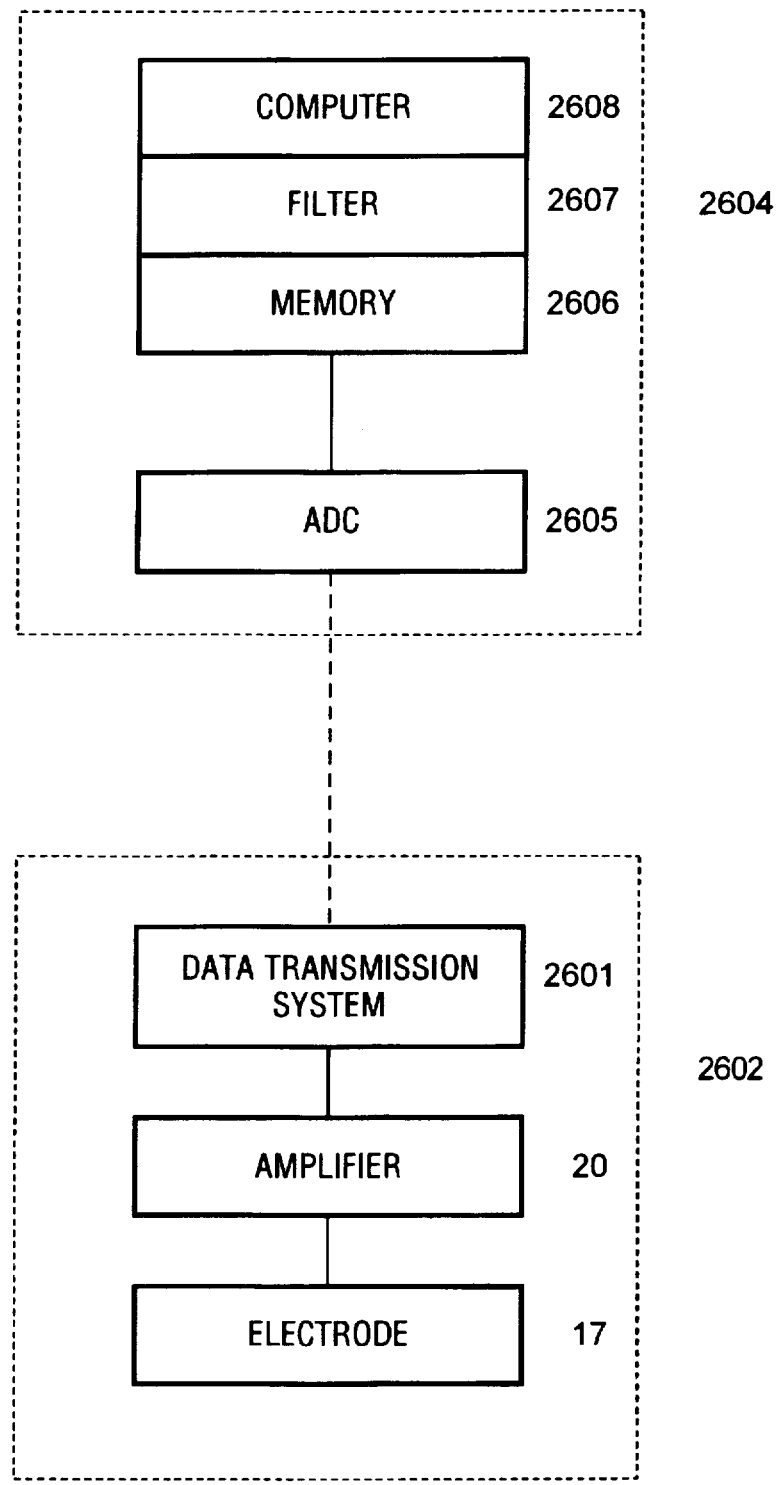
FIG. 26 is a diagram of an application of the present invention as a remote or "home" uterine monitoring system.

The present invention may also be used as a remote or "home" uterine monitoring system. FIG. 26 shows a diagram for an embodiment of a remote monitoring system. Uterine electrical activity may be measured at a remote location, such as in the privacy of one's home, utilizing remote monitor 2602, comprising at least one electrode 17 capable of measuring action potentials emitted from the abdominal or vaginal surface of a patient under analysis and further capable of emitting an analog signal indicative of action potentials measured by said electrode. The remote monitor further comprises an amplifier 20 electrically coupled to the electrode to receive and amplify a signal indicative of action potentials measured by the electrode. The remote monitor also comprises a data transmission system 2601 capable of receiving an amplified signal from said amplifier and transmitting the signal to a remote location from the electrode, as shown in FIG. 26.

In a preferred embodiment, the data transmission system comprises a telecommunication system. In another preferred embodiment, the data transmission system comprises a wireless communication system utilizing electromagnetic energy such as radio waves or microwaves. Such a system may employ analog or digital signals.

The data from these measurements may be sent to a remote data storage and processing device 2604 so that the data may be recorded and/or processed for later use. Alternatively, data from measurements of uterine electrical activity may be processed on-line in real-time by a central data processor or a remote data processor.

In a preferred embodiment, the remote data storage and processing device 2604 comprises a remote analog to digital converter 2605 coupled to the data transmission system to receive an analog input from the amplifier indicative of action potentials measured by an electrode, and a memory 2606 comprising sufficient storage capacity to store data resulting from a sampling of electromyographic signals at a sampling frequency of at least 100 Hz for a duration of time sufficient to record at least five bursts of action potentials. The memory is coupled to receive a digital signal from the analog to the digital converter indicative of action potentials received by the analog to digital converter. The storage and processing device further comprises a filtering device capable 2607 of segregating and identifying electromyographic signals, including action potentials, in a frequency range of .03 to 50 Hz from electromyographic signals outside that range. The remote data storage and processing device further comprises a computer 2608 comprising an expert system programmed to analyze the frequency, duration, amplitude and power density spectrum of action potential bursts and individual action potentials. This expert system is also capable of characterizing uterine activity based upon this analysis.

The present invention may also be used to predict treatment for a pregnant woman. The data signals collected can be analyzed by the present system and compared to existing norms to indicate the appropriate pharmacological treatment depending upon the uterine activity. For example, when signal levels are low and indicative of non-labor, a term patient can be treated in such a fashion pharmacologically to induce labor (i.e., oxytocin, prostaglandins, etc.). When signal levels are high in a patient prior to term (i.e., pre-term labor) treatment can consist of use of uterine inhibitors to suppress labor (e.g., tocolytic agents, β-agonists, calcium channel blockers, etc.). As one of skill would understand, other obstetric diagnosis treatments could be predicted using the present invention.

Figure 15:
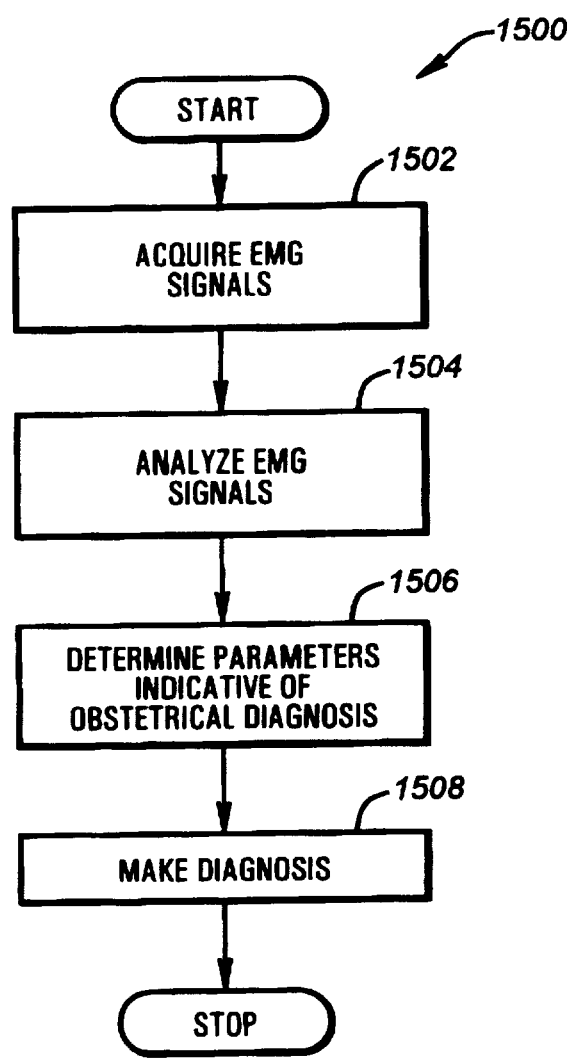
FIG. 15 is a flow chart of a further embodiment of a data processing technique according to the present invention.

From the techniques described above, digital analysis techniques have now been developed and further improved to analyze further the surface EMG activity for obstetrical diagnosis and characterization of uterine activity. FIG. 15 shows a flow-chart for an embodiment of a method according to the present invention. Method 1500 for analyzing surface electromyographic data to characterize uterine activity includes process steps 1502, 1504, 1506 and 1508. In step 1502, EMG signals are first acquired. After this data is obtained, the EMG signals are analyzed in step 1504. Once processed and analyzed, parameters are determined from the EMG signals that are indicative of a obstetrical diagnosis in step 1506. Finally, a diagnosis is made or predicted in step 1508. Within this general framework, a wide variety of data analysis techniques may be employed to analyze EMG signal for obstetrical diagnosis.

These analysis techniques may include: (1) power-density spectral analysis based upon 3-dimension mesh plots (e.g., energy level vs. frequency vs. time of pregnancy), (2) potential vector analysis, and (3) other analytical techniques, such as integration of the EMG signals to provide approximate total energy within a burst of action potentials, fast wavelet transform analysis, and joint time-frequency analysis.

These analytical systems provide important information on EMG that can be used for diagnosis. These systems are based upon the recording of uterine electrical activity from the abdominal surface as described above. The abdominal electromyogram (EMG), or electrohysterogram (EHG), may be analyzed and the resulting analysis used to facilitate the clinical evaluation of uterine activity during pregnancy. The present invention may also be utilized for the early diagnosis of abnormal uterine contractility by analyzing uterine EMG signals. Such diagnoses take advantage of the characteristic that uterine electrical activity gradually changes during the last month of pregnancy until parturition. Weak and localized at the beginning of labor, this electrical activity becomes stronger, rhythmical and well propagated during labor. EMG, therefore, offers much information about both excitation and propagation of uterine activity.

Figure 16:
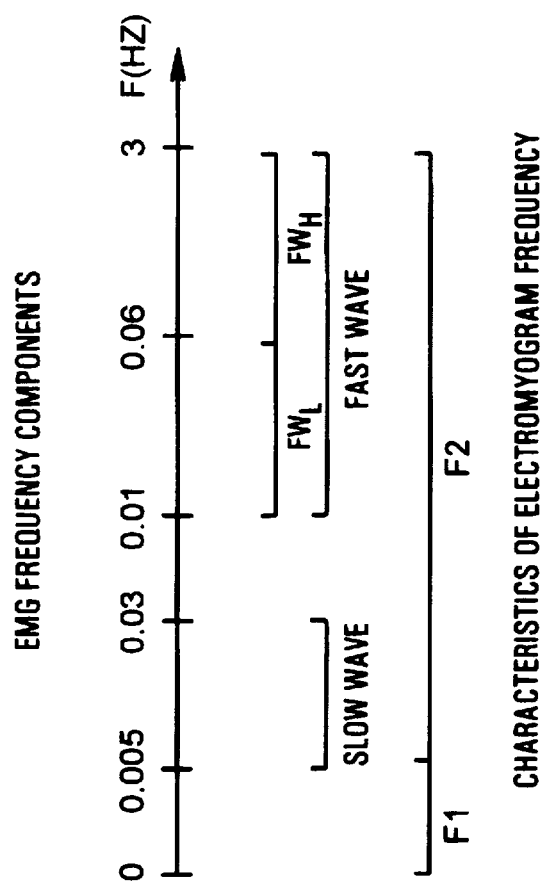
FIG. 16 is a diagram of electromyogram frequency components.
Figure 17:
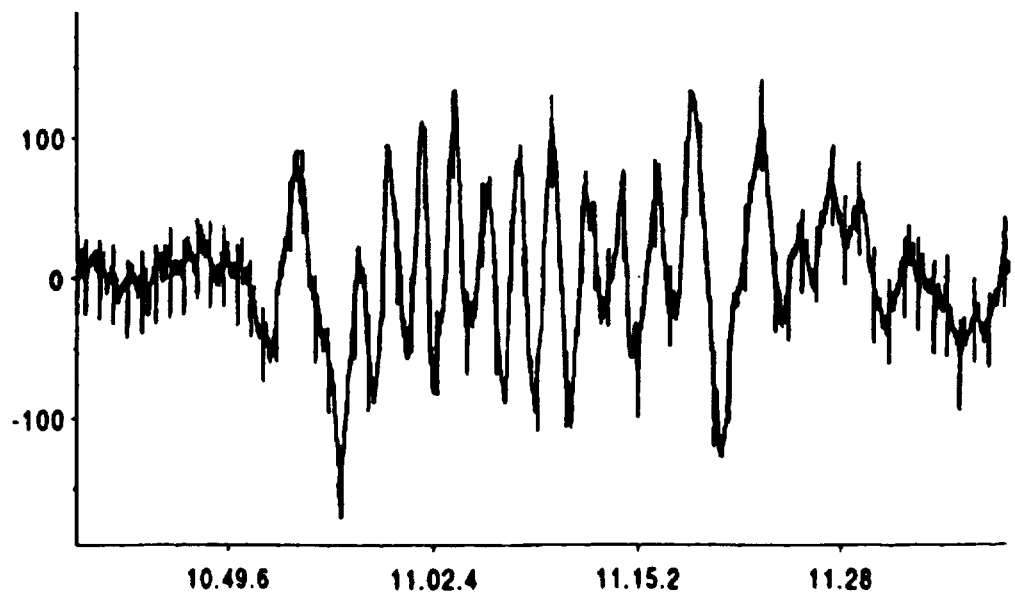
FIG. 17 is a graph of a burst of action potentials recorded from the abdominal surface of a pregnant patient.

These data analysis techniques also rely upon an unique approach to characterizing EMG frequency components of a burst of action potentials. FIG. 16 shows the EMG frequency components of a burst of action potentials recorded from a human uterus. A burst of action potentials is shown in FIG. 17, which provides an amplitude versus time graph of a burst of action potentials recorded from the abdominal surface of a pregnant patient.

In a preferred embodiment, the uterine activity may be analyzed by determining (a) the mean frequency of a plurality of action potentials in at least one measured burst, (b) the starting frequency of action potentials in at least one measured burst, and (c) the ending frequency of action potentials in at least measured burst. In another preferred embodiment, the uterine activity may be analyzed by determining the rate of rise of amplitude in at least one action potential in at least one burst, and the rate of fall of amplitude in at least one action potential in at least one measured burst.

Referring back to FIG. 16, F1 (less than 0.005 Hz) is representative of low frequency components in the EMG data, such as the periodic occurrence of a burst. During human parturition, the burst frequency corresponds to a maximum of four contractions per 10 minutes (i.e., maximum F1=0.005 Hz). F2 (approximately 0.005 to 3.0 Hz) is representative of high frequency components, such as the intrinsic spike frequency within each burst. F2 frequencies are believed to be more significant than F1 frequencies because they are related to the intensity of the uterine contraction.

F2 can be divided into two distinct activities: a slow wave component and a fast wave component (FW). The slow wave component, ranging from approximately 0.005 to 0.03 Hz, is mainly obtained with abdominal recordings and is likely caused by mechanical artifacts. The fast wave component is of more importance and is the frequency band representative of uterine activity (about 1 Hz for a human). This fast wave frequency spectrum can be recorded in virtually all situations (myometrial or abdominal recordings, parturition of pregnancy).

In turn, this fast wave component contains two specific domains: a low-frequency ($FW_L$) domain present in any uterine electrical recording and a high-frequency ($FW_H$) domain. The $FW_L$ domain relates to lower frequency components (e.g., $FW_L$ is in an approximate range from 0.01 to 0.06 Hz) having a longer duration (the duration mean was computed as 74.6 sec). In contrast, labor EMG is related to the presence of "high" frequency components (e.g., $FW_H$ is in an approximate range from 0.06 to 3.0 Hz) having a shorter duration (the duration mean was computed as 59.3 sec).

The relationship between $FW_L$ and $FW_H$ has been found to indicate preterm and term uterine activity. It may also be useful in making other obstetrical diagnosis. This relationship can be expressed by various parameters, including parameters that are not dependent on the individual patient. Thus, these parameters may be used as differentiation parameters in indicating diagnoses and characterizing uterine activity.

The following data analysis techniques are based upon analyses of EMG signals using various approaches and represent different definitions and calculations of these parameters.

1. Power-Density Spectral Analysis a. Spectral Analysis Technique

A spectral analysis method may be used to obtain important spectral characteristics of uterine EMG and define some key parameters useful in the differentiation of normal and abnormal uterine activity.

Figure 18:
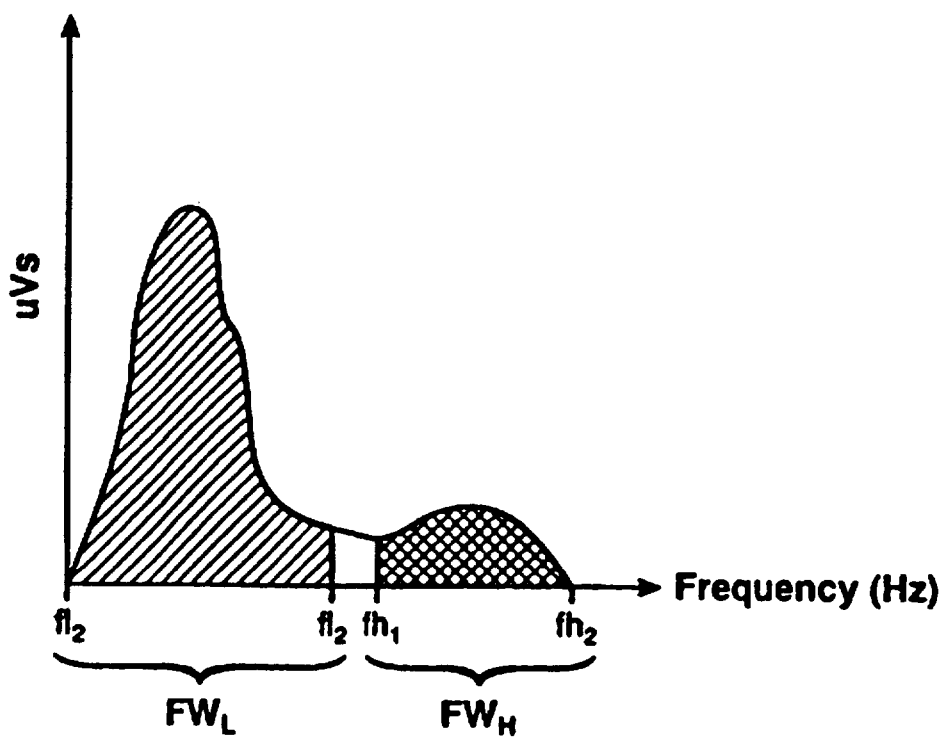
FIG. 18 is a graph of a spectral density curve.

To specify the frequency range that only concerns the previously defined "fast" electrical activity, spectral analysis processing is performed on the phases of EMG corresponding to contractions of the pressure signal. The power density spectrum (PSD) curve which is computed from the filtered "fast" (0.2–3.0 Hz) electrical burst relates to one contraction (see FIG. 17). The pregnancy contraction mainly corresponds to the $FW_L$ frequency band and the labor contraction to the $FW_H$ band. The energy on each of $FW_L$ and $FW_H$ band can be calculated. Defining $E_{fwL}$ as the energy of $FW_L$ band and $E_{fwH}$ as the energy of $FW_H$, the total energy $E_{fw}$ on the FW band is $E_{fwL}+E_{fwH}$. The formula is as follows:

$$E_{fwL} =$$

$$\int_{fl1}^{fl2} P(f)df \ (FW_L \text{ frequency bandwidth is } [fl1,fl2] \text{ as shown in FIG. 18})$$

$$E_{fwH} =$$

$$\int_{fh1}^{fh2} P(f)df \ (FW_H \text{ frequency bandwidth is } [fh1,fh2] \text{ as shown in FIG. 18})$$

$$E_{fw} = E_{fwL} + E_{fwH};$$

Referring to FIG. 18, which depicts an EMG power spectral density (PSD) curve, the geometrical significance of $E_{fwL}$ and $E_{fwH}$ are the areas under the PSD curve. The physical significance of $E_{fwL}$ and $E_{fwH}$ is the energy of contraction in pregnancy phases. The energies in different pregnancy phases and labor stages are expected to be different. The EMG signals that are processed are discrete signals. Their PSD are also discrete functions. So, $E_{fwL}$ and $E_{fwH}$ can be calculated as follows:

$$E_{fwL} = \sum_{f=fl1}^{fl2} PSD_f,$$

$$E_{fwH} = \sum_{f=fh1}^{fh2} PSD_f,$$

The energy may be dependent on the individual patient. Supposing that the ratio (Re) of $E_{fwL}$ and $E_{fwH}$ is independent of individuals, standard ratios (possibly invariable) may be developed at each different stage of pregnancy, pre-labor and labor. Thus, the following ratio may be particularly useful as a parameter indicative of an obstetrical diagnosis:

$$Re = E_{fwH}/E_{fwL}.$$

Based on this supposition, the ratio in the early pregnancy phase is expected to be smaller than the ratio in later pregnancy and the labor phases. This ratio will increase with the days of pregnancy. This means the $E_{fwL}$ decreased but the $E_{fwH}$ increased. In the normal state, the ratio in a certain phase of pregnancy or labor is expected to be a standard ratio. If the ratio in certain phases of pregnancy is larger than the standard ratio in this phase, the woman may be considered to be in an abnormal pregnancy state (the commencement of premature labor or miscarriage). If the ratio is smaller than the normal ratio, the woman may be in danger and may suffer post-labor or dystopia problems.

Figures 20A, 20B:
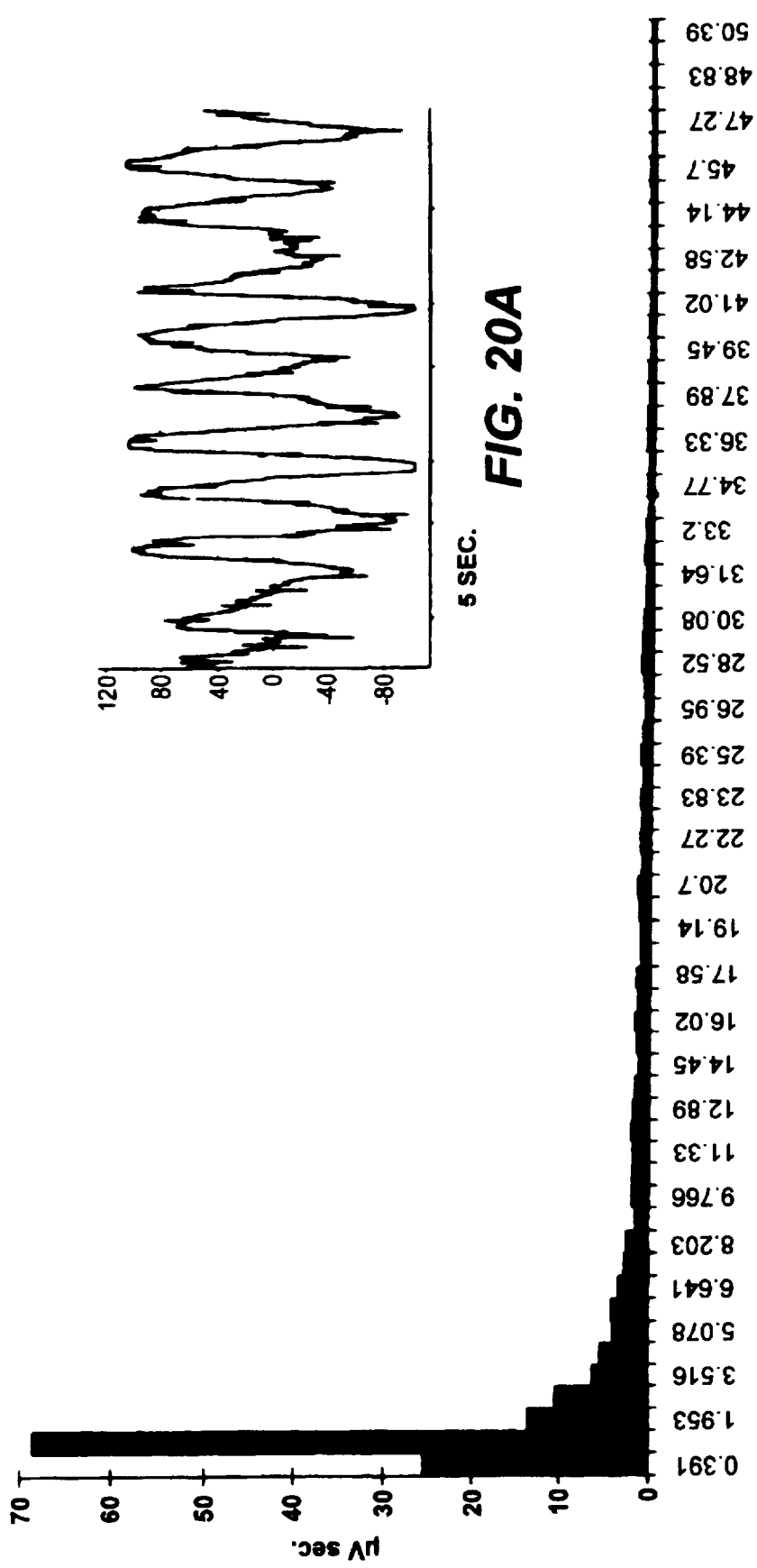
FIGS. 20A–20B are a burst of action potentials recorded from a human abdominal surface, and a spectral analysis of this burst, respectively.

FIGS. 19A–19B and 20A–20B show power density spectra for $FW_H$ components during labor. FIG. 19A is a burst of action potentials recorded from a rat's abdominal surface. FIG. 19B is a power density spectra obtained for the burst shown in FIG. 19A. As evident from FIG. 19B, labor in a rat is indicated by a large frequency component between 2–3 Hz. FIG. 20A is a burst of action potentials recorded from a patient's abdominal surface. FIG. 20B is a power density spectra obtained for the burst shown in FIG. 20A. As evident from FIG. 20B, labor in a woman is indicated by a large frequency component at approximately 1 Hz.

b. Application of Spectral Analysis

The development of spontaneous uterine contractility exists throughout pregnancy, labor, and the early postpartum. Changes in magnitude of uterine activity in relation to duration of pregnancy and to the successive stages of labor and postpartum increases dramatically during labor. These correspond to the tremendous increase in electrical activity (PSD) during labor.

In the examples described below, the whole EMG data was classified as normal or abnormal (pre-labor, miscarriage, post-labor, labor difficulty, etc.) according to the end-result. If a woman finished normal delivery, the whole EMG data was classified as normal, otherwise it was classified as abnormal. After acquiring EMG data, the temporal and spectral characteristics of this data was analyzed for important statistical parameters. The parameters include Re, $E_{FWL}$, $E_{FWH}$, duration of contraction, and statistical data, such as correlation coefficient and covariance.

In the study, two Ag—AgCl Beckman electrodes (8 mm in diameter, 25 mm spaced centers) were placed on the abdominal wall after careful preparation of the skin. They were located on the median vertical axis, halfway between uterine fundus and the symphysis, thus parallel to the more superficial uterine fibers. The ground electrode was located laterally on the hip. These electrode locations, based on common anatomic references, have been found to provide good EMG results.

The MacLab digital signal acquiring system was used to obtain EMG signals. The mechanical effect of uterine contractions were recorded by the existing method of pressure recording with an intrauterine catheter or surface pressure with a tocodynamometer. The pressure recording detects weak contractions in pregnancy. The pressure signal may be simultaneously recorded with the EMG, providing a time reference for the appearance of contractile activity.

c. Filtering to Eliminate Noise

The raw EMG signals can be contaminated by noise. The noise includes respiratory artifact, background noise due to motion, and ECG (material and fetal). Adaptive Noise Canceling (ANC) and Adaptive Line Enhancer (ALE) methods with the LMS (least mean squares) adaptation algorithms were used to cut off the noise. The noises were first classified into reference noises and background noise that contaminate the EMG signal according to their frequency range. The frequency range of the EMG fast wave component lies mostly between 0.2 Hz and 3 Hz. The frequency of respiratory artifacts is around 0.3 Hz. Some overlap, therefore, exists between frequencies caused by the respiratory artifacts and the EMG signals. An adaptive noise canceler is used to eliminate the respiratory artifact from the desired uterine EMG measurements.

The ECG signal (from heart activity) frequency range is greater than 2 Hz. Thus, there may also be some overlap between ECG and EMG signals. However, this overlapping part of the ECG signal has very low energy. The nonoverlapping part of the ECG can be processed as background noise. Thus, the noises that contaminate the EMG signal are mainly respiratory signals (mostly overlap with EMG) and background noise (including ECG signals).

Figure 21:
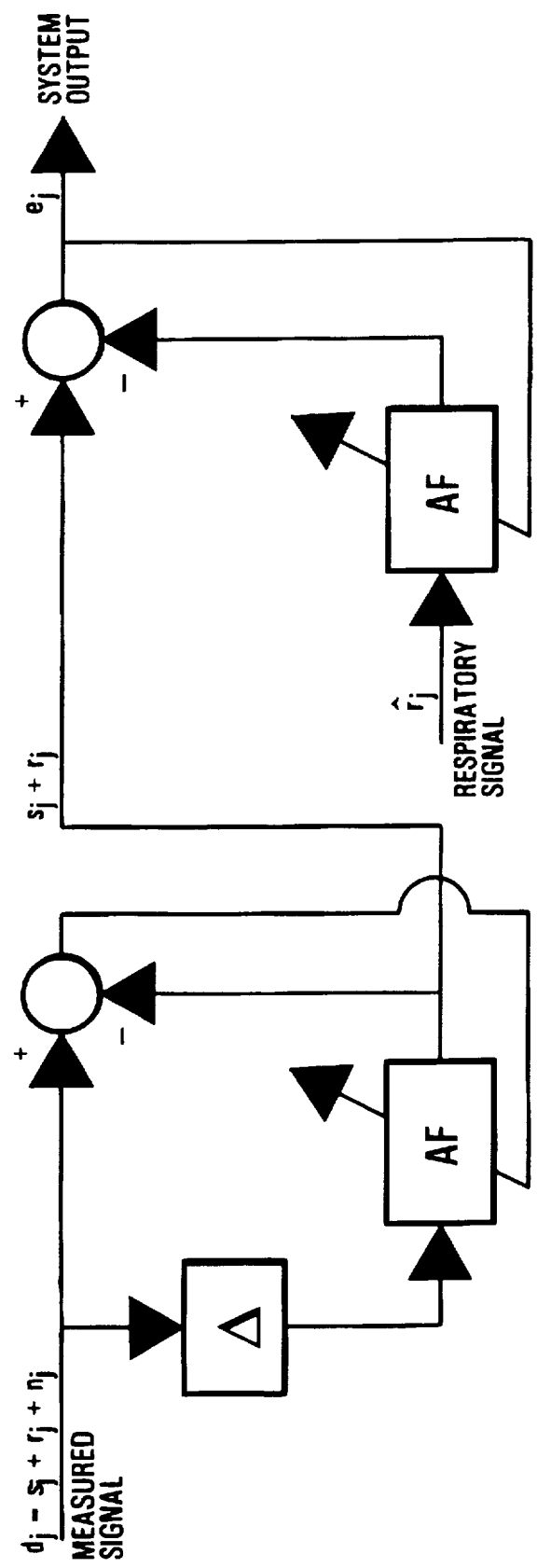
FIG. 21 is a system for reducing noise in electrical activity signals in the present invention.

Referring to FIG. 21, an adaptive system for reducing the noise in the EMG signal is shown. In particular, an adaptive filter system is shown, which consists of the Adaptive Line Enhancer (ANE), shown on side (a) of FIG. 21, and the Adaptive Noise Canceler (ANC), shown on side (b) of FIG. 21. The components for these systems are available from Newark Electronics, Chicago, Ill. Both filters use a LMS (least mean square) algorithm.

In operation, the main signal $d_j$, which includes the EMG signal or primary signal $(s_j)$, is bandpass filtered with bandwidth 0.2–3.0 Hz before adaptive filtering. An adaptive noise canceler (ANC) is used to filter out respiratory noise $(r_j)$. Here, a respiratory signal is also a reference signal $(r_j)$ of the ANC. A respiratory reference signal is recorded by positioning a pressure transducer on the chest above the diaphragm. The Adaptive Line Enhancer (ANE) is to eliminate the background noises $n_j$ from the primary signal $s_j$. The delay, $\Delta$, is chosen as one constant according to practical experiments to decorrelate the periodic and correlated signals $s_j$ and $r_j$ from $n_j$.

Thus the Adaptive Line Enhancer (ANE) part of the adaptive system functions as a preprocessing unit to eliminate the background noise $n_j$. The adaptive noise canceler is used to eliminate respiratory artifacts $(r_j)$. After the processing, an enhanced main EMG signal $(s_j)$ is acquired and may be analyzed.

d. Time and Shape Analysis of Burst Power

The power density spectral analysis does not define differences in power density at different time points within the burst. This is likely important during pregnancy when electrical coupling is poor prior to term as compared with well coupling during labor. In this type of analysis, the power of the burst over time is expressed. Prior to term, this analysis is expected to show a weak initial signal with a peak during the mid-phase of the burst. Because electrical coupling is improved during normal labor, the power per unit time is expected to be maximal with little change from beginning to the end of a burst.

e. Application of Spectral Analysis Technique

To specify the frequency range representative of the previously defined "fast" electrical activity, the spectral analysis is performed on the EMG signal phases corresponding to contractions. The contractions are detected by recording pressure at the same time when the EMG signals are recorded. The power spectral density is computed in the frequency range 0.2–3.0 Hz with a Kaiser Window Filter. An estimation technique of parametric modeling methods was used to calculate the PSD. Parametric modeling methods include AR (Autoregressive Methods) and ARMA (Autoregressing Moving Average Method).

According to the PSD, the energy on discriminating frequency bands $FW_L$ and $FW_H$ and the energy ratio Re can be calculated. After acquiring a group of Re's, statistical values of Re and its standard deviation (SD) can be calculated. The power spectral analysis (PSD) can be carried further along into coherence analysis if necessary, such as that described in Sica, et al., Respiration—Related Features of Sympathetic Discharges in the Developing Kitten, *Journal Automatic Nervous System*, 44:77–84, 1993; and Sica, et al., Evidence for Central Patterning of Sympathetic Discharge in Kittens, *Brain Research*, 530:349–352, 1990.

Focusing on frequency analysis of the amplitude or energy levels in bursts of action potentials at various times in pregnancy, mesh plots of the "power density" of the bursts of action potentials can be created. FIGS. 22A–22F represent graphical depictions of power density analyses and 3-dimensional mesh plots for EMG data measured from the uterine activity at a rat's abdomen surface.

Figure 22A:
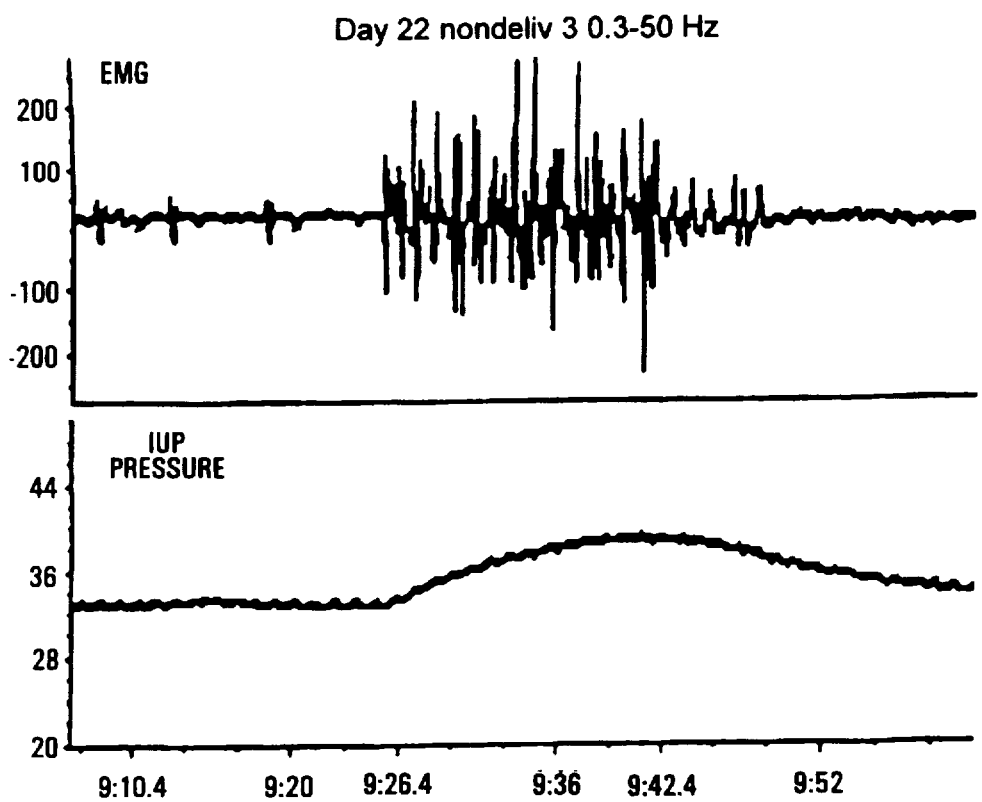
FIGS. 22A–22F are graphs of spectral analyses for bursts of action potentials recorded from a rat abdominal surface.

FIG. 22A shows a burst of action potentials from the EMG signal, as well as the corresponding intrauterine pressure (IUP) changes, recorded from a pregnant rat at day 22, where the rat was not in labor. FIG. 22C shows a burst of action potentials form the EMG signal, as well as the corresponding intrauterine pressure (IUP) changes, recorded from a pregnant rat at day 22, where the rat was in labor. Only frequencies between 0.3–50 Hz in the EMG signal are shown in FIG. 22A and FIG. 22C.

Figure 22B:
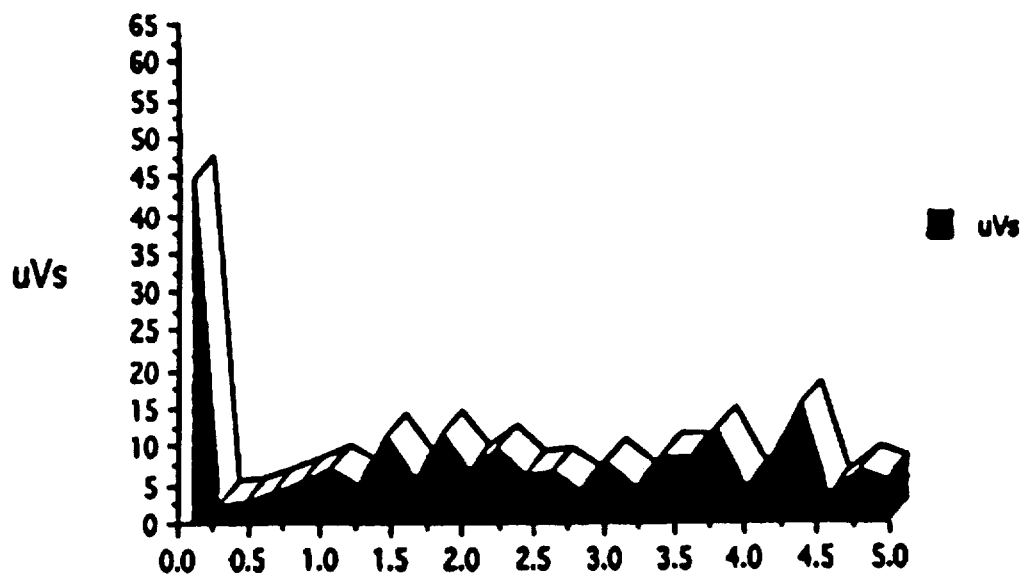
Figure 22C:
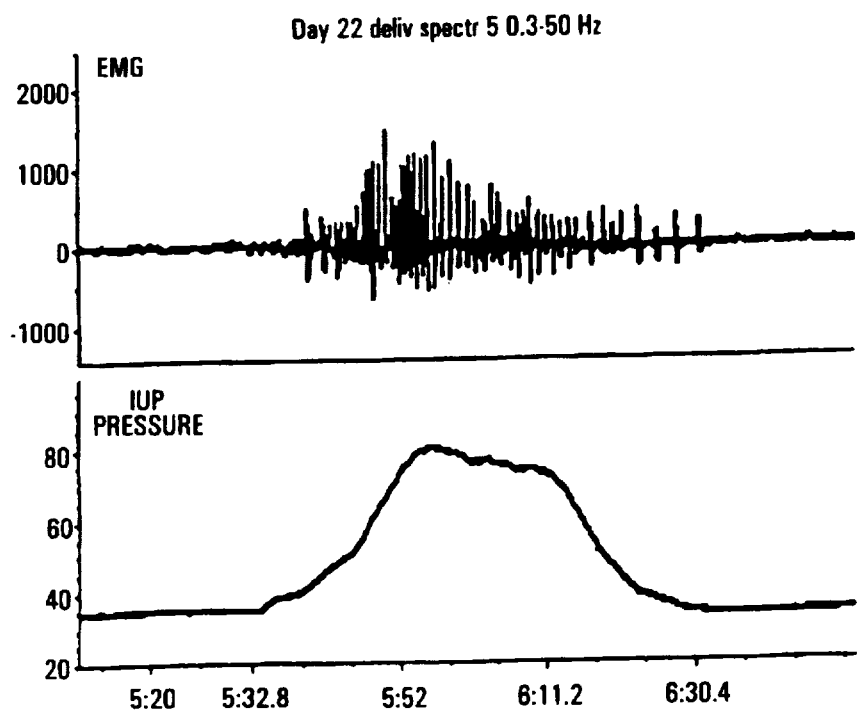
Figure 22D:
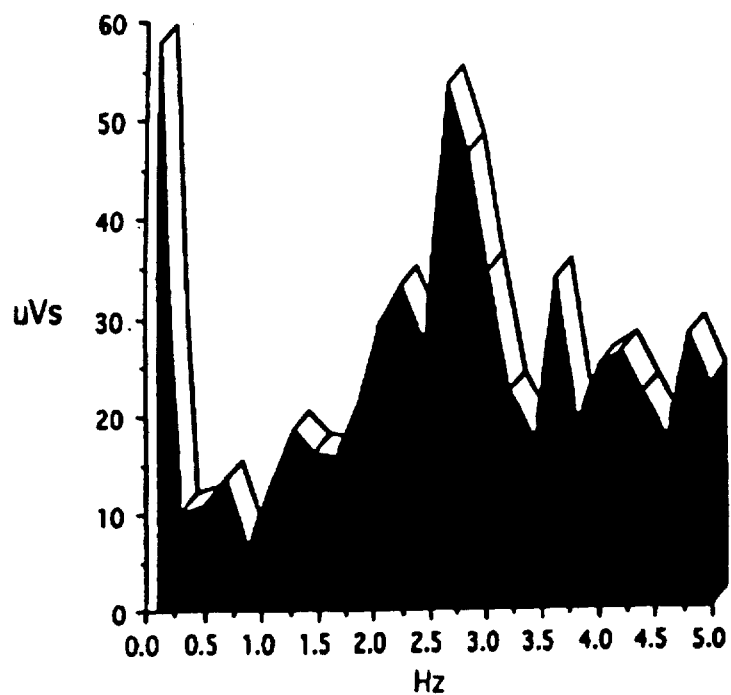

FIG. 22B shows a power density spectral analysis of the burst shown in FIG. 22A. For a rat not in labor, no large frequency components are present, except for a component below 0.5 Hz. This component may attributable to respiratory noise or breathing. FIG. 22D shows a power density spectral analysis of the burst shown in FIG. 22C. In stark contrast to the frequency components present in FIG. 22B, large frequency components are present in FIG. 22D. Comparing FIG. 22B and FIG. 22D, it is significant to note that the peak frequency of the action potentials occurs between approximately 2–3 Hz in a delivering rat and that very high energy levels occur during labor as compared to a non-delivering rat. It should also be noted that a large frequency component is still present in FIG. 22D below 0.5 Hz, which may again be attributed respiratory noise or breathing.

Figure 22E:
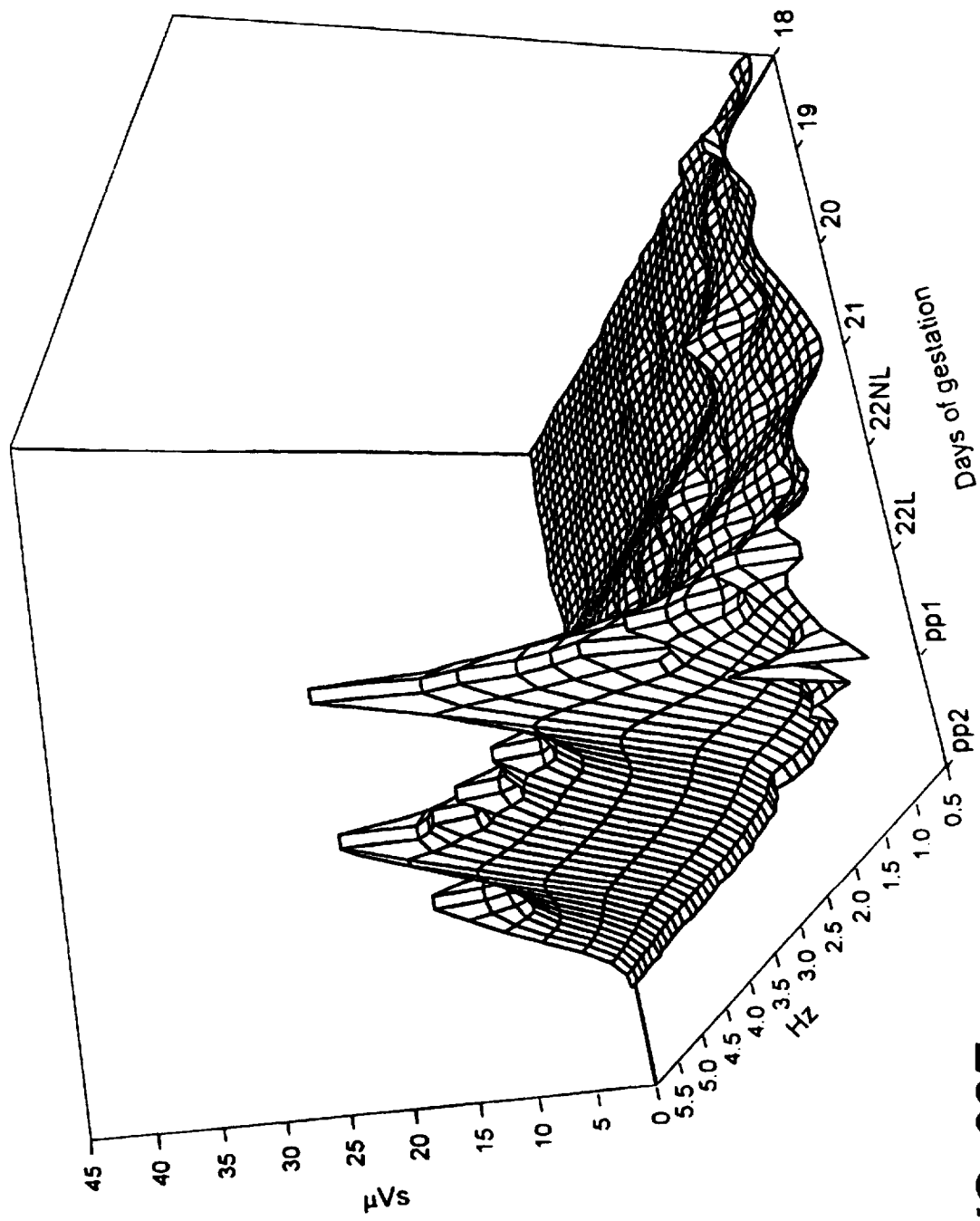

Referring to FIG. 22E, a mesh plot (energy levels vs. frequency vs. time of pregnancy) is shown that was prepared from many rats at different times in pregnancy. FIG. 22E shows that the energy level was very low (flat) prior to labor at days 18 to 22 NL (NL representing "non-labor"). Energy levels then rose sharply during labor at day 22 L (L representing "labor"). The energy levels then declined rapidly during postpartum days 1–2 pp (pp representing "postpartum"). Such data can be used as a basis for performing a predictive analysis of future uterine activity.

Figure 22F:
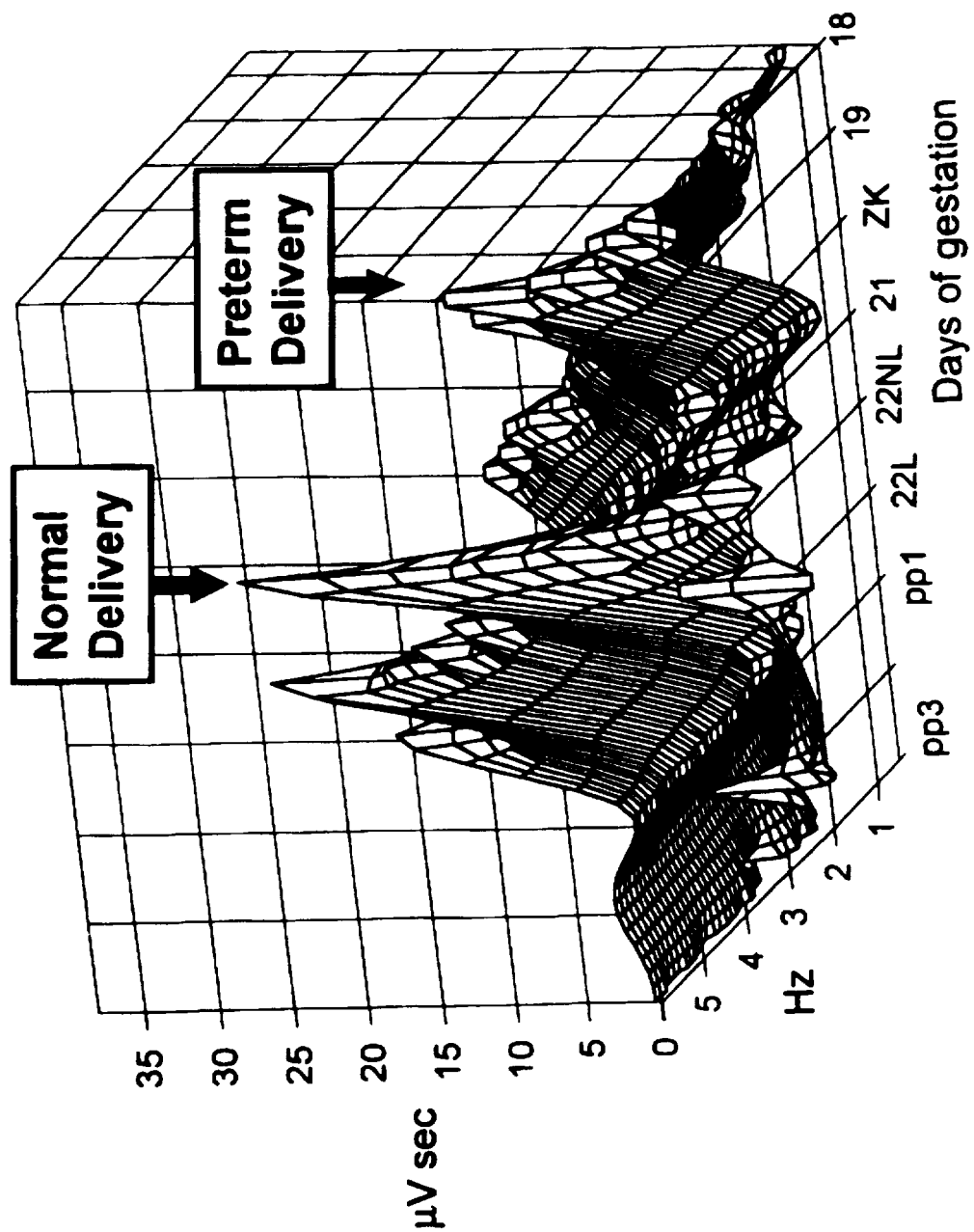

Referring to FIG. 22F, a combined mesh plot is shown. This mesh plot includes a mesh plot from EMG measurements from a rat for a normal delivery overlapped with a mesh plot from EMG measurements from a rat for a preterm delivery. Preterm delivery was achieved by treating a rat with ZK299 (onapristone) to induce preterm birth. As evident from FIG. 22F, energy levels for a forced preterm delivery were also greatly increased over a normal pregnancy as shown in FIG. 22E.

The data in FIGS. 22A–22F, therefore, show that power density spectral analysis of the EMG signals from bursts of action potentials may be used to predict when an animal is in term or preterm labor. The changes in the power density spectra from low to high levels reflect increased excitation and propagation of action potentials in the myometrium during labor and delivery. Thus, the spectral analysis provides a technique for indicating or predicting treatment during pregnancy. Further, these analyses may provide indications of other obstetrical diagnoses.

The techniques described above were also used to measure EMG signals of bursts of action potentials in pregnant women. FIGS. 23A–23G represent graphical depictions of power density analyses and a 3-dimensional mesh plot for EMG data measured from the uterine activity at a woman's abdomen surface.

Figures 23A, 23B:
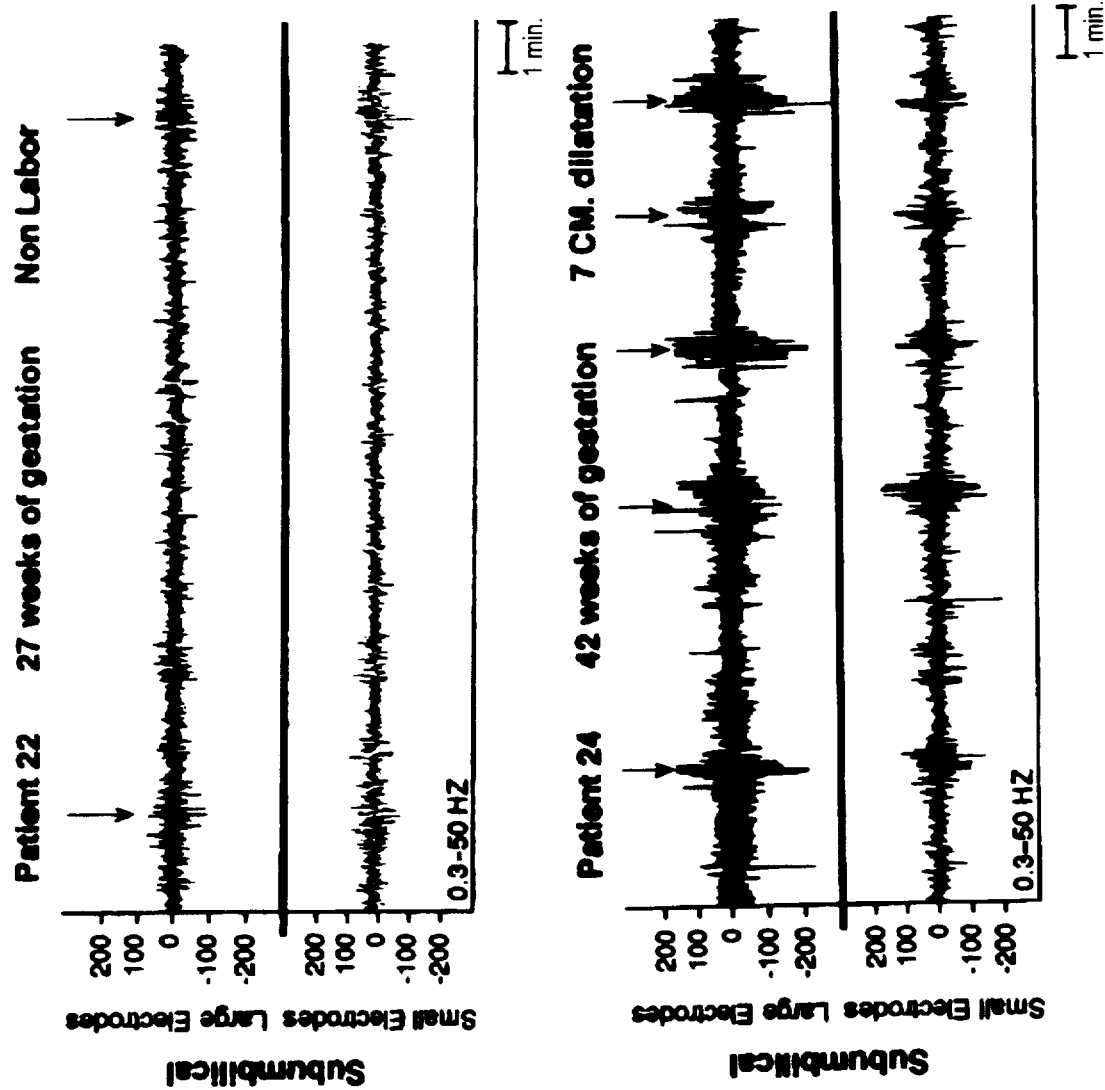
FIGS. 23A–23G are graphs of spectral analyses for bursts of action potentials recorded from a human abdominal surface.

FIGS. 23A–23B show electrical activity recorded from two sites on the abdominal surface in a patient at 27 weeks of gestation (FIG. 23A) and in a term laboring patient (FIG. 23B). The patient at 27 weeks was progressing normally and appeared for a weekly perinatal visit. She had worked all day and felt minor contractions that corresponded to the EMG activity (arrows in FIG. 23A). Eventually, this patient delivery a healthy boy at term. In contrast, the patient at term labor in FIG. 23B shows high amplitude and frequent (every ½ min.) EMG bursts. This patient delivered a normal baby girl about 30 minutes after the above record was made. Comparing 23A and 23B, it is evident that the frequency and amplitude of EMG bursts are quite different between the term and preterm patients.

FIGS. 23A–23B also provide duplicate readings. The first set was made using large electrodes. The second set was made using small electrodes. Both the small and large electrodes were found to be effective.

Figure 23D:
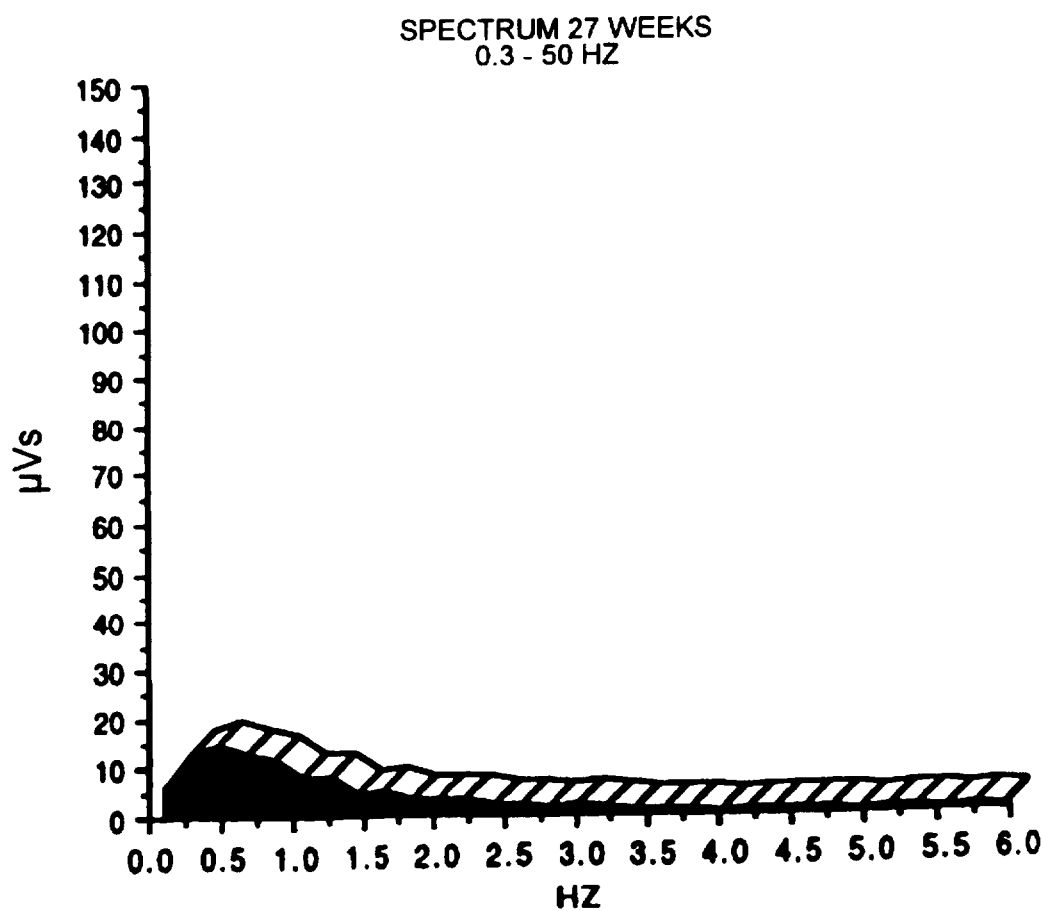
Figure 23C:
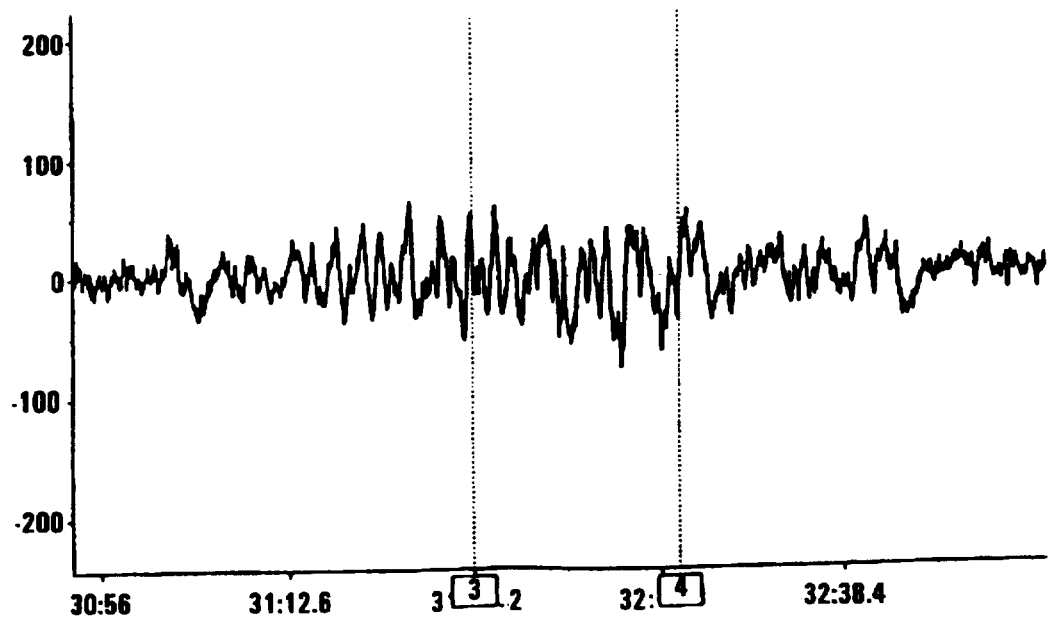
Figure 23F:
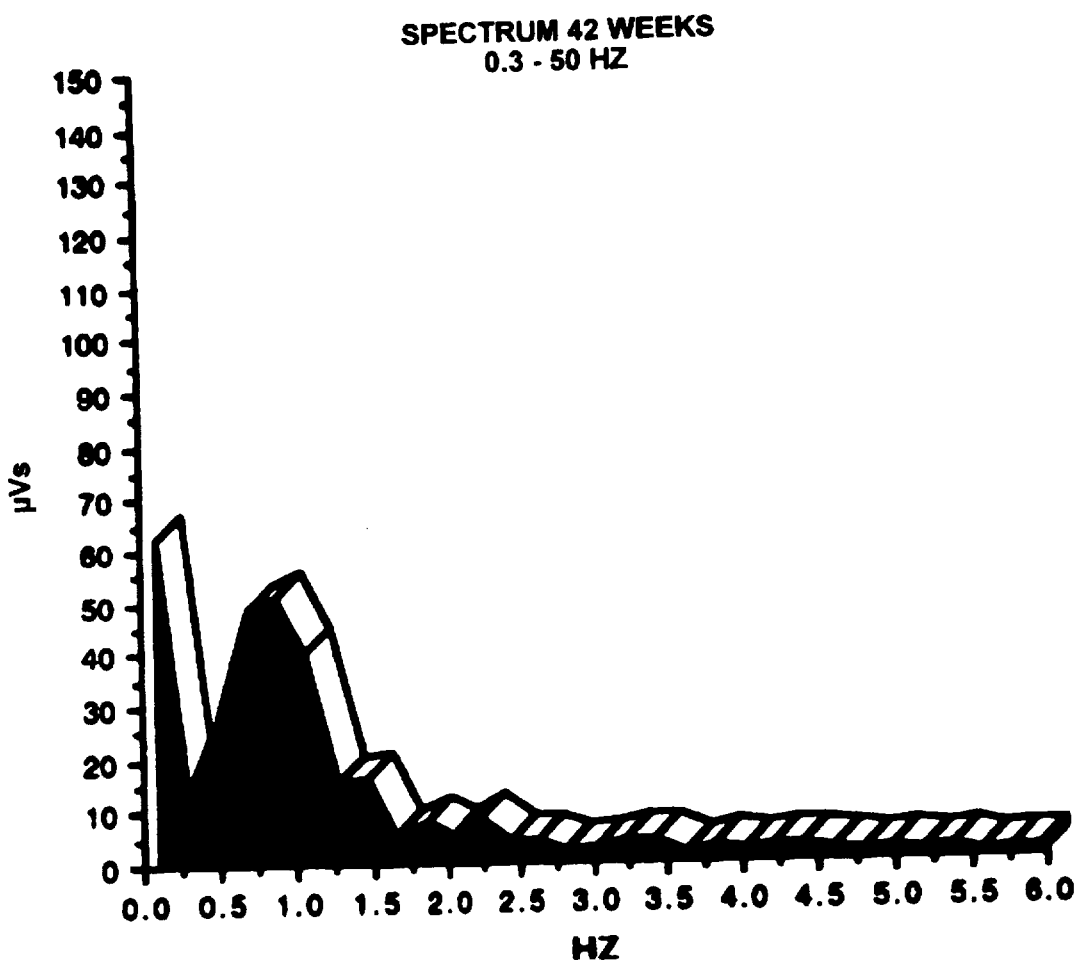
Figure 23E:
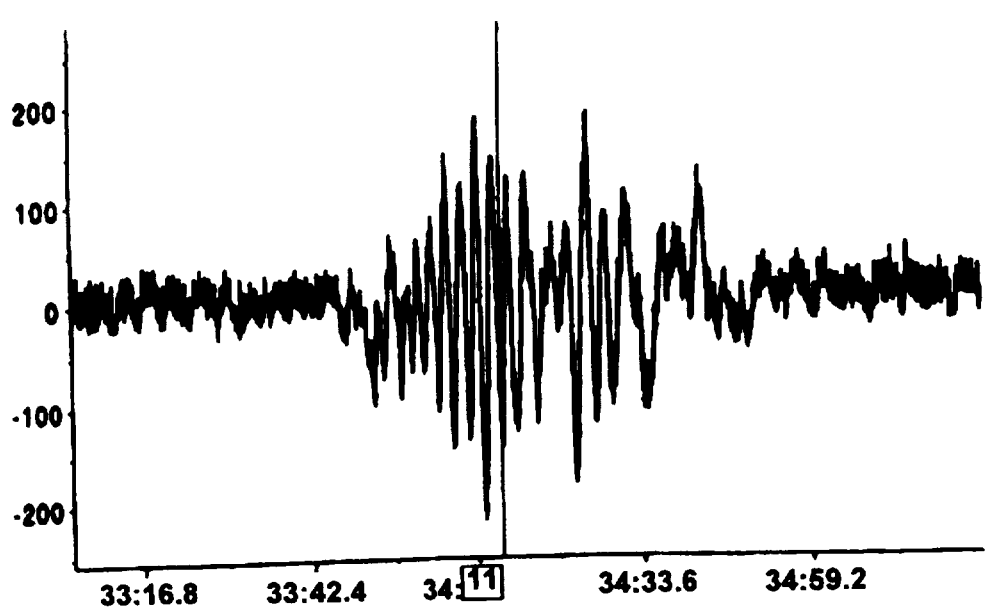

FIG. 23C shows a burst of action potentials from the EMG signal recorded from a pregnant woman at 27 weeks, where the woman was not in labor. FIG. 23E shows a burst of action potentials form the EMG signal recorded from a pregnant woman at week 42, where the woman was in labor. Only frequencies between 0.3–50 Hz in the EMG signal are shown in FIG. 23C and FIG. 23E.

FIG. 23D shows a power density spectral analysis of the burst shown in FIG. 23C. For a woman not in labor, no large frequency components are present. FIG. 23F shows a power density spectral analysis of the burst shown in FIG. 22E. In stark contrast to the frequency components present in FIG. 22D, large frequency components are present in FIG. 22F. Comparing the power spectrum analyses of the EMG bursts from the above patients (FIG. 23D and FIG. 23F), the bursts from the patient at 27 weeks gestation showed low energy levels (FIG. 23D), while the term labor patient demonstrated very high energy with a peak frequency about 1 Hz (i.e., 1 action potential per second) (FIG. 23F). It should also be noted that a large frequency component is present in FIG. 22F below 0.25 Hz, which may be attributed to respiratory noise or breathing.

Figure 23G:
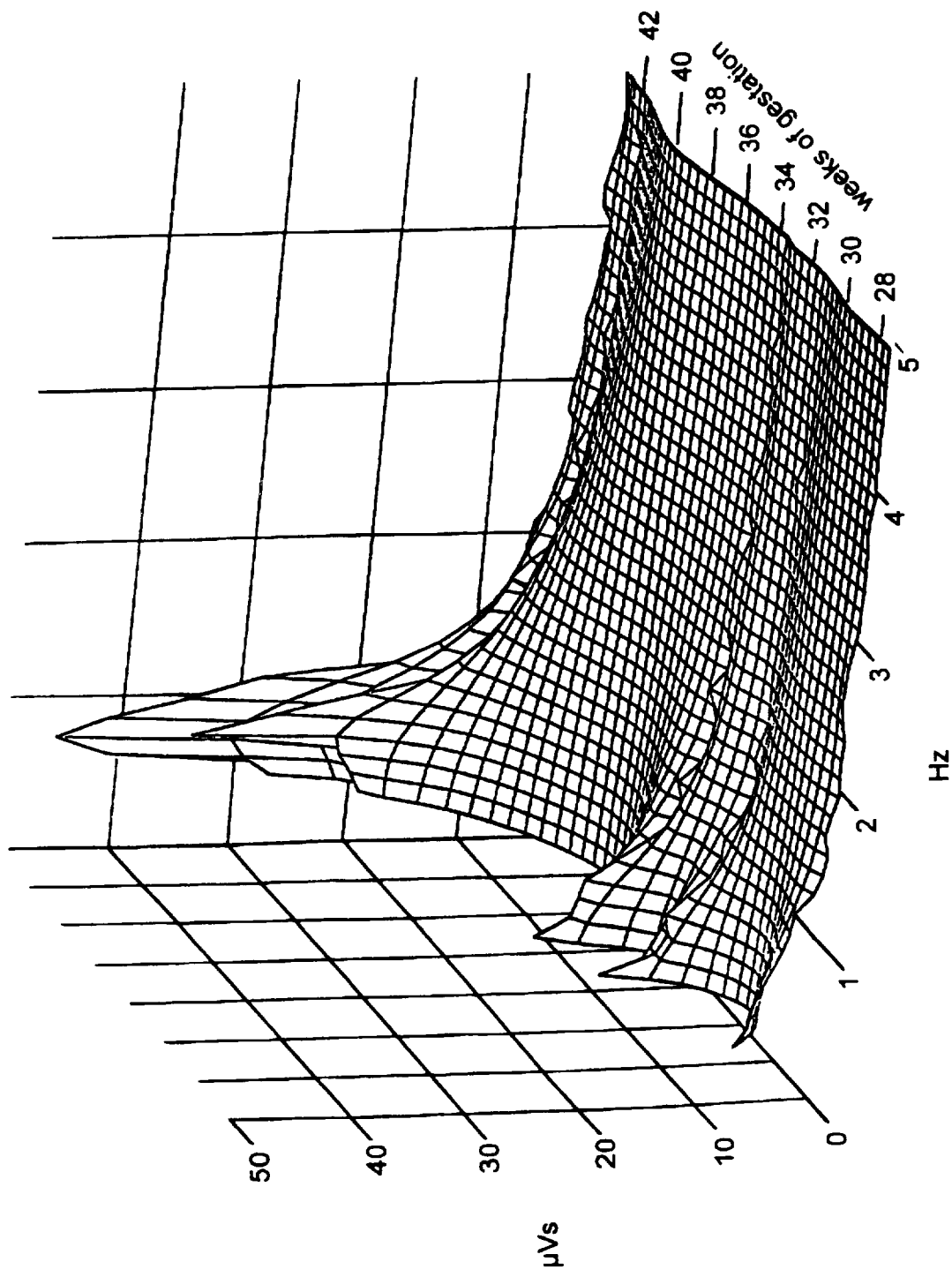

FIG. 23G shows a power density spectral mesh plot (energy levels vs. frequency vs. weeks of gestation) for EMG measurements of bursts of action potentials from a pregnant patient during gestation. Analysis of such data for many patients showed very similar results to the rat studies above (compare to FIG. 22E). In particular, it was found that the power density spectrum is relatively low (flat) prior to term labor, but rises dramatically during labor.

The above data indicates that spectral analysis of EMG bursts in women is of considerable value in evaluating the contractile state of the uterus during pregnancy. Information from these analyses can be used to dictate treatment. Patients at term with low power density spectrum score would not be expected to have passed through the series of steps necessary for excitation of the myometrium and, therefore, may require adjuvant treatment to augment labor. On the other hand, patients with a high score, normal for labor, would be predicted to progress without any treatment. The score may also be used to predict the likelihood of successful induction of labor with oxytocin at term.

Similarly, spectral analysis may be useful to foretell treatment and outcome of patients thought to be in preterm labor. Patients thought to be in preterm labor that have a low spectrum score might be expected to proceed normally to term. High spectral scores preterm should be coincident with true labor contractions and this information may lead to effective treatment to prevent preterm birth.

Spectral analysis may also be used to estimate the transition from low to high energy levels. Thus this technology may be helpful to monitor patients continuously in order to assess normal or abnormal progress. These methods will also be particularly useful for remote or "home" uterine recordings and monitoring. In this way, patients can easily be instrumented and monitored from a distance via a communications link, such as telephone lines.

Spectral data for many patients may be collected to provide a knowledge base from which to predict future uterine activity based upon one or more identified trends in a patient's examined uterine activity indicating parameters. In performing a predictive analysis an identified trend in the patient's examined uterine activity indicating parameters is compared to other trends in the knowledge base of an expert system. When matching trends are found between the patient's trends and trends in the expert system for an identified time period, $T_I$, a prediction is made regarding future uterine activity based upon how the matching trends in the knowledge base have behaved beyond time period $T_I$. In a preferred embodiment, a chaotic model of electromyographic activity may be used to predict future uterine activity.

2. Potential Vector Analysis Using Vectorhysterograms

A vector analysis of action potentials may also be used to determine useful parameters for obstetrical diagnosis. The uterine electromyogram is the result of electrical activity generated at the cellular level. The potential at any arbitrary point on the abdominal surface, back and sides from a pregnant woman may be measured and recorded, and the whole uterus can be modeled as a dipole vector. If the vector represents the spread of uterine myometrium excitation, the orthogonal component of the vector can be recorded. The orthogonal vector component $P_x(t)$, $P_y(t)$ and $P_z(t)$ of the vector P and its direction can be determined and analyzed.

a. General Principles

Body surface potential vector analysis is based on Frank's torso experiment model and research results. In the 1950's, Frank shaped a plaster cast of a subject's body, waterproofed it and filled it with saltwater. He then placed a dipole source composed of two electrodes on a rod within the torso model.

From measurements in such experiments, Frank found that the geometrical transfer coefficients that relate the dipole source to each point of the body surface potential $V_n(t)$. Thus for a set of k body surface potentials, there is a set of k equations that can be expressed in matrix from:

$$V = T * P.$$

Here, $V = \{v_1, \ldots, V_K\}^T; T = \{T_1, T_2, T_3\}; T_1 = \{t_{11}, \ldots, t_{1K}\}^T;$ $T_2 = \{t_{21}, \ldots, t_{2K}\}^T; T_3 = \{t_{31}, \ldots, t_{3K}\}^T; P = 55 \ P_x, P_y, P_z\}.$ V is a K*1 vector, T is a K*3 transfer coefficient matrix. P is the 3*1 time-varying dipole source vector.

Based upon this dipole analysis, and making the dipole source a uterus of a pregnant women, the potential at any point and at the same time can be measured to obtain the orthogonal vector component of the action potentials on an XYZ axis. FIG. 24 illustrates the placement of electrodes on a patient, and a 3-dimensional position of electrodes located on an XYZ axis.

When acquiring the six point potential at any time, the vector component on X, Y axis at this time is also obtained. That is:

$$P_x(t) = V_{x1}(t) - V_{x2}(t);$$
$$P_y(t) = V_{y1}(t) - V_{y2}(t);$$
$$P_z(t) = V_{z1}(t) - V_{z2}(t);$$

It is noted that the direction is that the vector points toward the electrode with higher potential. For example, if $P_x>0$, then the direction is in X positive direction.

b. EMG Signal Recording and Noise Canceling po Six bipolar pairs of Ag—AgCl beckman electrodes may be used. Other electrodes may be used, such as unipolar, tripolar, etc. They may be arranged on the abdominal surface, sides and back of a patient, as shown in FIG. 24. It is also possible to use a fewer or a greater number of electrodes, as shown in FIG. A. An abdominal sheath (A1) shown in FIG. A is embedded with an array (A2) of electrodes (A3) from which EMG signals are collected for further processing. In other embodiments the coverage of the sheath may be less than or greater than shown here, so that sheath may reach around the back of the patient and higher or lower on the pelvis and torso, and the number of electrodes may be greater than or less than illustrated here and the electrodes may be selectable. An ECG electrode may also be included for purposes of noise reduction.

At each point the system records the EMG signal corresponding to the uterine contraction. A Maclab digital signal processing system is used to acquire the EMG signals at each point. The EMG signal at each point will likely be contaminated by noises. The Adaptive Noise Canceler (ANC) and Adaptive Line Enhancer (ANE) may be used to cut off the noises, as discussed above.

C. Analysis

Six channel EMG signal segments are selected to correspond to the mechanical contact segments of the uterus. Data is then saved into one data file. The data file is then analyzed.

To analyze the data, the orthogonal vector components $P_x$, $P_y$ and $P_z$ are acquired. According to the orthogonal vector component direction, the tracing of uterine potential vector P(t) can be divided into 8 areas in a 3-dimension space. The rules are as follows:

| $P_x(t)$ | $P_y(t)$ | $P_z(t)$ | Area No. |
|---|---|---|---|
| + | + | + | 1 |
| − | + | + | 2 |
| − | − | + | 3 |
| + | − | + | 4 |
| + | + | − | 5 |
| − | + | − | 6 |
| − | − | − | 7 |
| + | − | − | 8 |

Figure 25:
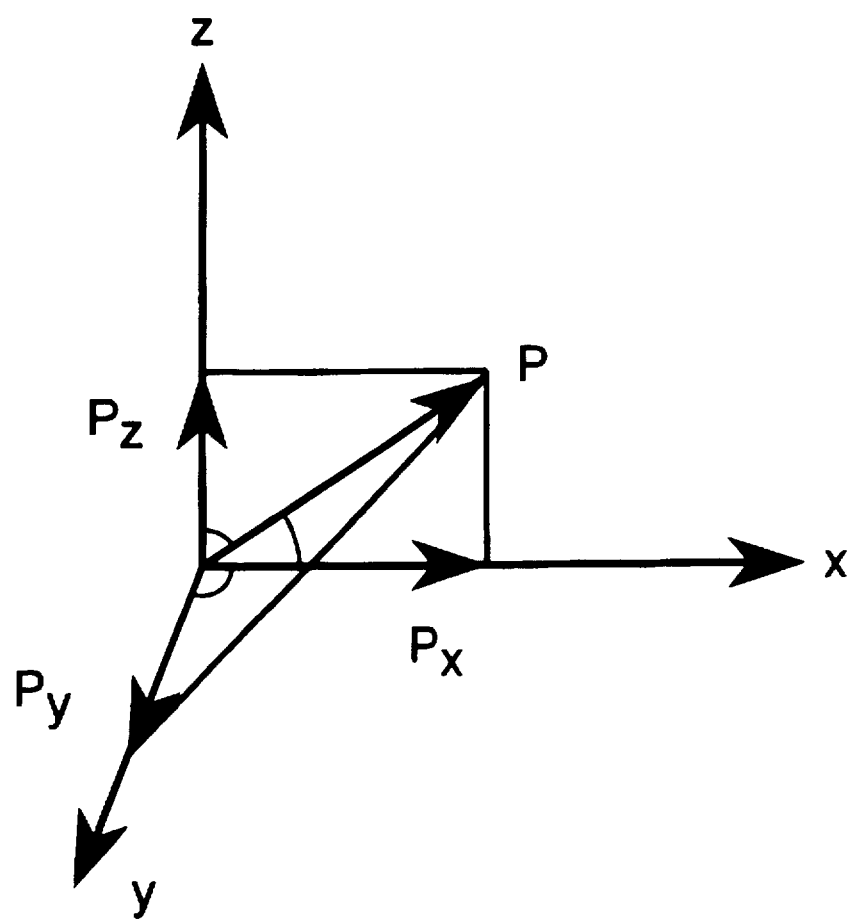
FIG. 25 is an illustration of a potential vector.

At each sample time, the system will calculate the direction vector $\{\phi_x, \phi_y, \phi_z\}$ of uterine potential vector P(t) as shown graphically in FIG. 25. $\phi_x$ is the angle of vector P(t) with X axis in 3-dimension. $\phi_y$ is the angle of vector P(t) with Y axis in 3-dimension. $\phi_z$ is the angle of vector P(t) with Z axis in 3-dimension. The formula of calculating the angle is as follow:

$$\phi_x = \cos^{-1}(|P_x|/(|P_x|^2 + |P_y|^2 + |P_z|^2)^{1/2});$$

$$\phi_y = \cos^{-1}(|P_y|/(|P_x|^2 + |P_y|^2 + |P_z|^2)^{1/2});$$

$$\phi_z = \cos^{-1}(|P_z|/(|P_x|^2 + |P_y|^2 + |P_z|^2)^{1/2});$$

The present system may display the vector P(t) tracing in 3-dimension on a computer screen. The user can select the demonstration speed that controls the tracing on screen. When the lower speed is selected, the details of the tracing changes at each sample time can be easily observed. The system supports another method to assist the user to analyze the changes in progression of P(t) at each sample time. At each sample time $t_i$, the system will determine which area vector $P(t_i)$ should be in according to the rules of area division. The system will draw out the change in progression in order of P(t) as follow:

| Time: | $t_0$ | $t_0 + \Delta t$ | $t_0 + 2\Delta t$ | $t_0 + 3\Delta t \ldots$ |
|---|---|---|---|---|
| Order: | 1 to | 3 to | 5 to | 6 to ... |
| Angle: | {12,24,53} to | {23,54,12} to | {3,23,15} to | {13,34,60} to ... |

The results can be printed on a printer. Using this method the vector of activity can be defined, and the origin and spread of activity may also be defined. Using this technique, pacemaker regions and direction of propagation of uterine electrical activity may be identified. These parameters may then be used to predict treatment of pregnant women or to make other obstetrical diagnoses.

3. Other Data Analysis Techniques

As would be obvious to one of skill in the art, other analytical techniques may be utilized to analyze the uterine electrical activity data described above.

Figure 24A:
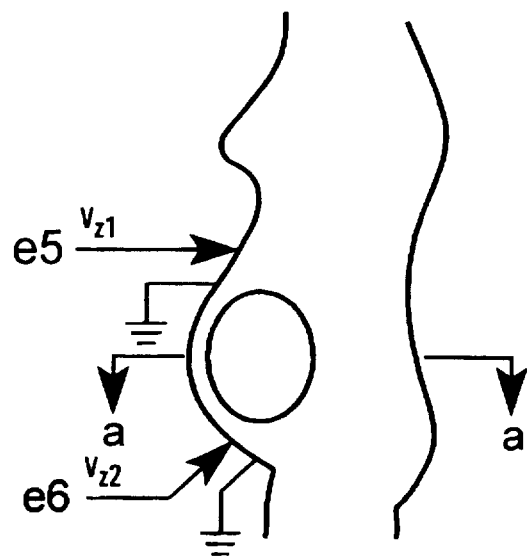
FIG. 24A is a side view of a patient showing the placement of electrodes used for vector potential analysis in the vertical dimension.
Figure 24C:
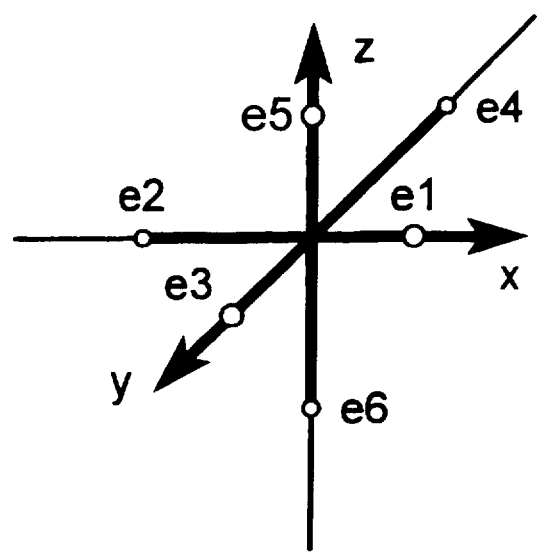
FIG. 24C is a graphic representation of the spatial relationship of the electrodes shown in FIGS. 24A–24B.
Figure 24B:
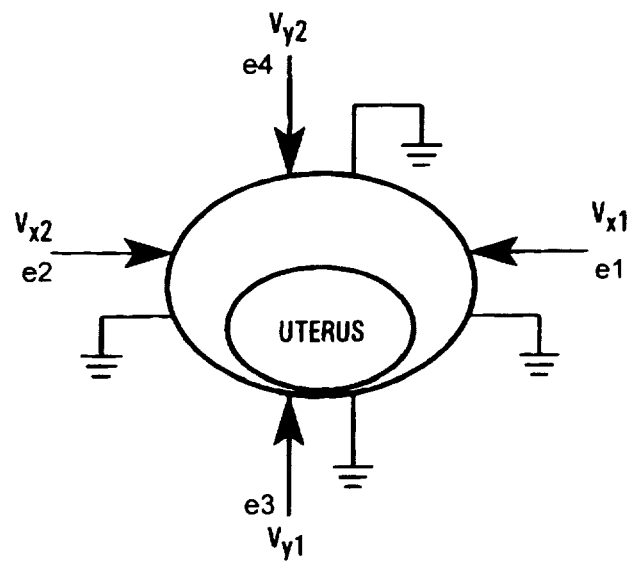
FIG. 24B is a top view of the patient shown in FIG. 24A, along axis a—a, and showing the placement of electrodes used for vector potential analysis in the x-y place containing axis a—a.
Figure 27:
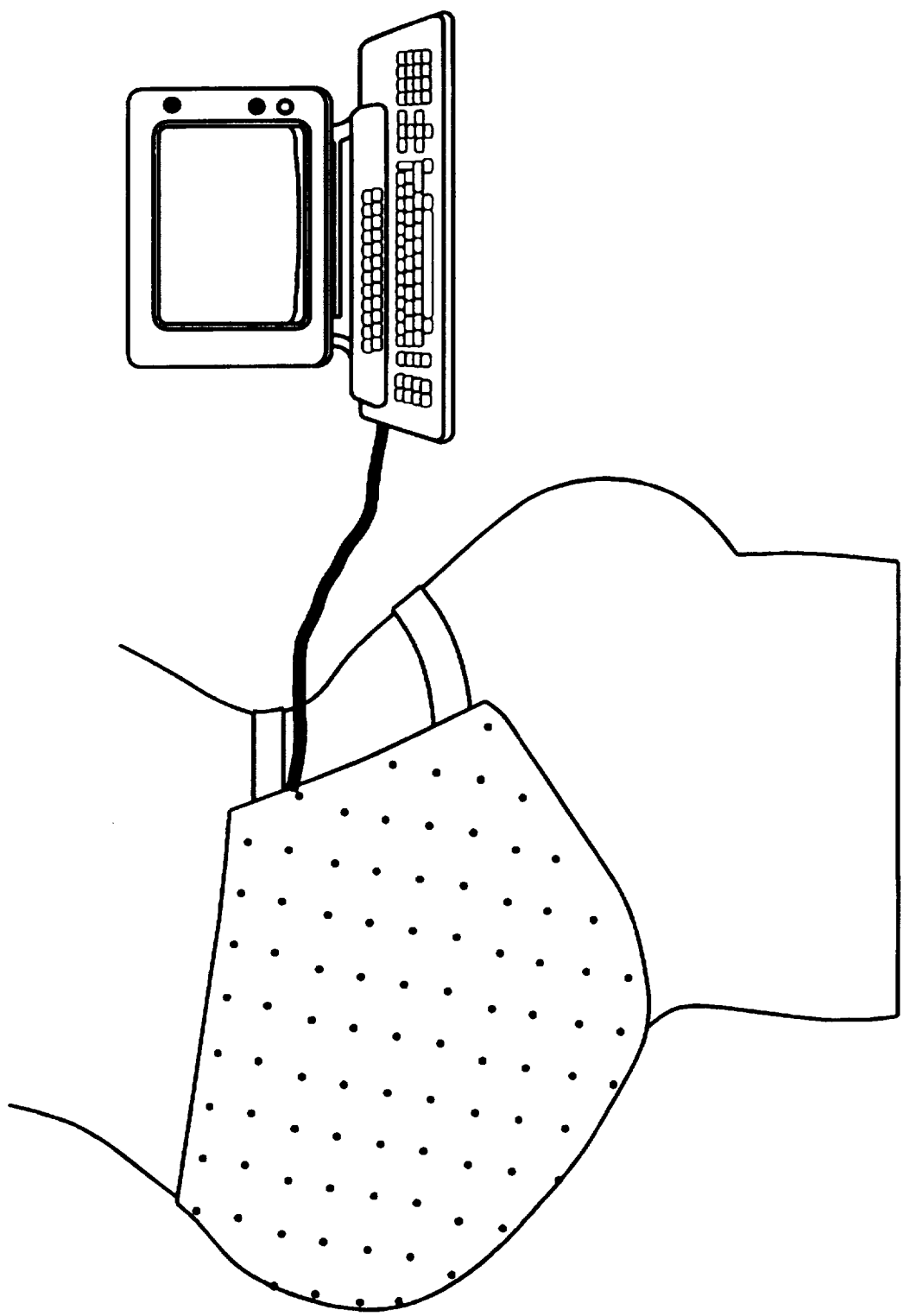
FIG. 27 is a left side view of a patient wearing an abdominal belt embedded with a multi-electrode array for determination of uterine potential vectors in two or three dimensions.
Figure 28:
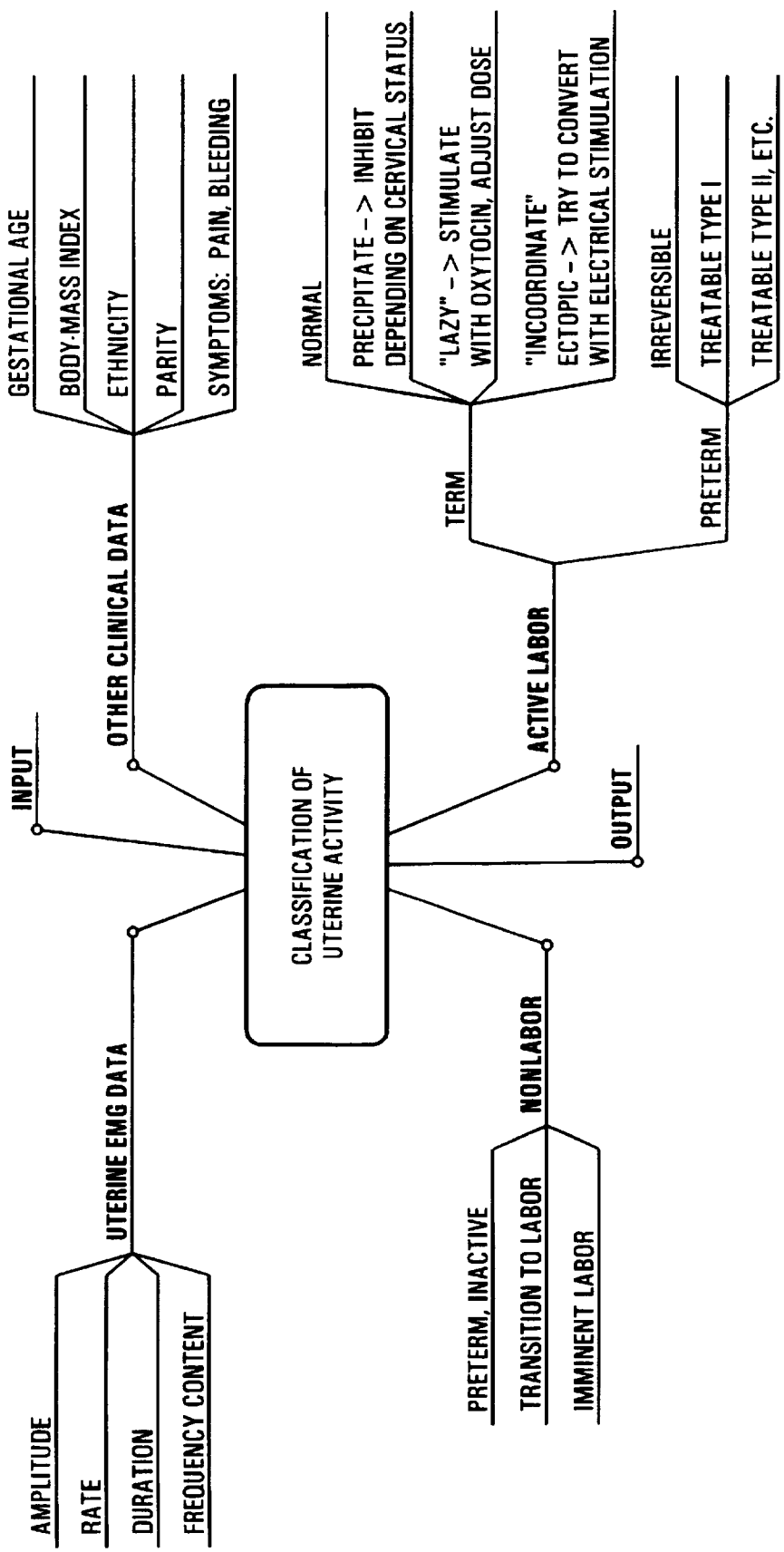
FIG. 28 is a decision tree diagram for classification of uterine activity.
Figure 29:
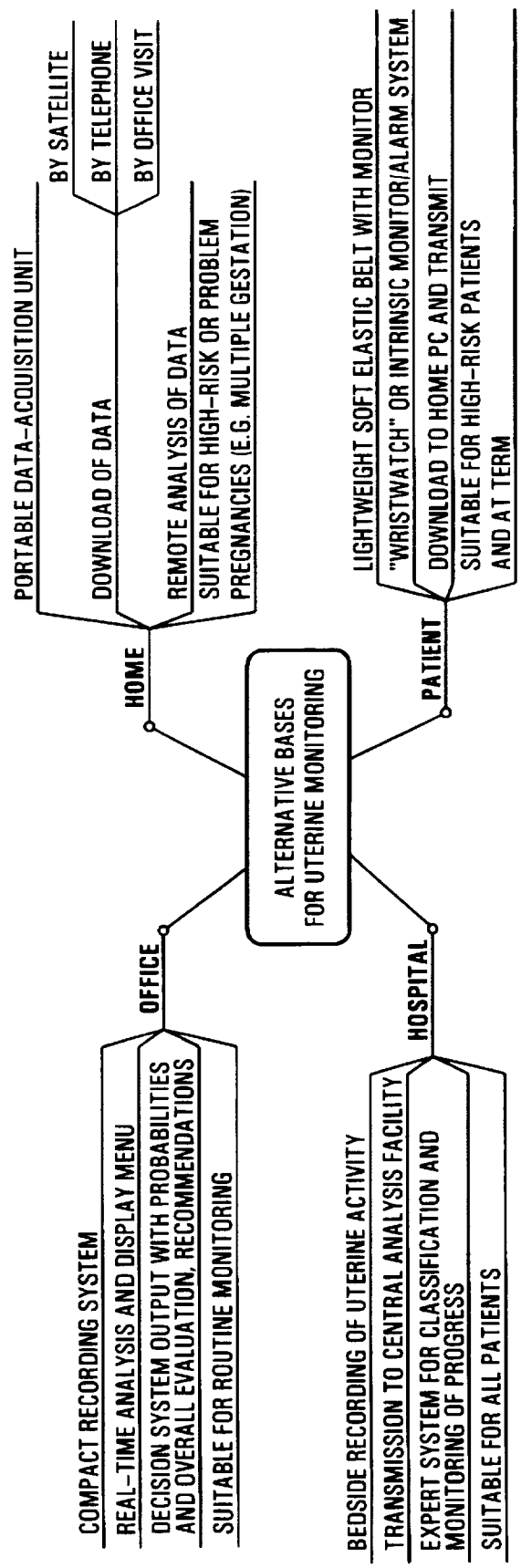
FIG. 29 is an alternative configurations of uterine monitor for hospital, office, home, and patient-based modes.

Using multiple electrodes as shown in FIGS. 24A–24C, a field of vectors representing activity at various points on the uterine surface can be constructed. This information can be used to characterize the behavior of the electrical activity locally by mapping the vector at each point onto an ovoid surface. The appearance of the map may be useful in staging labor or prelabor and in identifying conduction anomalies. In addition to providing information about overall conduction, this data will also evaluate the homogeneity of the electrical behavior at a number of locations on the surface of the uterus. These data can help to localize excitation spots and dead zones. In a preferred embodiment, electrodes e1–e6 can be affixed to a belt that is worn by the patient, as shown in FIG. 27.

One alternative technique is to integrate the energy measured for a burst of action potentials. Using this technique, the electrical signals in a burst of action potentials recorded from the uterus are first squared, then summed and the total area under the curve is then integrated. This analysis gives a rough estimate of the energy within a burst of action potentials. It does not, however, account for the length or time component of the data measured. Thus, this analysis could be extended by further dividing the approximate total energy for the burst of action potentials by the total time of the burst to determine the integrated function/time value or energy per unit time for the burst.

Figure 30A:
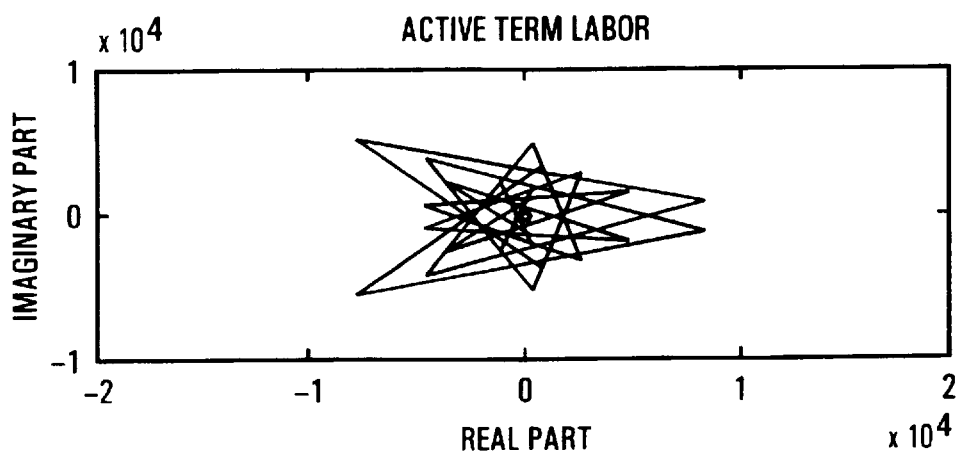
FIGS. 30A–30B are plots of phase as well as amplitude information in the analysis of uterine EMG.
Figure 30B:
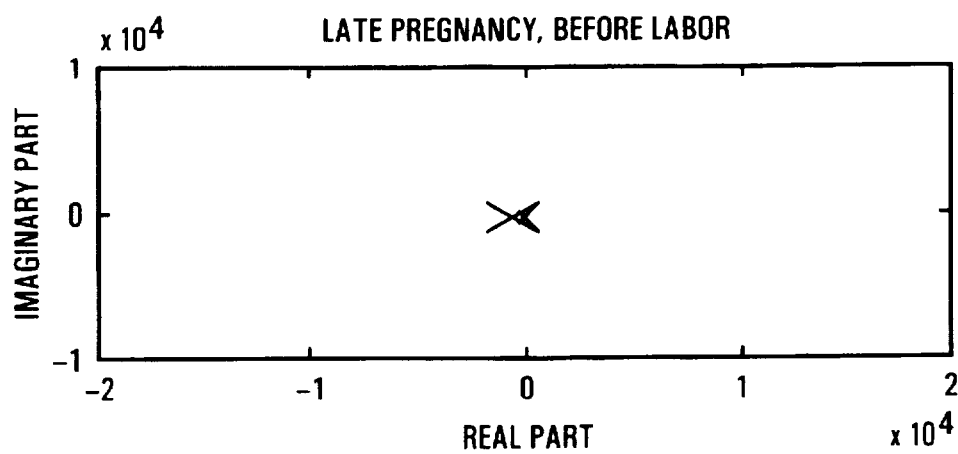

Phase information may also be applicable to the analysis. In FIGS. 30A-30B, both phase and amplitude information are presented. In each panel, the two components of the FFT, real and imaginary, have been plotted for each frequency. Each point represents the FFT at a given frequency. Consecutive points, which are joined by lines, represent values at, for example, 1 Hz, 2 Hz, 3 Hz, and so on, up to the maximum frequency. Although it is not apparent in such a plot which point corresponds to which frequency, one can identify sequential points. The amplitude information is given by the distance of each point from the center of the graph; the phase information is given by the angle with respect to the real axis. These plots show that the active term data is characterized by having frequency components of large amplitude at a plurality of different frequencies, equivalent to saying that the power spectrum is broad. The points jump around rapidly from quadrant to quadrant, so there is no simple way to describe the phase pattern for successive frequencies. (The top and bottom half of each graph are mirror images because of the symmetry of the FFT.) The net result is to produce a star-like pattern during active labor. The data before labor has much smaller power (or amplitude) at each frequency, and fewer frequencies have significant power. Therefore, the pattern is necessarily much simpler. This analysis was constructed using the fft and plot commands in Matlab. For each top panel, the pattern produced by one muscle action potential (256 points at 200 Hz) in rat uterus is shown (raw data in bottom panels).

Another technique that may be utilized is a fast wavelet transform technique. This technique could be adapted from that described in Cody, *The Fast Wavelet Transform*, Dr. Dobb's Journal (April 1992); Cody, *A Wavelet Analyzer*, Dr. Dobb's Journal (April 1993); and Cody, *The Wavelet Packet Transform*, Dr. Dobb's Journal (April 1994); for ECG, see A. Djohan, T. Q. Nguyen and W. Tompkins, "ECG Compression using Discrete Symmetric Wavelet Transform," International Conf. EMBS, Sept. 1995; Sri-KrishnaAditya, Chee-Hung H. Chu, and Harold H. Szu, "Application of adaptive subband coding for noisy bandlimited ECG signal processing", SPIE Proceedings Vol. 2762, pp. 376–387).

One objective of wavelet analysis, like Fourier analysis, is to re-express data in terms of frequency content (or the equivalent). Wavelet analysis belongs to a general set of approaches called time-frequencyanalysis. Unlike Fourier frequency analysis, time-frequency analysis determines the "instantaneous" frequency content at each time point and is more appropriate for signals whose frequency characteristics clearly change with time. The continuous wavelet transform essentially describes the signal in terms of all possible frequencies, or scales.

In FIGS. 31A-31D, action potentials from active term labor or nonlabor are analyzed by this method. Analysis of rat uterine EMG data was carried out using the continuous wavelet transform (CWT) and the wavelet function "db10". The Wavelet Toolbox of the Matlab software suite was run on a 66 MHZ computer comprising a Pentium® microprocessor. The CWT yields a three-dimensional decomposition of the electrical activity. One axis in FIGS. 31A-31D is "time". The second axis, referred to as "scale", provides information analogous to "frequency" in the discrete Fourier transform (DFT). Smaller values of the "scale" translate into high frequencies, larger into the slower frequencies. The z-axis values are the wavelet coefficients, analogous to the amplitude of the DFT, being proportional to the frequency content detected.

Figure 31C:
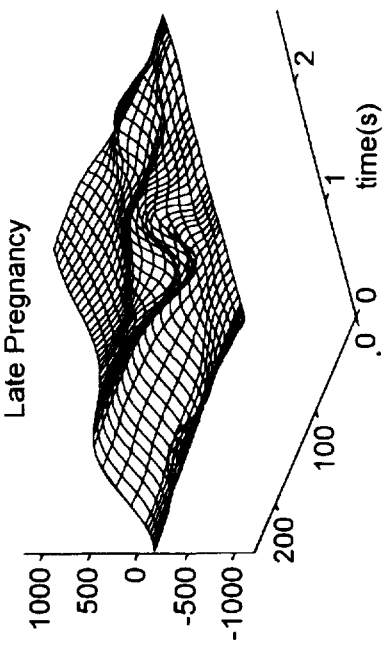
FIGS. 31A–31D are plots of rat uterine contractility during labor and nonlabor using the continuous wavelet transform.
Figure 31A:
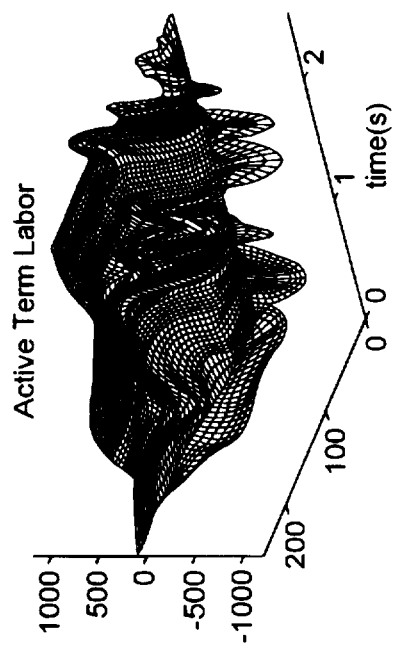
Figure 31D:
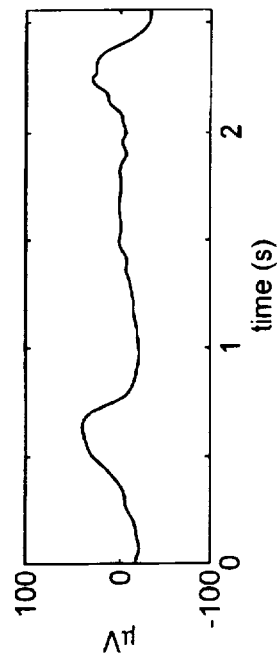
Figure 31B:
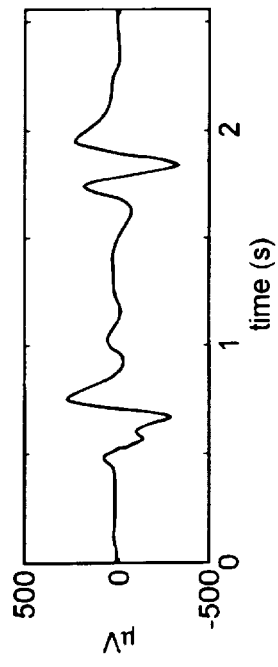

Like other "spectrogram-type" methods, such as joint time-frequency analysis, a primary advantage of this type of analysis is the localization in time of nonstationary frequency behaviors. FIGS. 31A-31D show the "instantaneous" frequency content. The key difference between the labor and nonlabor is seen at low values of scale, equivalent to high values of frequency. During labor, many peaks are seen at low values of scale but during nonlabor, the surface is essentially flat at the same values of scale. Based on the multiple large peaks at small scale values, it is apparent that the "active labor" sample (left) contains much more high frequency activity, occurring during the muscle action potentials, than is present in "late pregnancy" (right). In FIGS. 31B and 31D the voltage scale differs between the two bottom panels and the data was acquired at 200 Hz .

The discrete wavelet transform (DWT) may also be used to analyze the data. The DWT takes advantage of the striking mathematical properties of wavelets to greatly reduce the number of scales needed. The discrete wavelet transform, splits the signal, roughly speaking, into two parts, equivalent to processing with a high-pass filter and a low-pass filter, and the process is iterated, although only on the output from the low-pass filter.

Figure 32A:
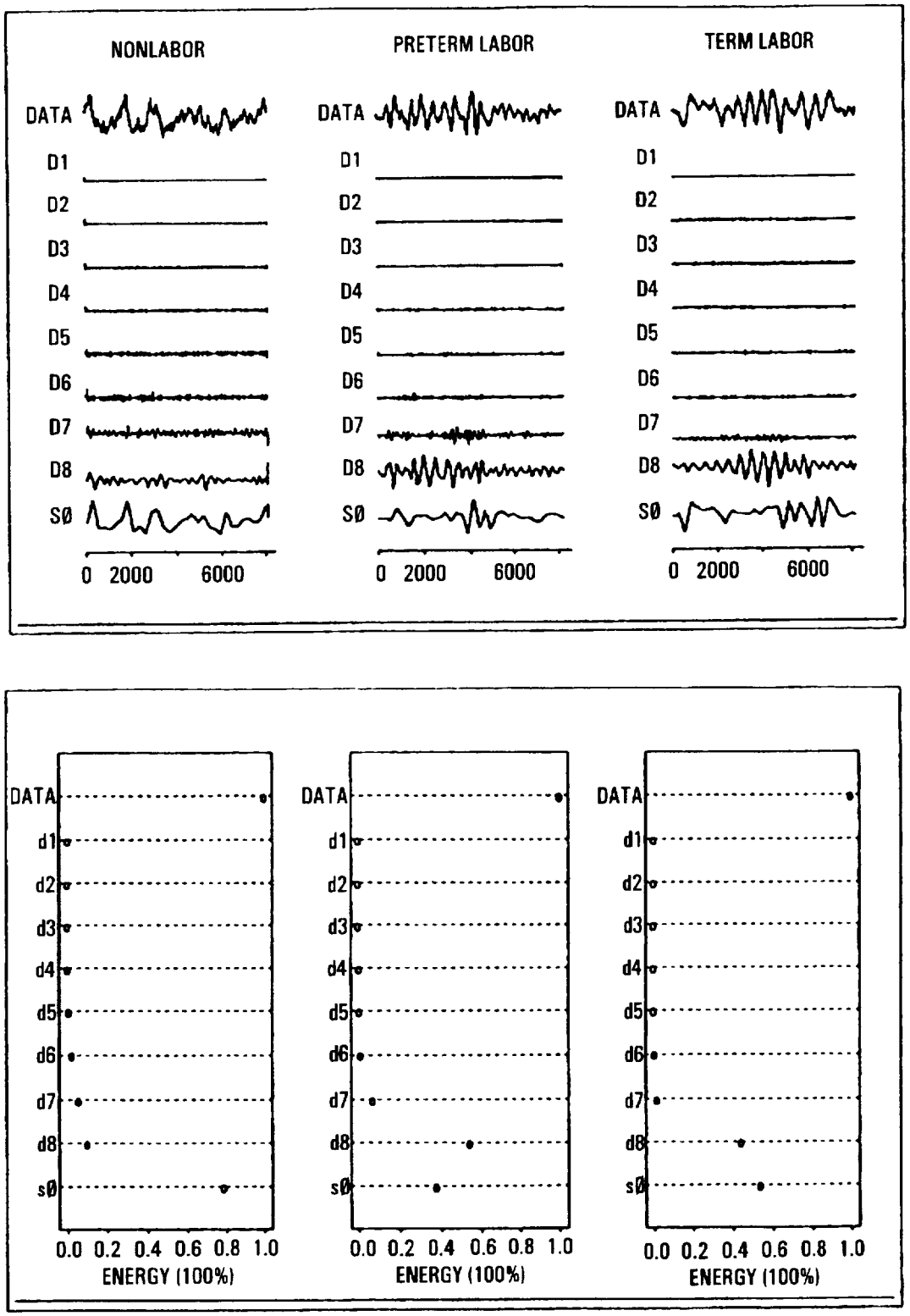
FIG. 32A shows analysis of human uterine contractility during nonlabor, preterm labor, and labor using the discrete wavelet transform.

FIG. 32A shows data from women during nonlabor, preterm labor, and term labor. In the top half of the figure, the original data along with the decorrelated output for an eight-level discrete wavelettransform using the "s8" wavelet. The bottom scale corresponds to number of points, where data was acquired at 200 Hz. The term and preterm labor differ from nonlabor in the proportion of activity in different subbands. S8 shows the "smooth" part of the signal in each case. D1 to D8 are the details at each level. The bottom half of the figure shows the fraction of the total energy in the signal in each subband. During nonlabor, approximately 80% of the energy is contained in S8. During labor, this energy is split roughly equally between S8 and D8, which contains the next highest frequency subband. Before labor the S8:D8 ratio is approximately 8; during preterm or term labor it is close to one. In the examples shown, little high frequency noise may be observed in the other channels. This data was previously denoised by the wavelet shrinkage technique. All processing was carried out using the S+ wavelets program.

A generalization of this process, which iterates the filtering on either or both of the high-pass and low-pass outputs at each stage, is called wavelet packet analysis. Wavelet packet analysis does not limit subband processing to the low-pass signals, but lets you focus, by selecting the right "tree", on any frequency band you wish. An example is shown in FIG. 32B using rat data. In this case data from rat myometrium at either day 20 (left top panel) or delivery (right) was decomposed using a more elaborate tree (center). The bottom panels show the difference between the channel marked "2.1" for preterm and term uterus. The spikes on either end of the trace should be ignored; these are "edge effects." The action potential activity at delivery is clearly detected on this channel, whereas the same channel is essentially blank. Thus either the DWT or wavelet packet analysis may be used for detecting the new high-frequency components which characterize labor. Wavelet packets may help to breakdown activity into finer subbands. In addition, each of these approaches can be used to compress the EMG signal with high efficiency before storage.

A still further technique that may be adapted and utilized is a joint time-frequency analysis according to Gabor or windowed Fourier analysis. These techniques could be implemented utilizing the LabVIEW and the Joint-Time Frequency Analysis (JFTA) Toolkit available from National Instruments, Austin, Tex. A still further technique is cosine packet analysis. This technique may also be implemented using the S+ Wavelets program.

Figure 33:
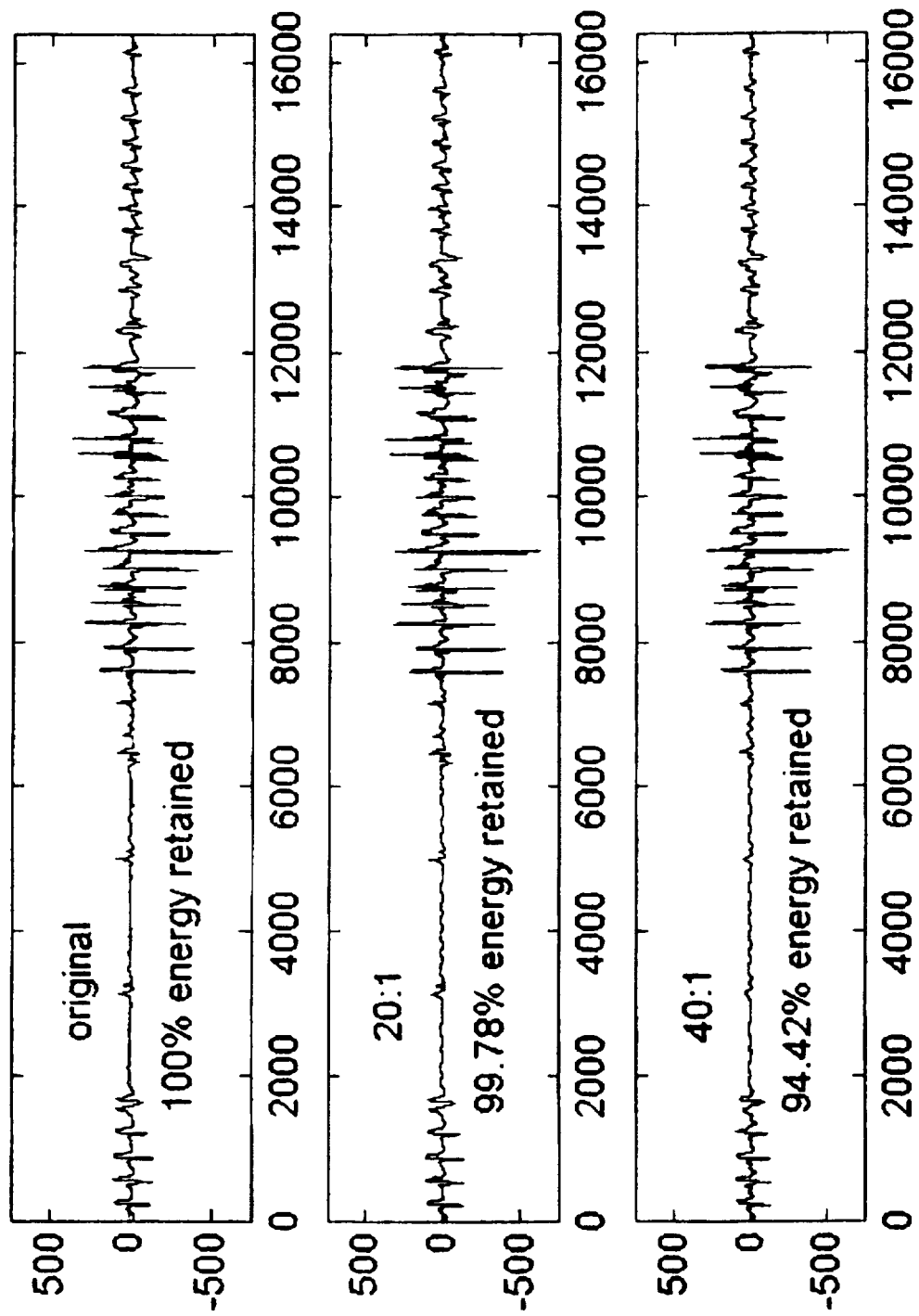
FIG. 33 is a plot of Wavelet Compression for Uterine EMG.

FIG. 33 shows an example of wavelet-based compression of the EMG. Using the "wavemenu" program of the Matlab Wavelet Toolbox (and the wavelet function "db10"), data was compressed by thresholding so that out of 100% (raw data), only 5% (20:1) of the wavelet coefficients, or only 2.5% (40:1) of the wavelet coefficients, were nonzero. With only the largest 2.5% of the wavelet coefficients retained, the signal is little distorted, especially for the largest action potentials which occur during a burst. A corresponding procedure can be used for denoising of signals. The x axis refers to the number of points in the original signal (16K). The acquisition frequency was 200 Hz. As the number of retained coefficients becomes smaller, a limiting situation occurs where one coefficient remains for each large action potential. In thise case, the largest coefficients are located at large action potentials and these coefficients therefore identify the large action potentials. Changes in the shape of action potentials can be reflected in the "scale" of the wavelets whose coefficients are the largest.

Figure 34A:
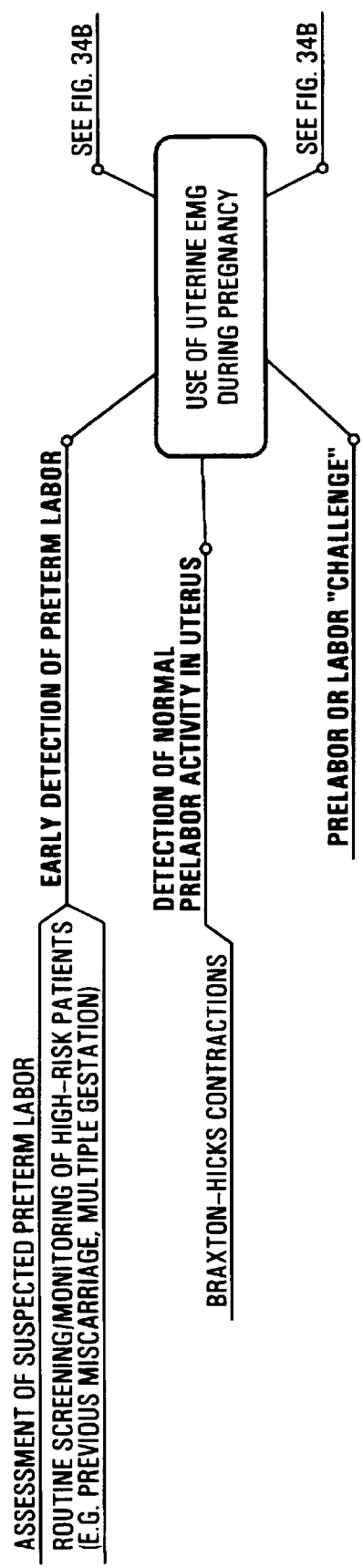
FIGS. 34A–34B are diagrams which show the spectrum of possible clinical applications in pregnant patients.
Figure 34B:
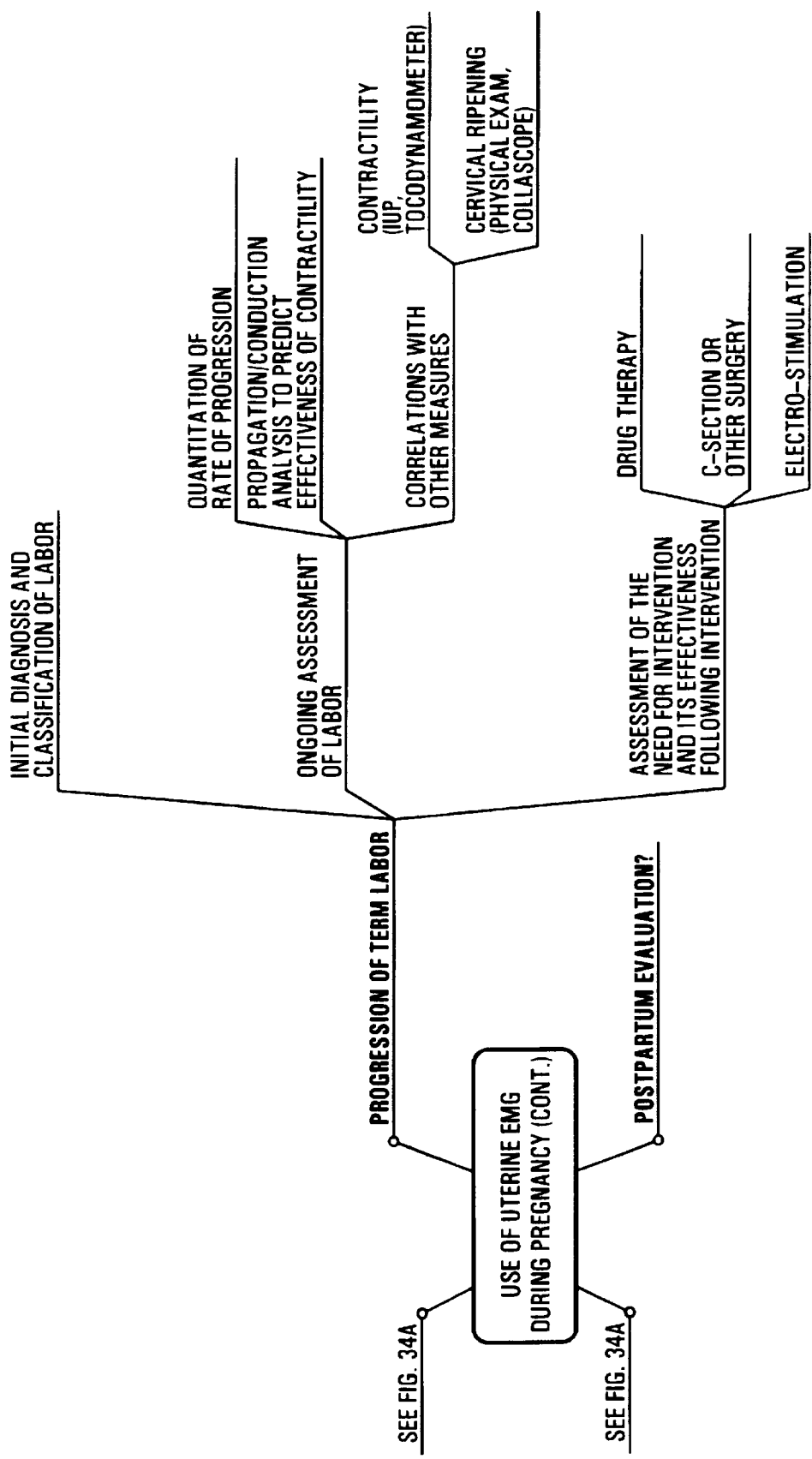

FIG. 34 illustrates the use of the uterine EMG signal analysis during pregnancy. Because some isolated contractions occur throughout pregnancy, these methods could be used to analyze the mild patterns of contraction (i.e. Braxton-Hicks contractions) that presage normal labor. Mild contraction patterns during pregnancy may also provide the opportunity to study patterns associated with incipient preterm labor and enhance the ability to diagnose preterm labor at an early stage in high-risk populations. This methodology could also be used to assess the uterine response to "a challenge," a test dose of an excitatory agent such as oxytocin, as a measure of the overall readiness to labor.

Once labor has begun, the EMG signal analysis method taught by the present invention will be useful in diagnosing, assessing treatment options, and in predicting the course of labor. This may also be combined with conventional clinical methods, such as intrauterine pressure measurement. The methods of EMG signal analysis taught by the present invention may also be useful postpartum in assessing the regression of uterine activity.

Figure 35:
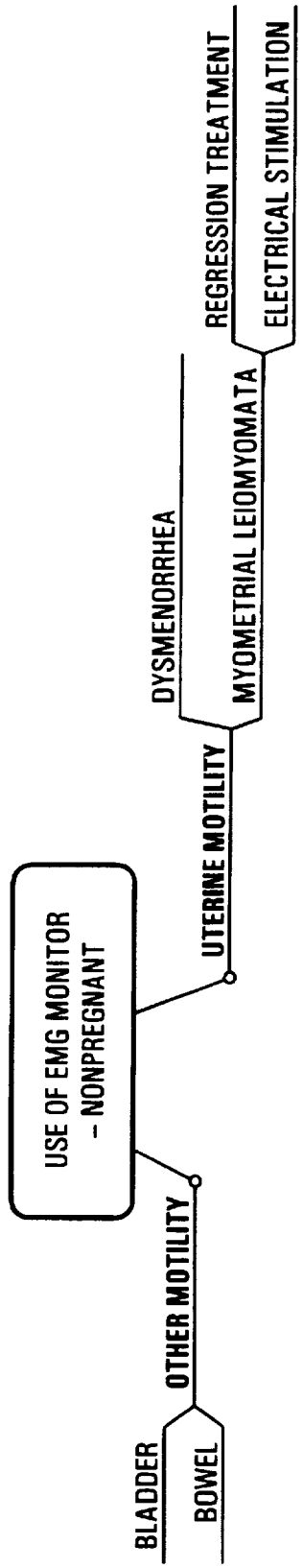
FIG. 35 is a diagram which shows the spectrum of possible clinical applications in nonpregnant patients.

FIG. 35 indicates the uses of the present invention for non-pregnant women and men. There are some disorders of uterine contractility or motility that occur outside pregnancy. One of these is dysmenorrhea. It is caused by cramping during parts of the menstrual cycle. Another important disorder is due to smooth muscle tumors ("fibroids" or leiomyomata) in the myometrium. This disorder tends to be hyperexcitable compared to normal myometerium and can be very painful. Often, women are treated with hormones to produce regression of these tumors. Functional regression of such tumors may be montbred and analyzed with the present invention. Other smooth muscle organs in both men and women such as bladder and bowel, also show spontaneous activity which could be monitored and analyzed with the present invention.

While the present invention has been presented with reference to particular embodiments, it will be understood that additions, deletions and changes to these embodiments may be made without departing from the spirit and scope of the present invention.

What is claimed is:

1. A method for characterizing uterine electrical activity, comprising:
   a. applying action potential measuring electrodes to an abdominal or vaginal (or cervical) surface of a patient;
   b. acquiring analog electromyographic signals transmitted through said electrodes, at a sampling frequency between about 0.5 and 1 kHz, for a duration of time sufficient to record at least one burst of action potentials;
   c. amplifying said electromyographic signals;
   d. storing acquired electromyographic signals, including at least one burst of action potentials;
   e. analyzing uterine activity indicating parameters from at least one burst of action potentials within the stored electromyographic signals; and
   f. characterizing uterine activity of said patient based on said parameter analysis.

2. The method of claim 1, wherein said analyzing further comprise determining the frequency, duration, amplitude, and power density spectrum of said bursts and the frequency, duration, and amplitude of a plurality of action potentials in one or more of said bursts.

3. The method of claim 1, wherein said analyzing further comprises:
   a. determining the mean frequency of a plurality of action potentials in at least one of said bursts;
   b. determining the starting frequency of action potentials in at least one of said bursts; and
   c. determining the ending frequency of action potentials in at least one of said bursts.

4. The method of claim 2, wherein said analyzing further comprises:
   a. determining the rate of rise of amplitude in at least one action potential in at least one of said bursts; and
   b. determining the rate of fall of amplitude in at least one action potential in at least one of said bursts.

5. The method of claim 1, wherein said analyzing uterine activity comprises examining one or more trends in uterine activity indicating parameters over time.

6. The method of claim 5, further comprising displaying one or more trends in uterine activity indicating parameters over time.

7. The method of claim 5, further comprising the step of predicting future uterine activity based upon one or more identified trends of examined uterine activity indicating parameters.

8. The method of claim 7, wherein said predicting future uterine activity comprises the steps of:
   a. comparing identified trends of a patient's examined uterine activity with trend data collected from other patients in order to identify matching trends; and b. predicting future uterine activity for a patient under examination based upon the trend behavior shown in the matching trends.

9. The method of claim 8 wherein said predicting is performed with the use of an expert system.

10. The method of claim 7, wherein said predicting future uterine activity comprises using a chaotic model of electromyographic activity to predict future uterine activity.

11. The method of claim 7, wherein said predicting future uterine activity comprises identifying situations in which treatment for pharmacologically inducing or inhibiting labor in said patient may be indicated.

12. The method of claim 1, wherein said characterizing further comprises detecting the contraction of abdominal muscles in the patient.

13. The method of claim 1 wherein said analyzing uterine activity comprises determining the fast wavelet transform characteristics of said frequency components of bursts of action potential within said electromyographic signals.

14. The method of claim 1 wherein said analyzing step further comprises determining joint time-frequency characteristics of said frequency components of bursts of action potentials within said electromyographic signals.

15. The method of claim 1, further comprising:
   a. stimulating a vagina of said patient while said electromyographic signals are being stored; and
   b. diagnosing labor as a function of said analysis of uterine activity.

16. The method of claim 1, wherein said analyzing step further comprises generating a three dimensional mesh plot of said power density spectral characteristics, said mesh plot displaying energy levels versus frequency versus time of pregnancy.

17. An apparatus for recording and analyzing uterine electrical activity for the abdominal or vaginal surface, comprising
   a. at least one electrode capable of measuring action potentials emitted from the abdominal or vaginal surface of a patient under analysis and further capable of emitting an analog signal indicative of action potentials measured by said electrode;
   b. an amplifier electrically coupled to said electrode to receive and amplify a signal indicative of action potentials measured by said electrode;
   c. a memory comprising sufficient storage capacity to store data resulting from a sampling of electromyographic signals at a sampling frequency of at least 100 Hz for a duration of time sufficient to record at least five bursts of action potentials, said memory coupled to receive a digital input from said amplifier indicative of action potential signals received by said converter;
   d. a filtering device capable of segregating and identifying electromyographic signals, including action potentials, in a frequency range of 0.3 Hz to 50 Hz from electromyographic signals outside said range; and
   e. a computer comprising an expert system programmed to analyze the frequency, duration, amplitude, and power density spectrum of action potential bursts and individual action potentials, said expert system further being capable of characterizing uterine activity based upon said analysis.

18. The apparatus of claim 17, wherein said expert system is further capable of identifying abdominal muscle contraction.

19. The apparatus of claim 17, wherein said memory is capable of storing said electromyographic signals in discrete, predetermined frequency ranges.

20. The apparatus of claim 17, wherein said expert system is further capable of determining the mean frequency, starting frequency, and ending frequency of a plurality of action potentials.

21. The apparatus of claim 17, wherein said action potential measuring electrode is a needle electrode.

22. The apparatus of claim 17, further comprising a monitor coupled to said computer, said monitor capable of displaying said electromyographic signals.

23. A remote uterine monitoring system for remotely characterizing uterine activity, comprising:
   a. at least one electrode capable of measuring action potentials emitted from the abdominal or vaginal surface of a patient under analysis and further capable of emitting an analog signal indicative of action potentials measured by said electrode;
   b. an amplifier electrically coupled to said electrode to receive and amplify a signal indicative of action potentials measured by said electrode;
   c. a data transmission system capable of receiving an amplified signal from said amplifier and transmitting said signal to a remote location from said electrode;
   d. a remote analog to digital converter coupled to said data transmission system to receive an analog input from said amplifier indicative of action potentials measured by said electrode;
   e. a memory comprising sufficient storage capacity to store data resulting from a sampling of electromyographic signals at a sampling frequency of at least 100 Hz for a duration of time sufficient to record at least five bursts of action potentials, said memory coupled to receive a digital input from said analog to digital converter indicative of action potential signals received by said converter;
   f. a filtering device capable of segregating and identifying electromyographic signals, including action potentials, in a frequency range of 0.3 Hz to 50 Hz from electromyographic signals outside said range; and
   g. a computer comprising an expert system programmed to analyze the frequency, duration, amplitude, and power density spectrum of action potential bursts and individual action potentials, said expert system further being capable of characterizing uterine activity based upon said analysis.

* * * * *